United States Patent
Protter et al.

(10) Patent No.: US 9,517,229 B2
(45) Date of Patent: Dec. 13, 2016

(54) TREATMENT OF BREAST CANCER

(75) Inventors: Andrew A. Protter, San Francisco, CA (US); Jennifer Richer, Aurora, CO (US); Dawn Cochrane, Aurora, CO (US)

(73) Assignees: MEDIVATION PROSTATE THERAPEUTICS, INC., San Francisco, CA (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 14/236,036

(22) PCT Filed: Jul. 27, 2012

(86) PCT No.: PCT/US2012/048471
§ 371 (c)(1),
(2), (4) Date: Jun. 10, 2014

(87) PCT Pub. No.: WO2013/066440
PCT Pub. Date: May 10, 2013

(65) Prior Publication Data
US 2014/0296312 A1    Oct. 2, 2014

Related U.S. Application Data

(60) Provisional application No. 61/513,361, filed on Jul. 29, 2011.

(51) Int. Cl.
A61K 31/4184    (2006.01)
A61K 31/4166    (2006.01)

(52) U.S. Cl.
CPC ....... *A61K 31/4184* (2013.01); *A61K 31/4166* (2013.01)

(58) Field of Classification Search
CPC .......................... A61K 31/416; A61K 31/4184
See application file for complete search history.

(56) References Cited

U.S. PATENT DOCUMENTS

| | | |
|---|---|---|
| 2007/0004753 A1 | 1/2007 | Sawyers et al. |
| 2008/0139634 A2 | 6/2008 | Jung et al. |
| 2009/0111864 A1 | 4/2009 | Jung et al. |
| 2010/0172975 A1 | 7/2010 | Sawyers et al. |
| 2010/0210665 A1 | 8/2010 | Sawyers et al. |
| 2011/0003839 A1 | 1/2011 | Jung et al. |
| 2011/0130296 A1 | 6/2011 | Benz et al. |
| 2011/0152348 A1 | 6/2011 | Worm et al. |
| 2012/0214864 A1 | 8/2012 | Richer et al. |

FOREIGN PATENT DOCUMENTS

| | | |
|---|---|---|
| WO | 2010099238 A1 | 9/2010 |
| WO | 2010118354 A1 | 10/2010 |
| WO | 2011044327 A1 | 4/2011 |

OTHER PUBLICATIONS

De Amicis et al. "Androgen Receptor Overexpression Induces Tamoxifen Resistance in Human Breast Cancer Cells" Breast Cancer Res. Treat. 2010, 121(1), 1-11.*
"Tamoxifen" Dec. 2004 [online]: Wikipedia [retrieved on May 5, 2015]. Retrieved from <http://en.wikipedia.org/wiki/Tamoxifen>.*
International Search Report and Written Opinion mailed Apr. 1, 2012 (PCT/US2012/048471); ISA/US.
International Preliminary Report on Patentability with Written Opinion for PCT/US2012/048471, mailed Feb. 4, 2014.
Cochrane et al., "Role of the androgen receptor in breast cancer and preclinical analysis of enzalutamide," Breast Cancer Research, vol. 16, No. 1, Jan. 22, 2014, p. R7.
De Amicis et al., "Androgen receptor overexpression induces tamoxifen resistance in human breast cancer cells," Breast Cancer Research and Treatment, vol. 121, No. 1, Jun. 17, 2009, pp. 1-11.
Doane et al., "An estrogen receptor-negative breast cancer subset characterized by a hormonally regulated transcriptional program and response to androgen," Oncogene, vol. 25, No. 28, Feb. 20, 2006, pp. 3994-4008.
Graham et al., "Reciprocal regulation of ZEB1 and AR in triple negative breast cancer cells", Breast Cancer Research and Treatment, vol. 123, No. 1, Nov. 18, 2009, pp. 139-147.
Lehmann et al., "Identification of human triple-negative breast cancer subtypes and preclinical models for selection of targeted therapies," Journal of Clinical Investigation, vol. 121, No. 7, Jul. 1, 2011, pp. 2750-2767.
Ni et al., "Targeting Androgen Receptor in Estrogen Receptor-Negative Breast Cancer," Cancer Cell, vol. 20, No. 1, May 27, 2011, pp. 119-131.
Robinson et al., "Androgen receptor driven transcription in molecular apocrine breast cancer is mediated by FoxA1," The EMBO Journal, vol. 31, No. 6, Jun. 24, 2011, pp. 3019-3027.
Santana-Davila et al., "Treatment options for patients with triple-negative breast cancer," Journal of Hematology & Oncology, vol. 3, No. 1, Oct. 27, 2010, pp. 1-11.
Supplementary European Search Report for EP 12 84 6720, dated Feb. 9, 2015.

* cited by examiner

*Primary Examiner* — Nyeemah A Grazier
*Assistant Examiner* — Amanda L Aguirre
(74) *Attorney, Agent, or Firm* — Banner & Witcoff, Ltd.

(57) ABSTRACT

The disclosure describes the use of one or more compounds that fall within the scope of one or more of structural formulae I, II, III, IV, V, or VI for treating triple negative breast Compounds useful for treating breast cancer include those compounds of formulae I, II, III, IV, V, or VI that inhibit proliferation of breast cancer cells and/or lead to the death of breast cancer cells, especially triple negative breast cancer.

23 Claims, 15 Drawing Sheets

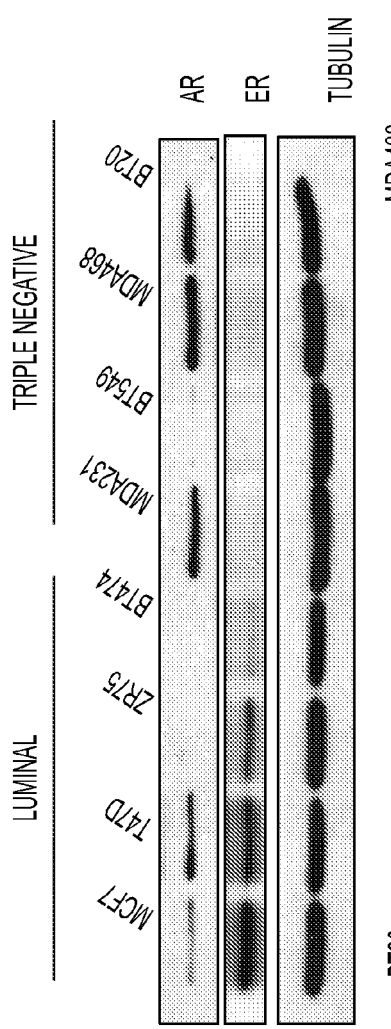
FIG. 6A
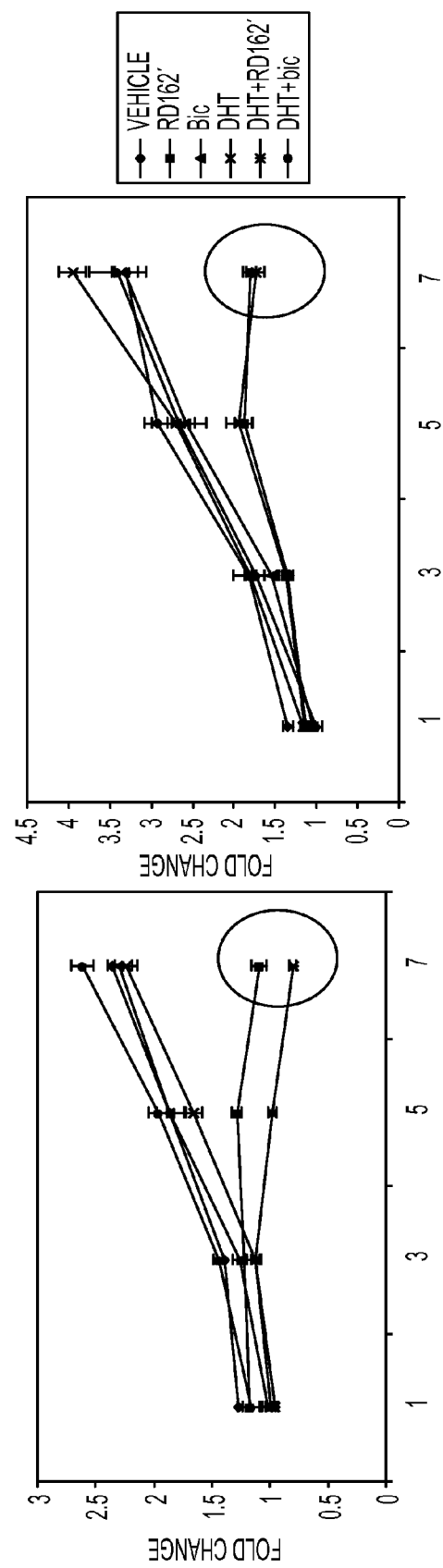
FIG. 6B
FIG. 6C

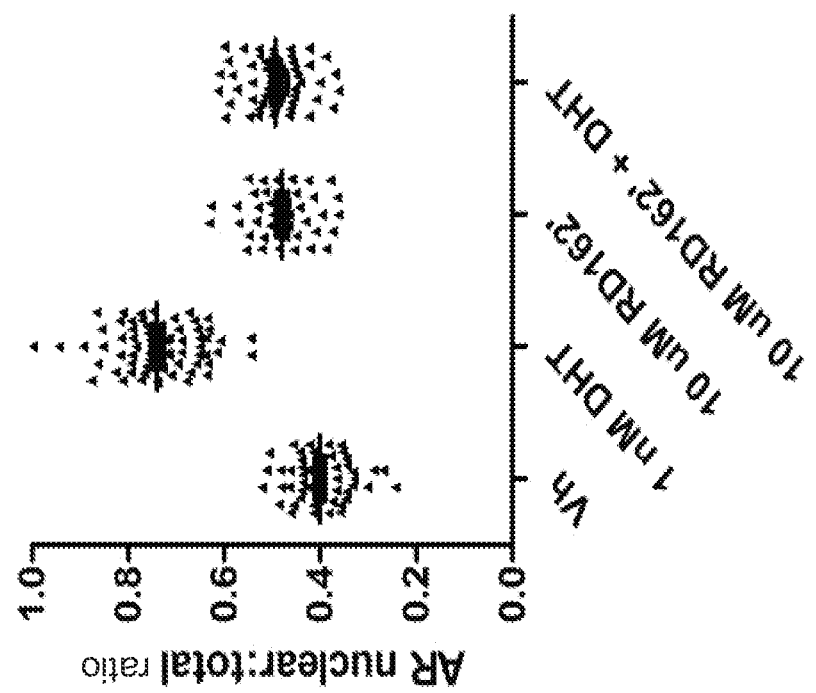

# TREATMENT OF BREAST CANCER

This application claims the benefit of and incorporates by reference Ser. No. 61/513,361 filed on Jul. 29, 2011.

This invention was made with government support under grant number W81XWM-08-1-0311 awarded by Army Medical Research Material and Command. The government has certain rights in the invention.

All documents cited in this disclosure are incorporated herein by reference in their entireties.

TECHNICAL FIELD

The technical field is treatment of breast cancer.

BRIEF DESCRIPTION OF THE DRAWINGS

FIG. 3A, graph demonstrating that RD162' blocks estradiol (E2)-mediated growth in MCF7 cells. Error bars represent standard error of the mean for 6 wells at each time point. See Example 3. FIG. 3B, Western blot demonstrating expression of estrogen receptor alpha treated for 48 hours under various conditions and a tubulin (a loading control).

FIG. 5A, caliper measurements of tumor size over time. FIG. 5B, whole body in vivo luminescent (IVIS) imaging over time. FIG. 5C, caliper measurements of individual tumor size at the end of the study. FIG. 5D, IVIS measurements of individual tumor size at the end of the study.

FIGS. 6A-C. FIG. 6A, Western blot of four luminal (ER+, PR+) and four triple negative (ER−, PR−, Her2−) breast cancer cell lines for androgen receptor, estrogen receptor and tubulin (as a loading control). FIG. 6B, graph demonstrating that RD162' inhibits cell growth in triple negative breast cancer cell line BT20 and actually decreases cell viability. FIG. 6C, graph demonstrating that RD162' inhibits cell growth in triple negative breast cancer cell line MDA468 and actually decreases cell viability.

FIGS. 7A-E. FIG. 7A, Graph showing results of an MTS in vitro proliferation assay using MDA-MB-453 cells (AR+, ER−, HER2+, PR−), indicating that 10 μM RD162' inhibits proliferation induced by 10 nM DHT. FIG. 7B, Graph showing results of a luciferase assay with MDA-kb2 cells, demonstrating that RD162' inhibits proliferation induced by DHT in a dose dependent manner. FIG. 7C, Graph showing the ratio of nuclear to total AR in MDA-kb2 cells treated as described in Example 7. FIG. 7D and FIG. 7E, Graphs demonstrating that RD162' inhibits tumor growth induced by DHT.

DETAILED DESCRIPTION

Figure 1:
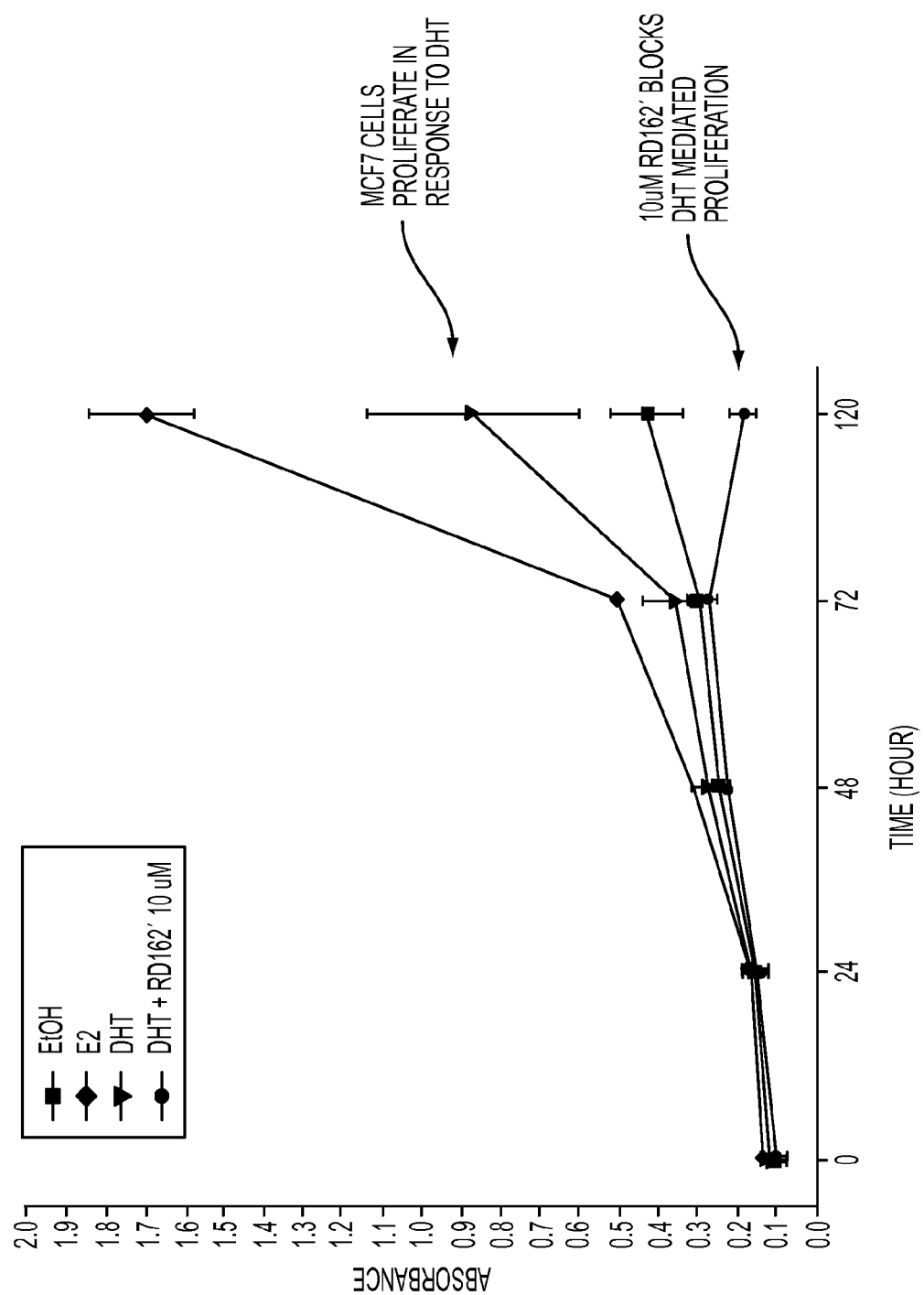
FIG. 1. Graph demonstrating that RD162' blocks DHT-mediated growth in MCF7 cells. Error bars represent standard error of the mean for 6 wells at each time point. See Example 1.

This disclosure describes the use of one or more compounds that fall within the scope of one or more of structural formulae I, II, III, IV, V, or VI for treating breast cancer. Compounds useful for treating breast cancer include those compounds of formula I, II, III, IV, V, or VI that inhibit proliferation of breast cancer cells and/or lead to the death of breast cancer cells.

1. Definitions for Formulae I and II

The following definitions apply to Formulae (I) and (II).

The term "alkyl" denotes branched or unbranched hydrocarbon chains, in some embodiments having about 1 to about 8 carbons, such as, methyl, ethyl, n-propyl, isopropyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which can be attached to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, in some embodiments 3 to 10 carbons, forming the ring and which can be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl;" for example:

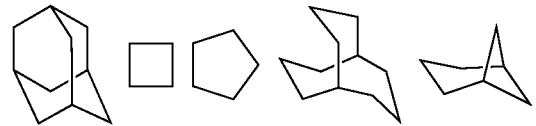

-continued

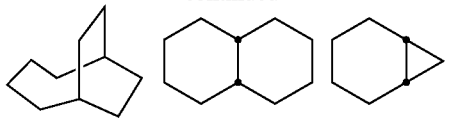

and the like.

Unless otherwise indicated, the term "alkenyl" as used herein by itself or as part of another group refers to straight or branched chain radicals of 2 to 20 carbons, in some embodiments 2 to 12 carbons, and in some embodiments 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, in some embodiments 2 to 12 carbons and in some embodiments 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, fluorine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and can optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heterocyclic" or "heterocycle", as used herein, represents an unsubstituted or substituted stable 5- to 10-membered monocyclic ring system which can be saturated or unsaturated, and which consists of carbon atoms and from one to four heteroatoms selected from N, O or S, and wherein the nitrogen and sulfur heteroatoms can optionally be oxidized, and the nitrogen heteroatom can optionally be quaternized. The heterocyclic ring can be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents. such as the substituents included above in the definition of "substituted alkyl" and "substituted cycloalkyl." Examples of heteroaryl groups include the following:

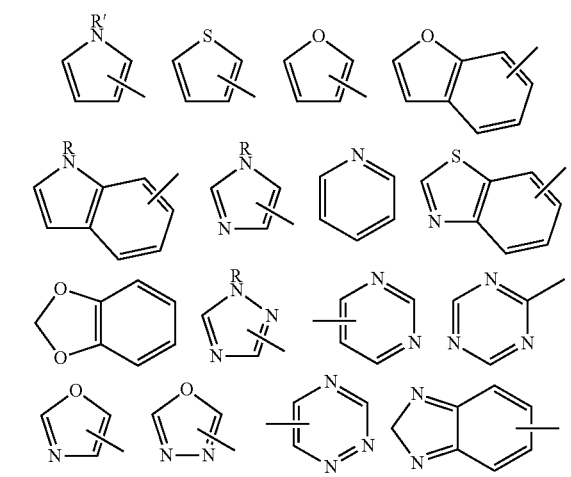

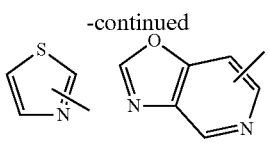

and the like.

2. Definitions for Formula III, IV, and V

The following definitions apply to Formulae (III), (IV), and (V).

"Alkyl" refers to and includes saturated linear, branched, or cyclic hydrocarbon structures and combinations thereof. Particular alkyl groups are those having 1 to 12 carbon atoms (a "$C_1$-$C_{12}$ alkyl"). More particular alkyl groups are those having 1 to 8 carbon atoms (a "$C_1$-$C_8$ alkyl"). When an alkyl group having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, isopropyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. In some embodiments cycloalkyl has from 3 to 12 annular carbon atoms (a "$C_3$-$C_{12}$ cycloalkyl"). In some embodiments cycloalkyl has from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Alkenyl" refers to an unsaturated linear, branched, or cyclic hydrocarbon group having at least one site of olefinic unsaturation (i.e., having at least one moiety of the formula C=C) and in some embodiments having from 2 to 10 carbon atoms and more in some embodiments 2 to 8 carbon atoms. Examples of alkenyl groups include but are not limited to —$CH_2$—CH=CH—$CH_3$ and —$CH_2$—$CH_2$-cyclohexenyl, where the ethyl group of the later example can be attached to the cyclohexenyl moiety at any available position on the ring.

"Alkynyl" refers to an unsaturated linear, branched, or cyclic hydrocarbon group having at least one site of acetylenic unsaturation (i.e., having at least one moiety of the formula C≡C) and in some embodiments having from 2 to 10 carbon atoms and more in some embodiments 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to an alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to an alkynyl group having from 1 to 5 substituents including, but not limited to, groups such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Aryl," "arene" or "Ar" refers to an unsaturated aromatic carbocyclic group having a single ring (e.g., phenyl) or multiple condensed rings (e.g., naphthyl or anthryl). In some embodiments the aryl group contains from 6 to 14 annular carbon atoms.

"Heteroaryl," "heteroarene" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl).

"Substituted aryl" or "substituted arene" refers to an aryl group having from 1 to 5 substituents including, but not limited to, groups such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" or "substituted heteroarene" refers to a heteroaryl group having from 1 to 5 substituents including, but not limited to, groups such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, aryl, substituted aryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. In some embodiments an aralkyl is connected to the parent structure via the alkyl moiety.

"Aralkenyl" refers to a residue in which an aryl moiety is attached to an alkenyl residue and wherein the aralkenyl group may be attached to the parent structure at either the aryl or the alkenyl residue. In some embodiments an aralkenyl is connected to the parent structure via the alkenyl moiety.

"Aralkynyl" refers to a residue in which an aryl moiety is attached to an alkynyl residue and wherein the aralkynyl group may be attached to the parent structure at either the aryl or the alkynyl residue. In some embodiments an aralkynyl is connected to the parent structure via the alkynyl moiety.

"Heteroaralkyl" refers to a residue in which a heteroaryl moiety is attached to an alkyl residue and wherein the heroaralkyl group may be attached to the parent structure at either the heteroaryl or the alkyl residue. In some embodiments a heteroaralkyl is connected to the parent structure via the alkyl moiety.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In some embodiments a substituted heterocycle is a heterocycle substituted with an additional ring, wherein the additional ring may be aromatic or non-aromatic.

"Halo" or "halogen" refers to elements of the Group 17 series having atomic number 9 to 85. In some embodiments halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. Similarly, a "haloalkenyl" or "haloalkynyl" indicates an alkenyl or alkynyl moiety respectively in which at least one H is replaced with a halo group. An alkyl group in which each H is replaced with a halo group is referred to as a "perhaloalkyl." In some embodiments a perhaloalkyl group is trifluoromethyl ($-CF_3$).

A "substituted" group similarly refers to a group which is substituted with from 1 to 5 substituents including, but not limited to, substituents such as alkoxy, substituted alkoxy, acyl, acyloxy, carbonylalkoxy, acylamino, substituted or unsubstituted amino, aminoacyl, substituted or unsubstituted carbamoyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like.

3. Diarylhydantoin Compounds

In some embodiments the compound of formula I, II, III, IV, V, or VI is a diarylhydantoin compound. Useful diarylhydantoin compounds and their syntheses are disclosed, for example, in U.S. Pat. No. 7,709,517.

In some embodiments the compound is a compound of Formula I:

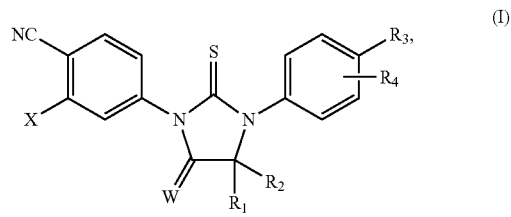

wherein X is selected from the group consisting of trifluoromethyl and iodo, wherein W is selected from the group consisting of O and NR5, wherein R5 is selected from the group consisting of H, methyl, and

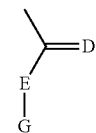

wherein D is S or O and E is N or O and G is alkyl, aryl, substituted alkyl or substituted aryl; or D is S or O and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

In some embodiments R5 is

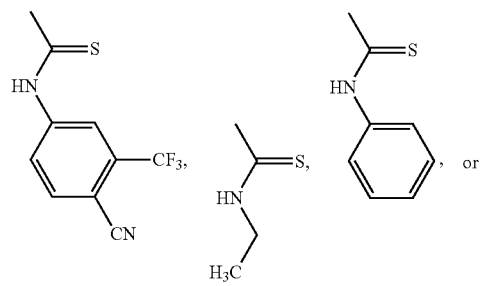

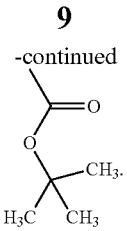

In some embodiments the compound is a compound of Formula I-A:

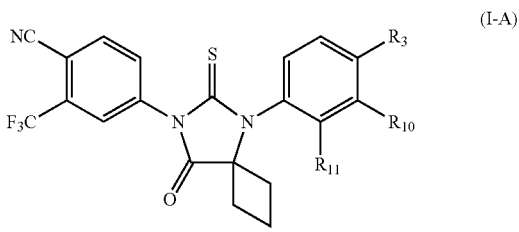

(I-A)

wherein R3 is selected from the group consisting of hydroxy, methylcarbamoyl, methylcarbamoylpropyl, methylcarbamoylethyl, methylcarbamoylmethyl, methylsulfonecarbamoylpropyl, methylaminomethyl, dimethylaminomethyl, methylsulfonyloxymethyl, carbamoylmethyl, carbamoylethyl, carboxymethyl, methoxycarbonylmethyl, methanesulfonyl, 4-cyano-3-trifluoromethylphenylcarbamoylpropyl, carboxypropyl, 4-methanesulfonyl-1-piperazinyl, piperazinyl, methoxycarbonyl, 3-cyano-4-trifluoromethylphenylcarbamoyl, hydroxyethylcarbamoylethyl, and hydroxyethoxycarbonylethyl, and wherein R10 and R11 are both H or, respectively, F and H, or H and F. In some embodiments R10 and R11 can both be H or, respectively, F and H, R3 can be methylcarbamoyl.

In some embodiments R1 and R2 are independently methyl or, together with the carbon to which they are linked, a cycloalkyl group of 4 to 5 carbon atoms, and R3 is selected from the group consisting of carbamoyl, alkylcarbamoyl, carbamoylalkyl, and alkylcarbamoylalkyl, and R4 is H or F or R4 is 3-fluoro.

In some embodiments R1 and R2 are independently methyl or, together with the carbon to which they are linked, a cycloalkyl group of 4 to 5 carbon atoms, R3 is selected from the group consisting of cyano, hydroxy, methylcarbamoyl, methylcarbamoyl-substituted alkyl, methylsulfonecarbamoyl-substituted alkyl, methylaminomethyl, dimethylaminomethyl, methylsulfonyloxymethyl, methoxycarbonyl, acetamido, methanesulfonamido, carbamoyl-substituted alkyl, carboxymethyl, methoxycarbonylmethyl, methanesulfonyl, 4-cyano-3-trifluoromethylphenylcarbamoyl-substituted alkyl, carboxy-substituted alkyl, 4-(1,1-dimethylethoxy)carbonyl)-1-piperazinyl, 4-methanesulfonyl-1-piperazinyl, piperazinyl, hydroxyethylcarbamoyl-substituted alkyl, hydroxyethoxycarbonyl-substituted alkyl, and 3-cyano-4-trifluoromethylphenylcarbamoyl, and R4 is F.

In some embodiments the compound is a compound of Formula I-B:

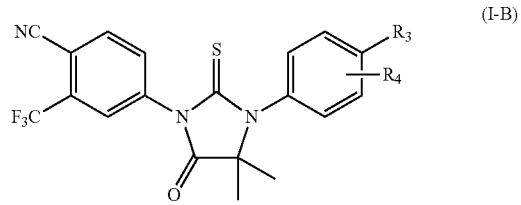

(I-B)

wherein R3 is selected from the group consisting of methylcarbonyl, methoxycarbonyl, acetamido, and methanesulfonamido, and R4 is selected from the group consisting of F and H.

In some embodiments the compound is a compound of Formula I-C:

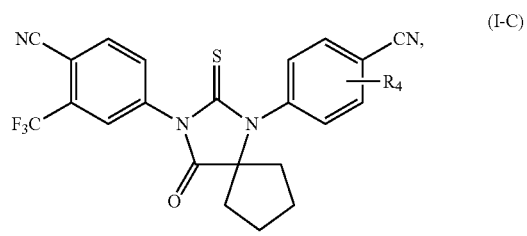

(I-C)

wherein R4 is selected from the group consisting of F and H.

In some embodiments R1 and R2, together with the carbon to which they are linked, are

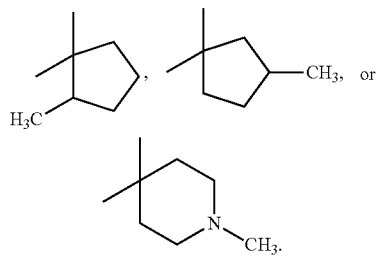

In some embodiments the compound is a compound of Formula I-D:

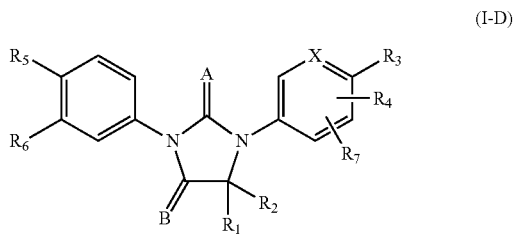

(I-D)

wherein R5 is CN or NO2 or SO2R11, wherein R6 is CF3, alkyl, substituted alkyl, alkenyl, substituted alkenyl, alkynyl, substituted alkynyl, halogenated alkyl, halogenated alkenyl, halogenated alkynyl, halogen, wherein A is sulfur (S) or oxygen (O), wherein B is O or S or NR8, wherein R8 is selected from the group consisting of H, methyl, aryl, substituted aryl, alkyl, substituted alkyl, alkenyl, substituted alkenyl, alkynyl, substituted alkynyl, arylalkyl, arylalkenyl, arylalkynyl, heterocyclic aromatic or non-aromatic, substituted heterocyclic aromatic or non-aromatic, cycloalkyl, substituted cycloalkyl, SO2R11, NR11R12, (CO)OR11, (CO)NR11R12, (CO)R11, (CS)R11, (CS)NR11R12, (CS)OR11,

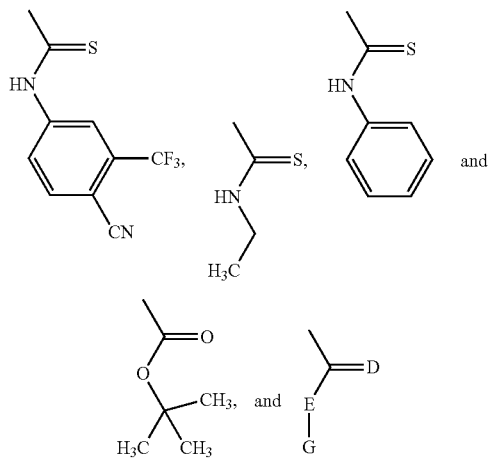

wherein D is S or O and E id N or O and G is alkyl, aryl, substituted alkyl or substituted aryl; or D is S or O and E-G together are C1-C4 lower alkyl, wherein R1 and R2 are independently alkyl, haloalkyl, hydrogen, aryl, substituted alkyl, alkenyl, substituted alkenyl, alkynyl, substituted alkynyl, halogenated alkenyl, halogenated alkynyl, arylalkyl, arylalkenyl, arylalkynyl, heterocylic aromatic or non-aromatic, substituted heterocyclic aromatic or non-aromatic, cycloalkyl, substituted cycloalkyl, or R1 and R2 are connected to form a cycle which can be heterocyclic, substituted heterocyclic, cycloalkyl, substituted cycloalkyl,

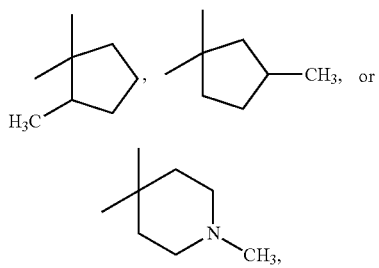

wherein X is carbon or nitrogen and can be at any position in the ring, and wherein R3, R4, and R7 are independently selected from the group consisting of hydrogen, halogen, methyl, methoxy, formyl, haloacetoxy, trifluoromethyl, cyano, nitro, hydroxyl, phenyl, amino, methylcarbamoyl, methylcarbamoyl-substituted alkyl, dimethylcarbamoyl-substituted alkyl, methoxy carbonyl, acetamido, methanesulfonamino, carbamoyl-substituted alkyl, methanesulfonyl, 4-methanesulfonyl-piperazinyl, piperazinyl, hydroxyethylcarbamoyl-substituted alkyl, hydroxyl-substituted alkyl, hydroxyl-substituted alkenyl, carbamoyl-substituted alkenyl, methoxycarbonyl-substituted alkyl, cyano-substituted alkyl,

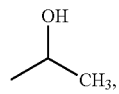

aryl, substituted aryl, alkyl, substituted alkyl, alkenyl, substituted alkenyl, alkynyl, substituted alkynyl, halogenated alkenyl, halogenated alkynyl, SO2R11, NR11R12, NR12(CO)OR11, NH(CO)NR11R12, NR12 (CO)R11, O(CO)R11, O(CO)OR11, O(CS)R11, NR12(CS)R11, NH(CS)NR11R12, NR12(CS)OR11, aryl alkyl, arylalkenyl, arylalkynyl, heterocyclic aromatic or non-aromatic, substituted heterocyclic aromatic or non-aromatic, cycloalkyl, substituted cycloalkyl, haloalkyl, methylsulfonecarbamoyl-substituted alkyl, methylaminomethyl, dimethylaminomethyl, methylsulfonyloxymethyl, methoxycarbonyl, acetamido, methanesulfonamido, carbamoyl-substituted alkyl, carboxymethyl, methoxycarbonylmethyl, methane sulfonyl, 4-cyano-3-trifluoromethylphenylcarbamoyl-substituted alkyl, carboxy-substituted alkyl, 4-(1,1-dimethylethoxy)carbonyl)-1-piperazinyl, hydroxyethylcarbamoyl-substituted alkyl, hydroxyethoxycarbonyl-substituted alkyl, 3-cyano-4-trifluoromethylphenylcarbamoyl, wherein R11 and R12 are independently hydrogen, aryl, aralkyl, substituted aralkyl, alkyl, substituted alkyl, alkenyl, substituted alkenyl, alkynyl, substituted alkynyl, halogenated alkyl, halogenated alkenyl, halogenated alkynyl, aryl alkyl, arylalkenyl, arylalkynyl, heterocyclic aromatic or non-aromatic, substituted heterocyclic aromatic or non-aromatic, cycloalkyl, or substituted cycloalkyl, or R11 and R12 can be connected to form a cycle which can be heterocyclic aromatic or non-aromatic, substituted heterocyclic aromatic, cycloalkyl, or substituted cycloalkyl.

In some embodiments the compound is a compound selected from:

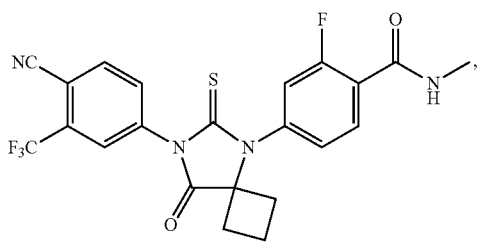

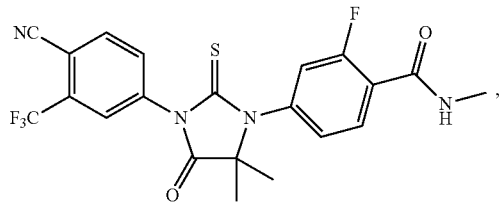

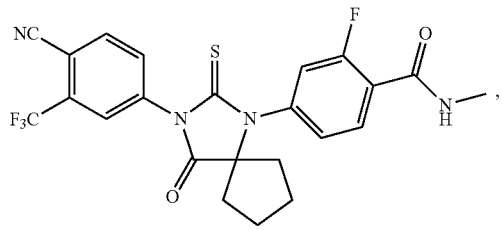

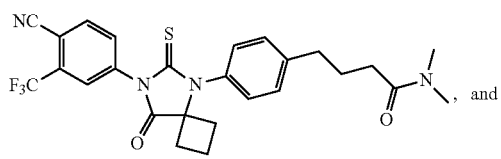
[RD169]
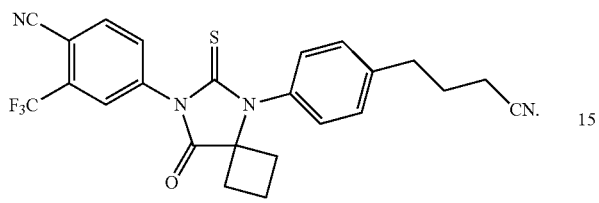
[RD170]
In some embodiments, the compound is RD162' (enzalutamide):
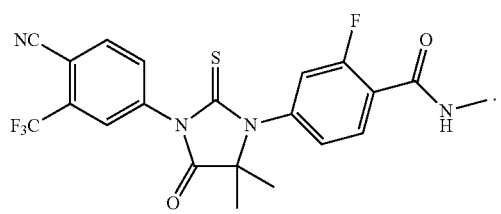
[RD162']
In some embodiments the compound is a compound disclosed in U.S. Pat. No. 7,709,517. In some embodiments the compound is a compound listed in Tier 1, Tier 2, Tier 3, and/or Tier 4 of U.S. Pat. No. 7,709,517, reproduced below:
TIER 1 COMPOUNDS
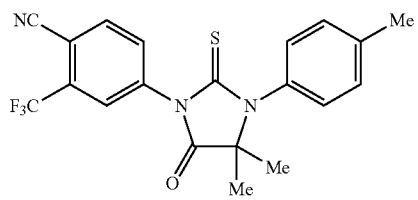
RD7
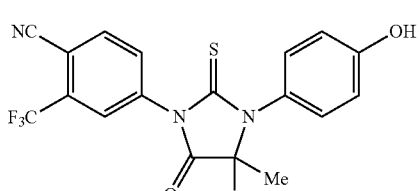
RD8
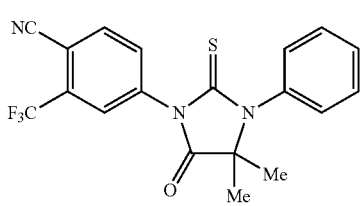
RD10
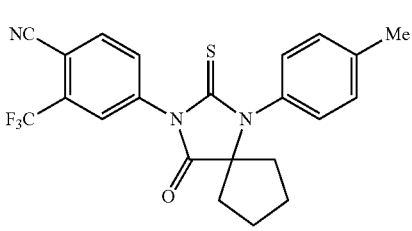
RD35
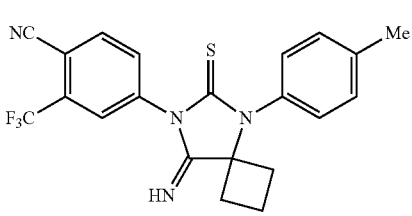
RD36
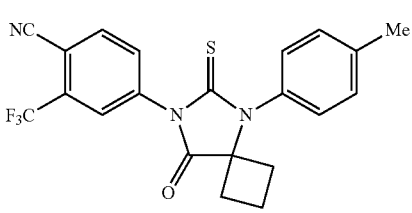
RD37
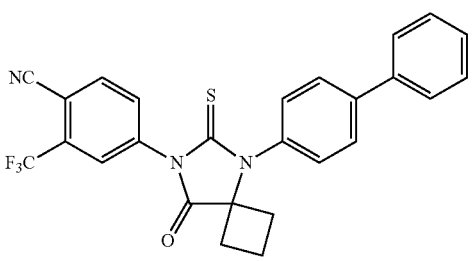
RD57
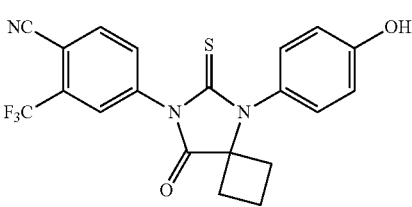
RD58
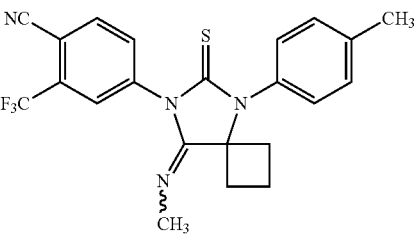
RD90
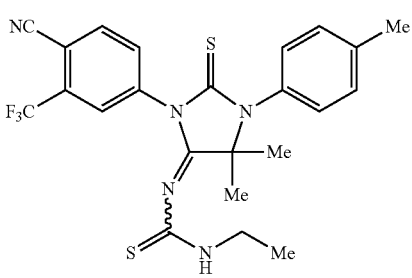
RD91

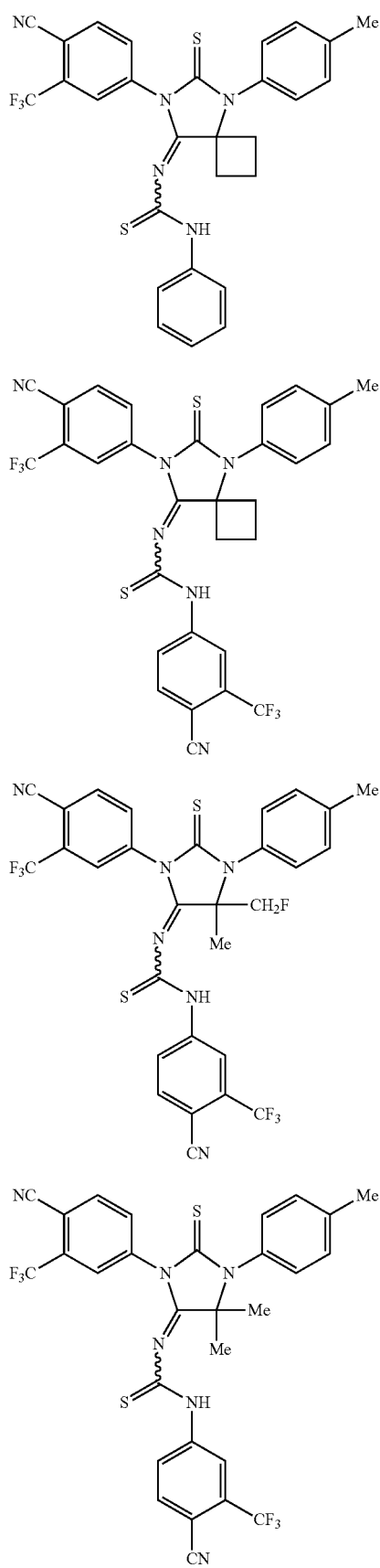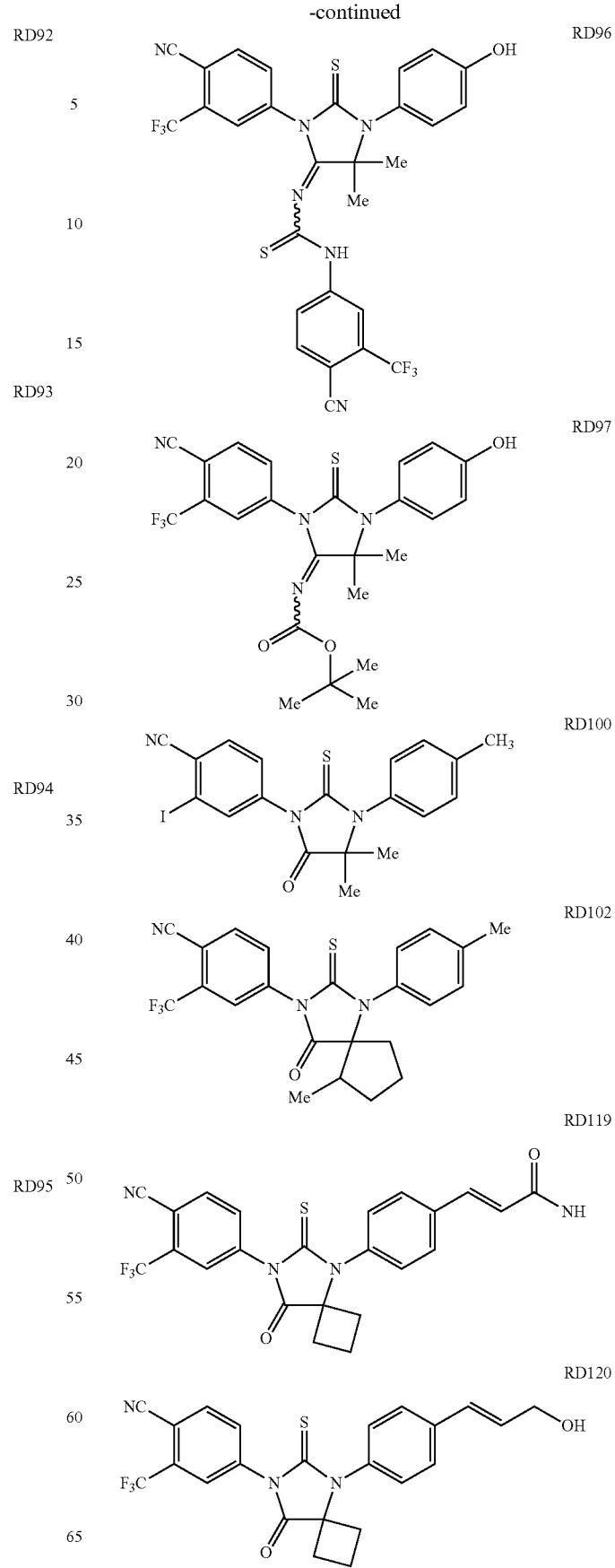

RD130
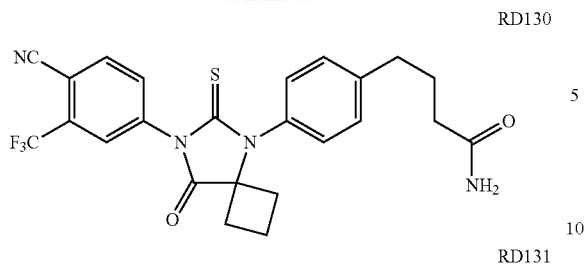
RD131
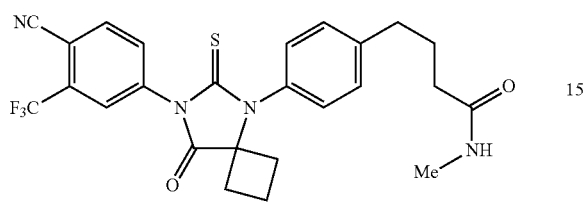
RD145
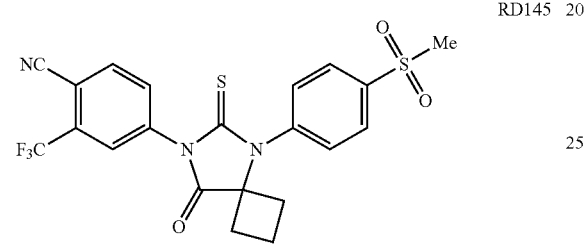
RD152
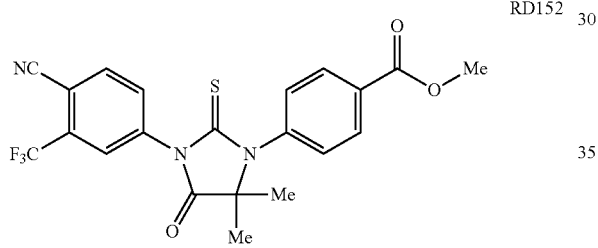
RD153
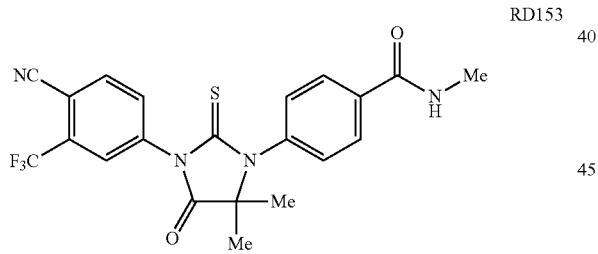
RD163
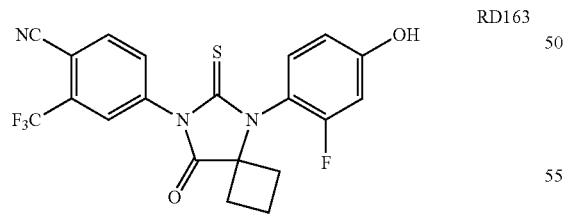
RD162
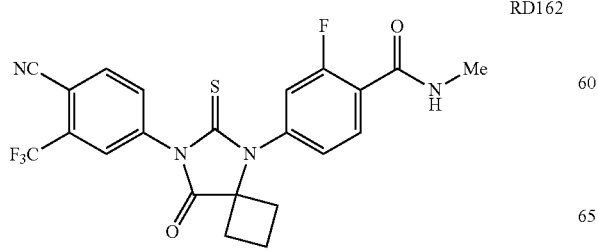
RD162
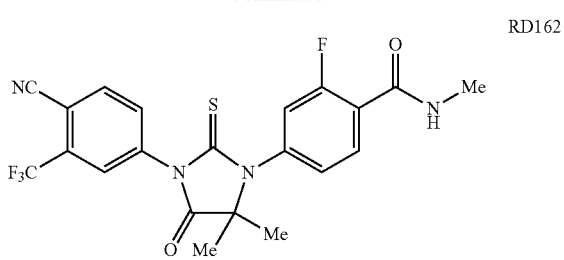
RD162″
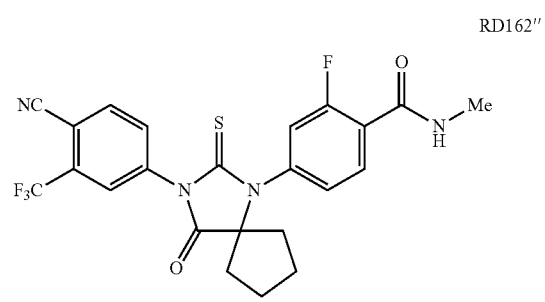
RD168
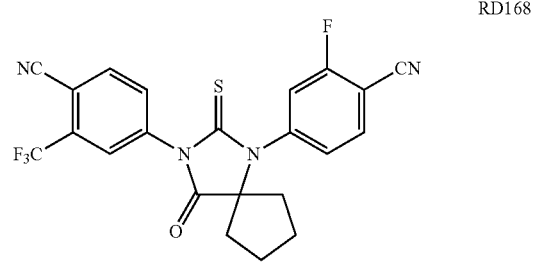
RD169
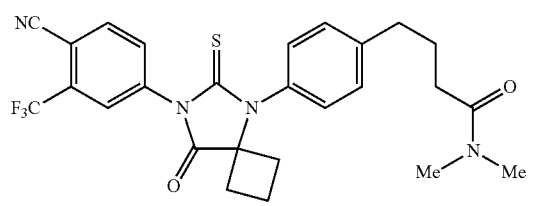
RD170
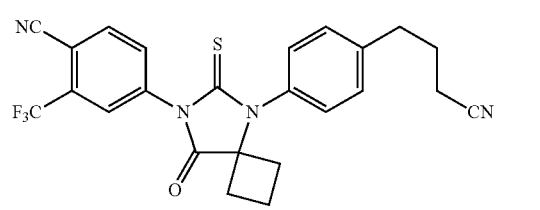
TIER 2 COMPOUNDS
RD6
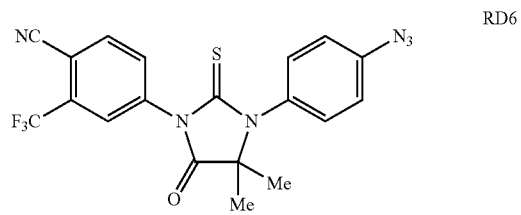

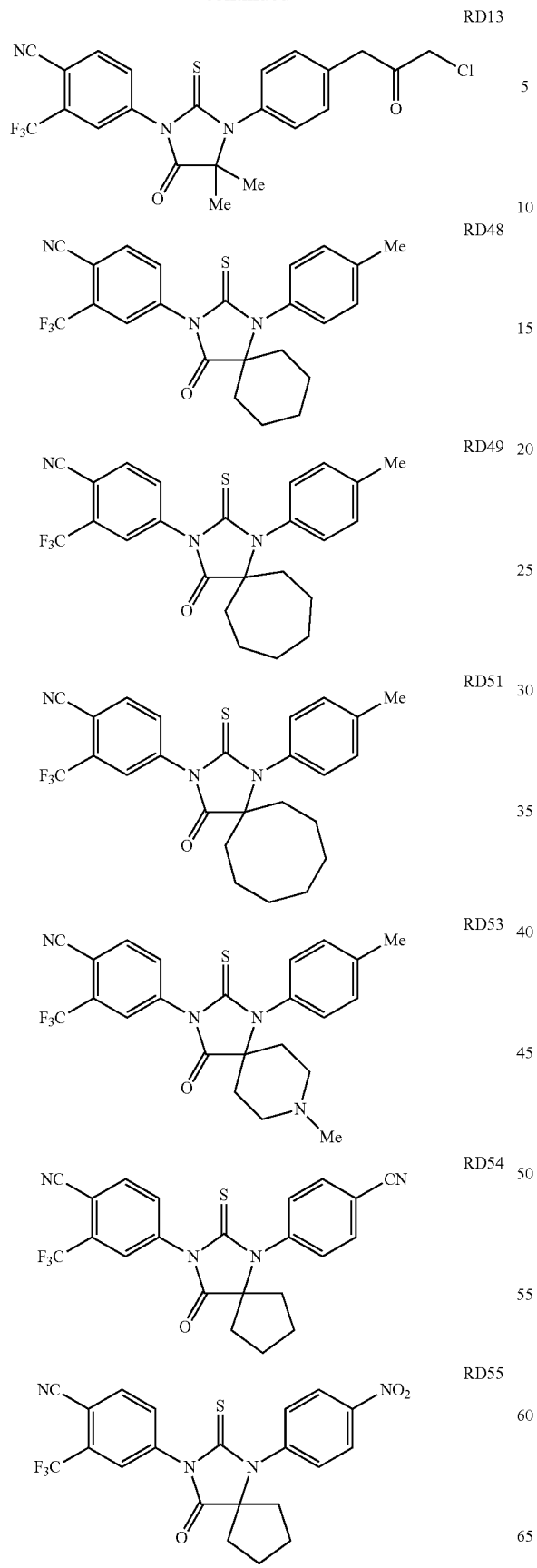
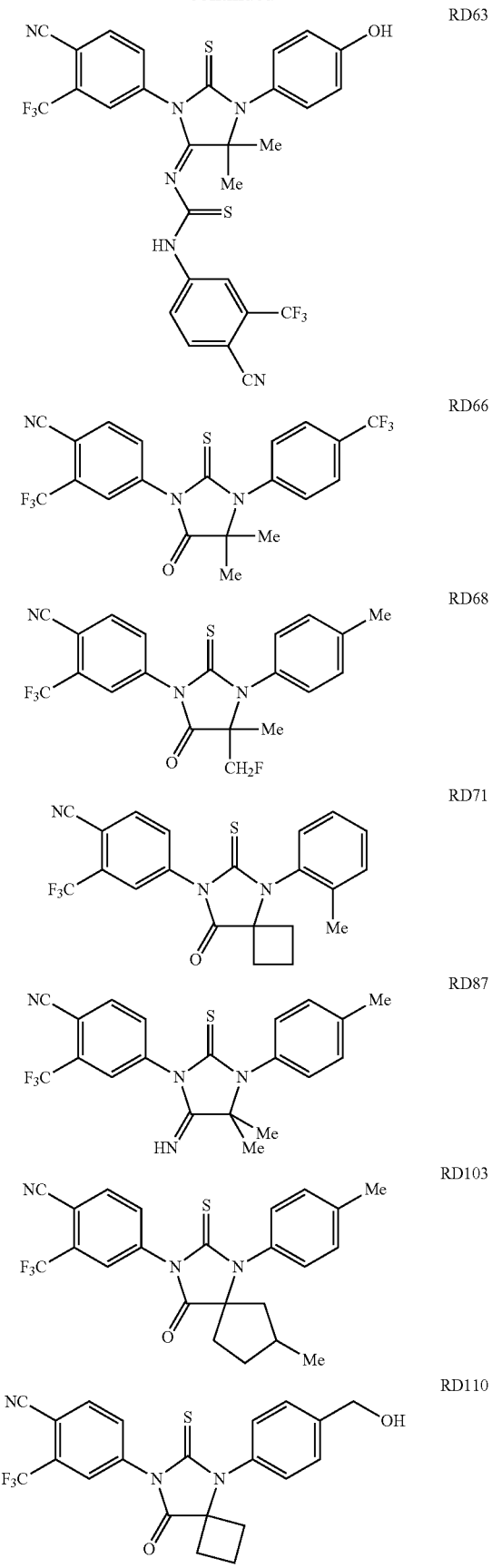

RD111
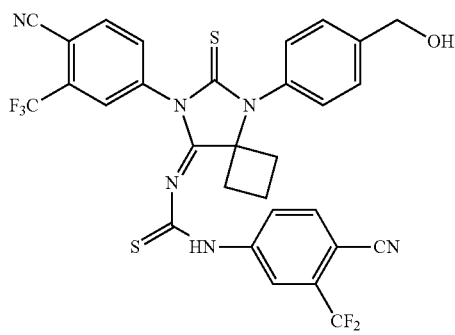
RD114
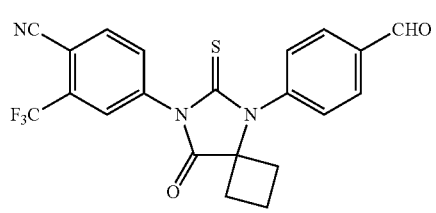
RD116
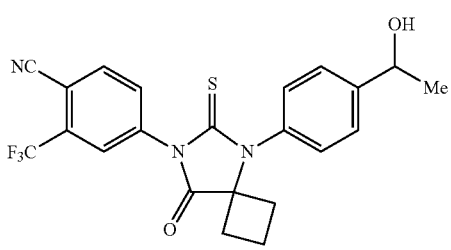
RD133
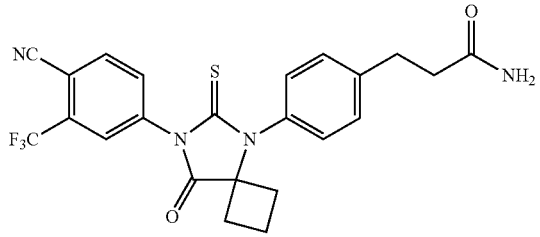
RD134
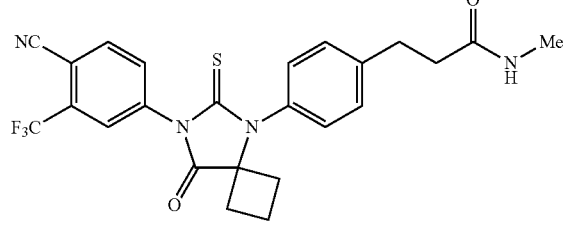
RD138
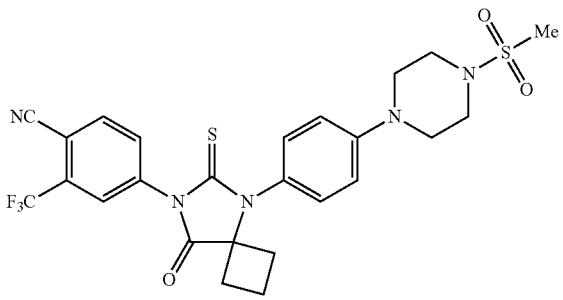
RD161
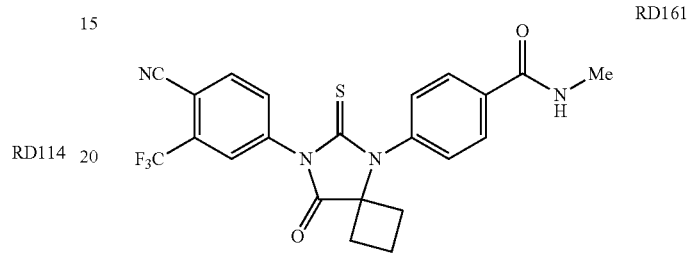
TIER 3 COMPOUNDS
RD3
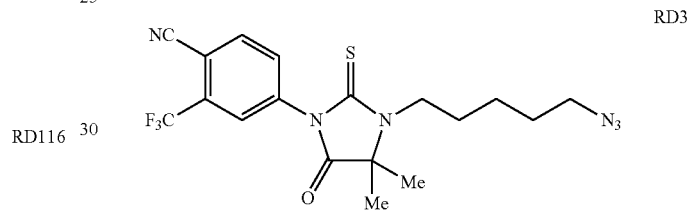
RD4
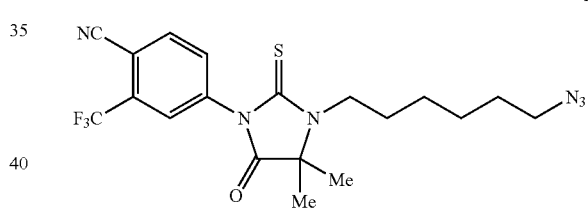
RD5
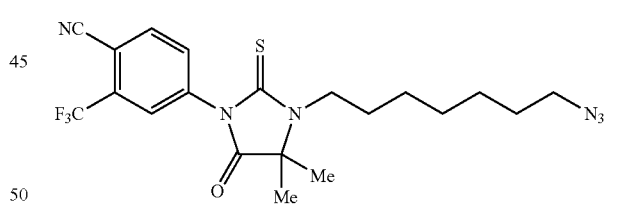
RD69
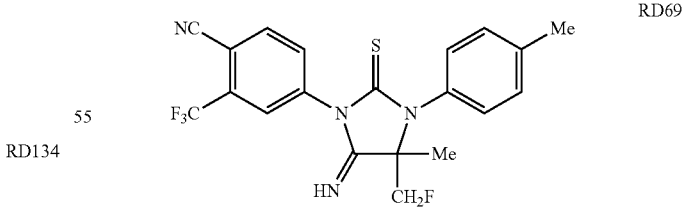
RD127
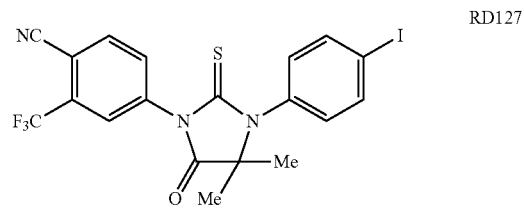

-continued
RD128
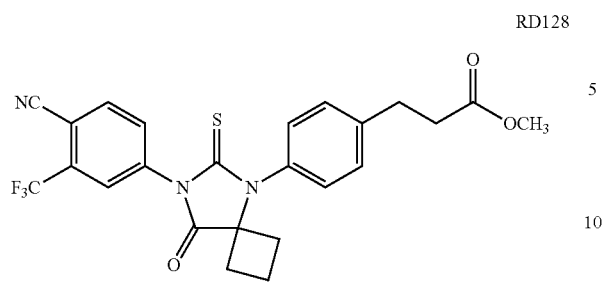
RD129
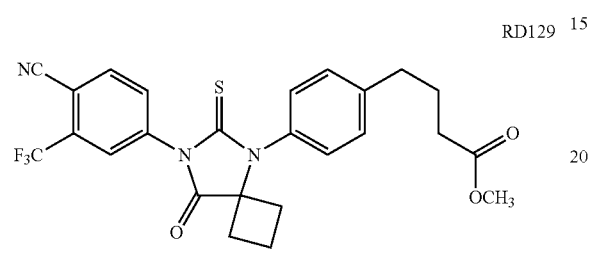
RD135
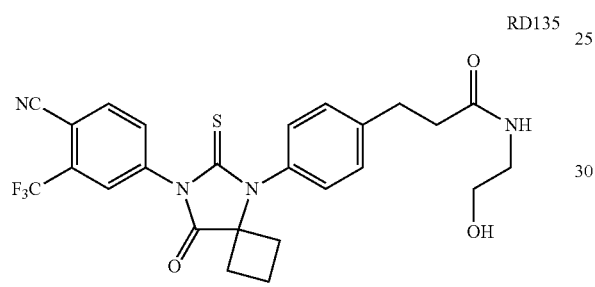
RD137
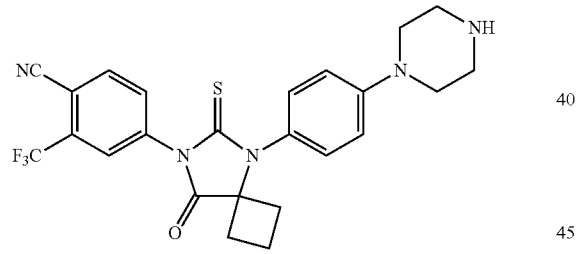
RD129
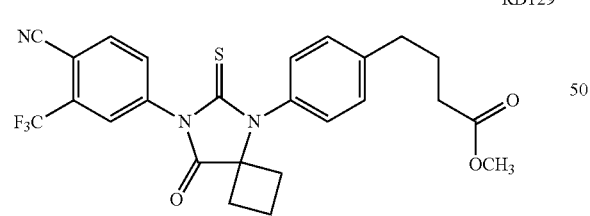
RD135
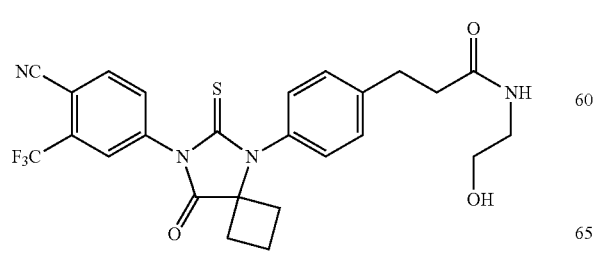
-continued
RD137
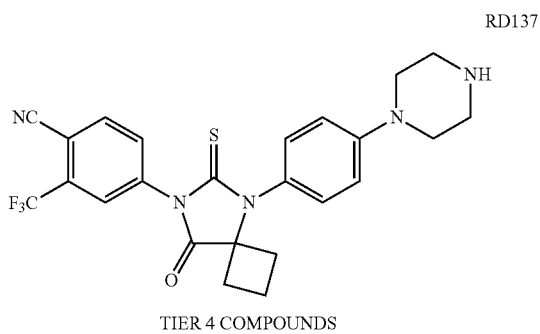
TIER 4 COMPOUNDS
RD2
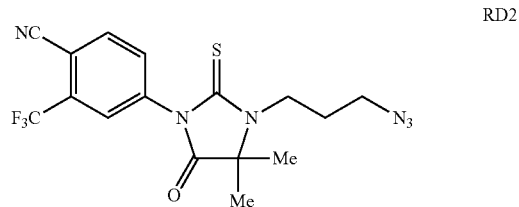
RD9
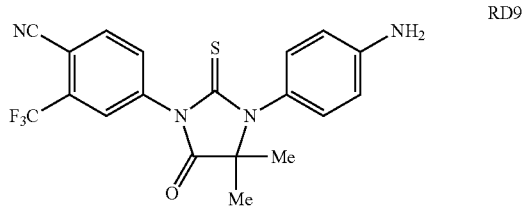
RD21
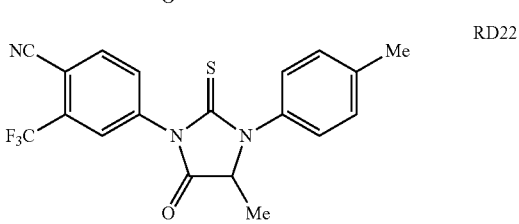
RD22
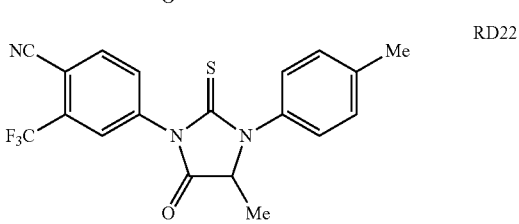
RD23
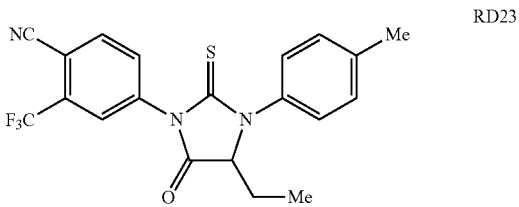
RD24
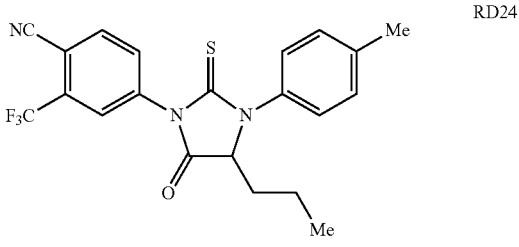

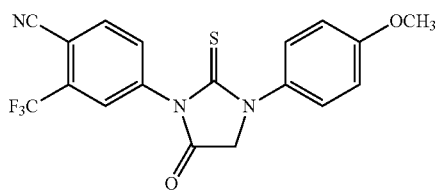 RD25
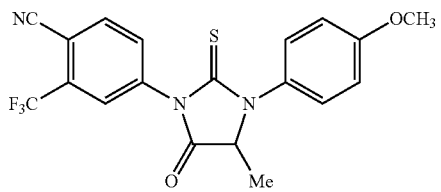 RD26
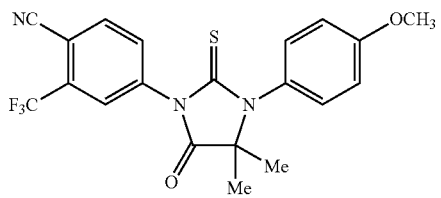 RD27
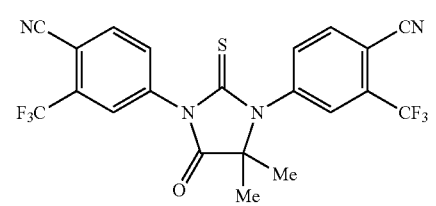 RD30
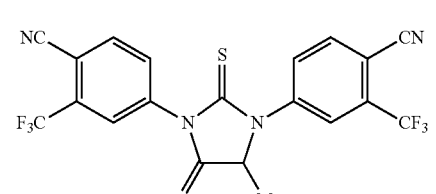 RD31
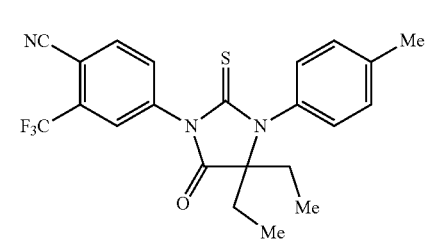 RD39
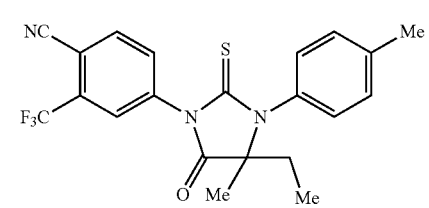 RD40
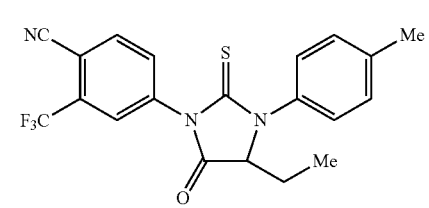 RD44
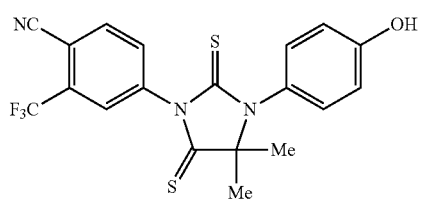 RD59
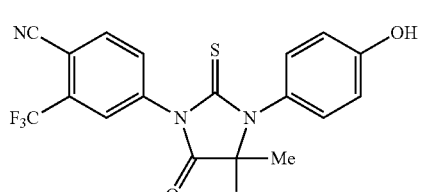 RD60
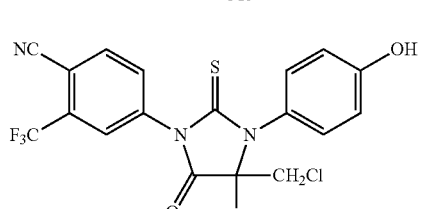 RD67
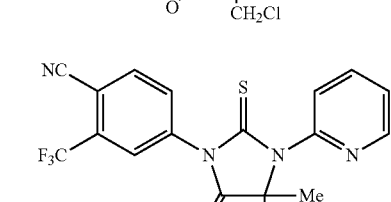 RD82
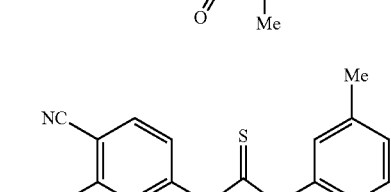 RD83
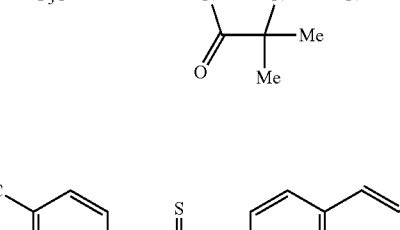 RD117
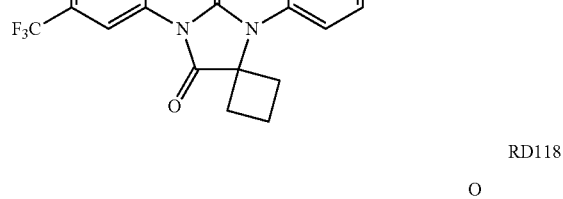 RD118

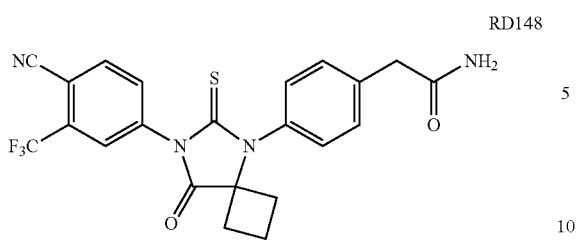
RD148
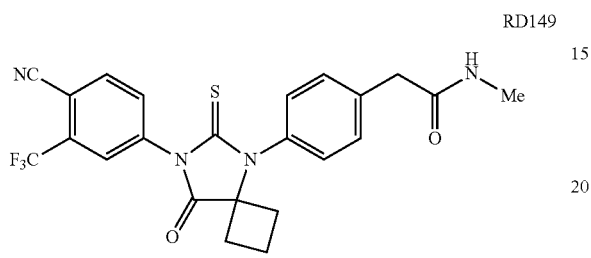
RD149
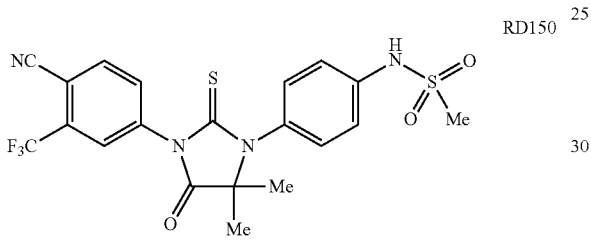
RD150
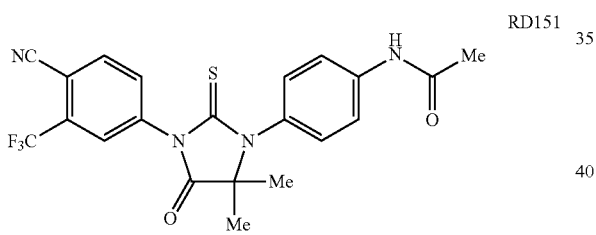
RD151
In some embodiments the compound is a compound selected from:
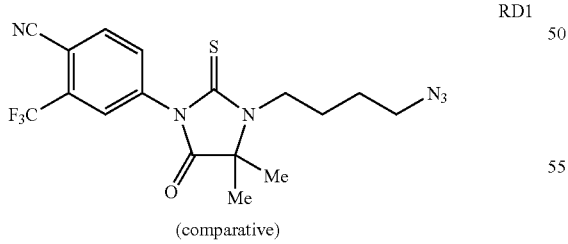
RD1
(comparative)
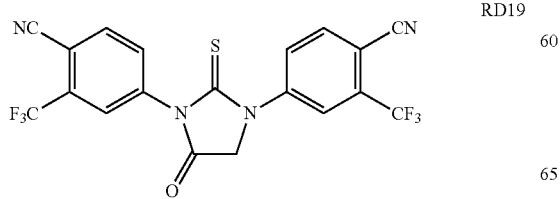
RD19
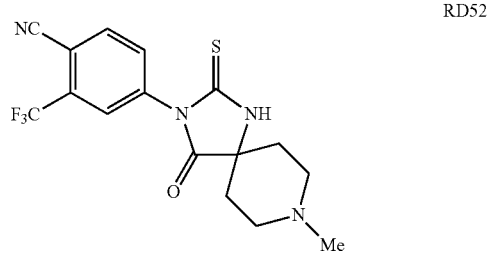
RD52
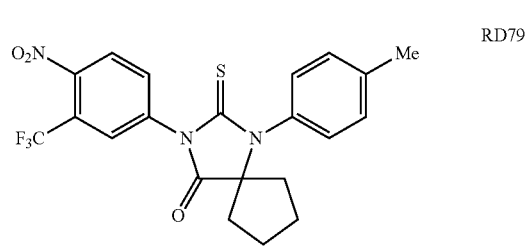
RD79
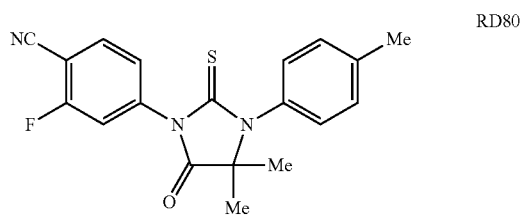
RD80
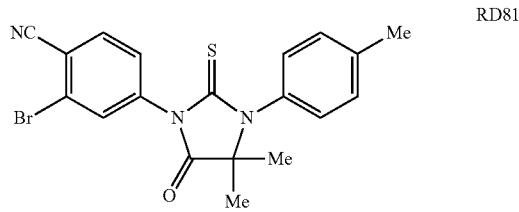
RD81
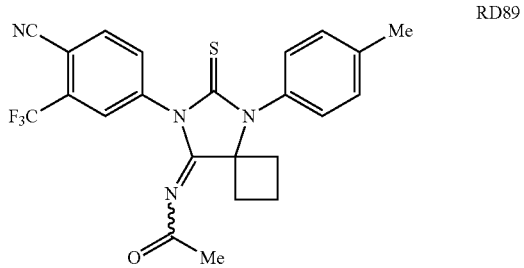
RD89
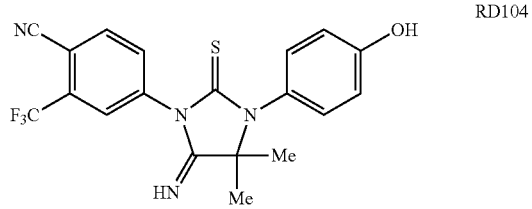
RD104

RD105
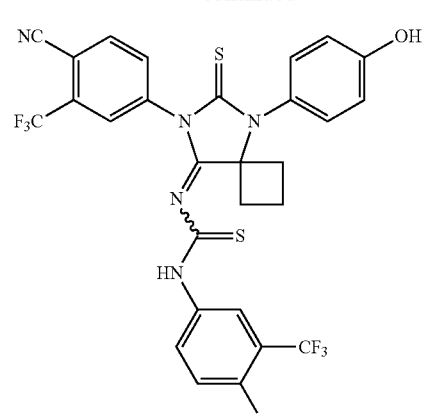
RD106
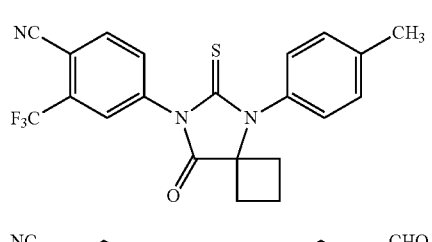
RD115
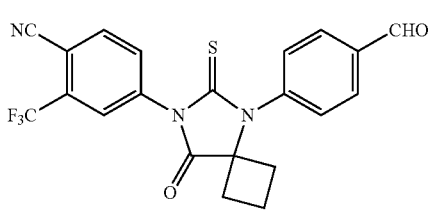
RD132
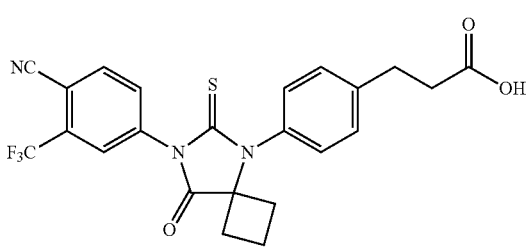
RD136
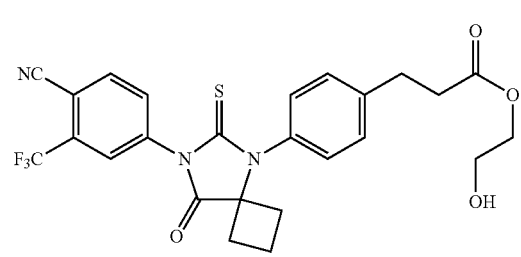
RD139
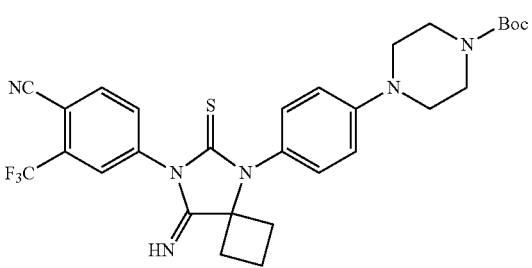
RD140
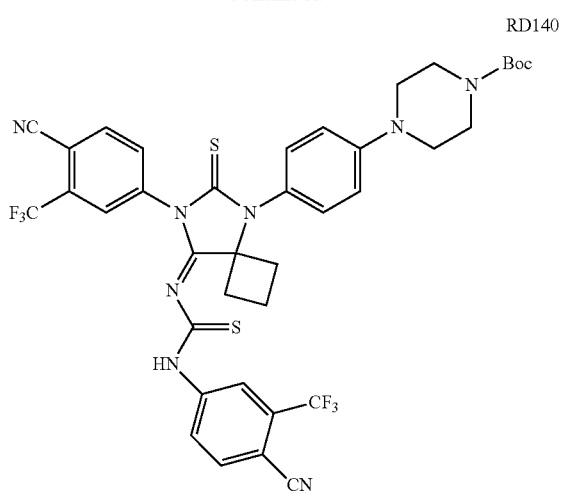
RD141
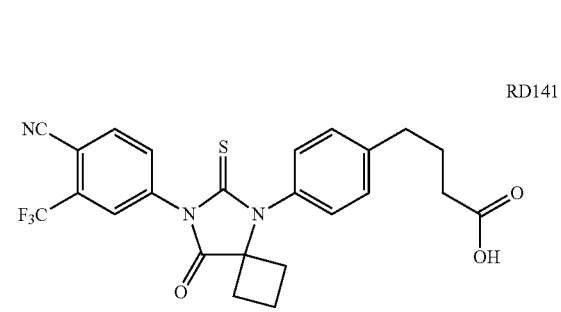
RD142
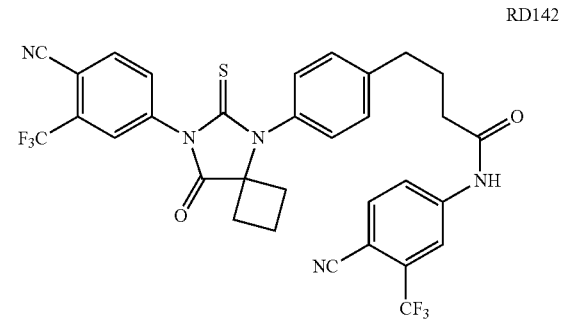
RD146
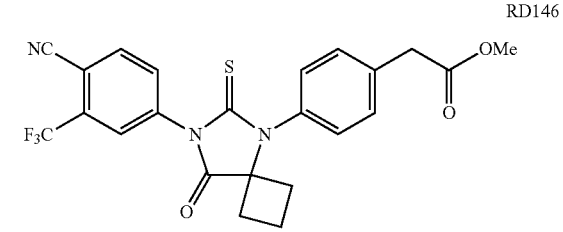
RD147
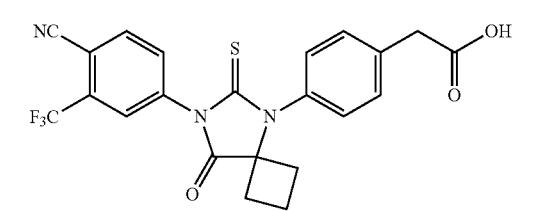

-continued

RD154

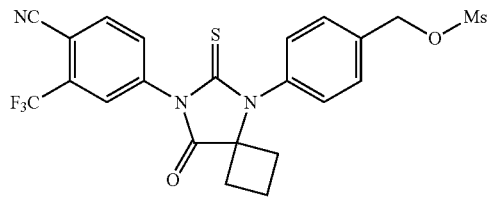

Other useful diarylhydantoin compounds and their syntheses are disclosed, for example, in U.S. 2009/0111864.

In some embodiments the compound is a compound of Formula I-E:

(I-E)

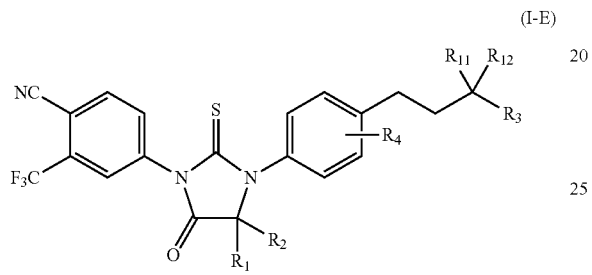

wherein $R_1$ and $R_2$ together include eight or fewer carbon atoms and are selected from the group consisting of alkyl, substituted alkyl, and, together with the carbon to which they are linked, a cycloalkyl or substituted cycloalkyl group. $R_3$ is hydrogen, cyano, formyl,

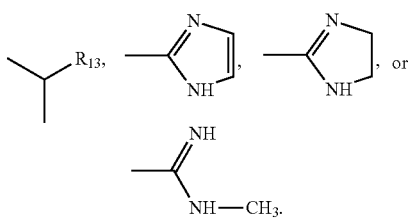 or $R_4$ is hydrogen, F, Cl, Br, or I. $R_{11}$ and $R_{12}$ can be the same or different and are hydrogen or methyl. $R_{13}$ is hydrogen or —$NR_{14}R_{15}$. $R_{14}$ and $R_{15}$ can be the same or different and are hydrogen or methyl.

In some embodiments $R_1$ and $R_2$ can be independently methyl or, together with the carbon to which they are linked, cyclobutyl or cyclopentyl. In some embodiments $R_{11}$ and $R_{12}$ can be both hydrogen or both methyl. In some embodiments $R_{13}$ can be —NH(CH$_3$) or —N(CH$_3$)$_2$. In some embodiments, when $R_4$, $R_{11}$ and $R_{12}$ are each hydrogen and when $R_1$ and $R_2$ together with the carbon to which they are linked are cyclobutyl, then $R_3$ can be other than cyano and

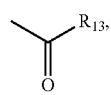

with $R_{13}$ hydrogen, —NH$_2$, —NH(CH$_3$), or —N(CH$_3$)$_2$.

Representative compounds of Formula (I)-E include:

[ND-1]

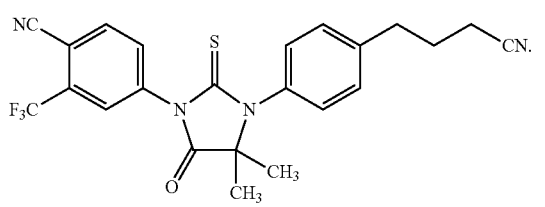

[ND-2]

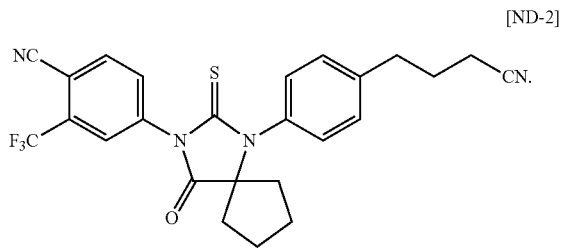

ND-3 (87)

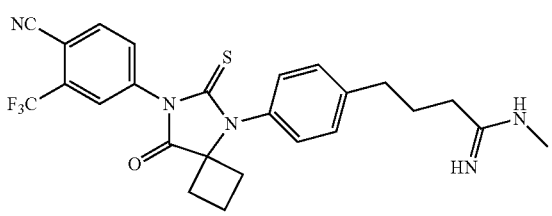

ND-6 (88)

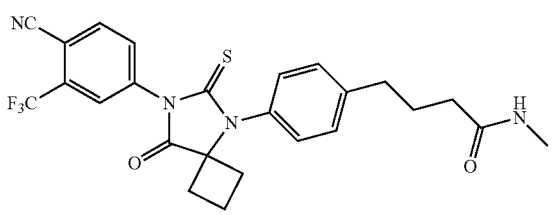

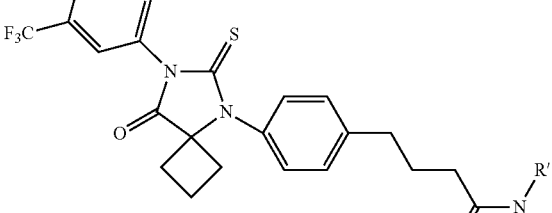

ND-7 (R = Me, R' = H), ND-8 (R = R' = Me)

ND-9 (69)

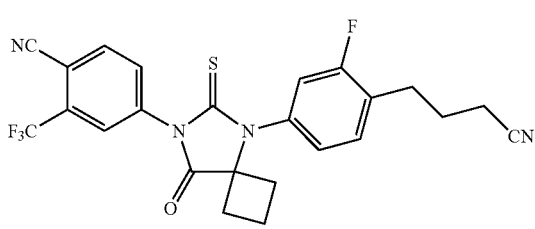

-continued

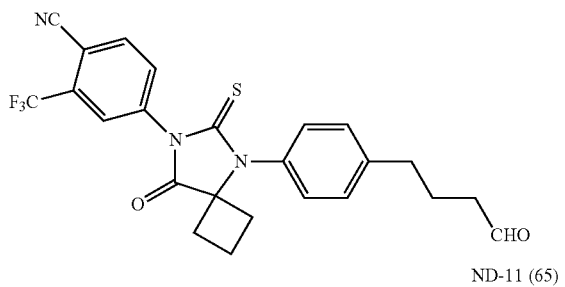
ND-10 (68)

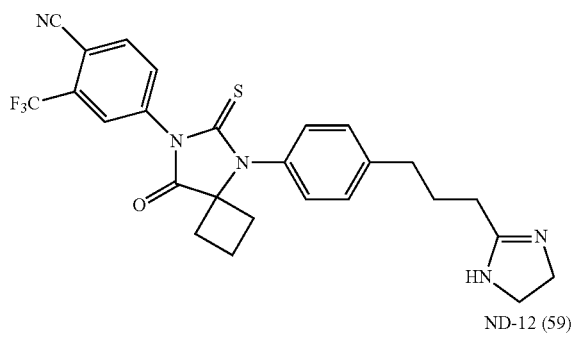
ND-11 (65)

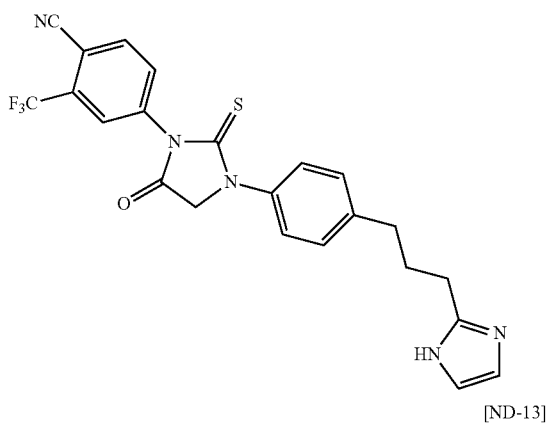
ND-12 (59)

[ND-13]

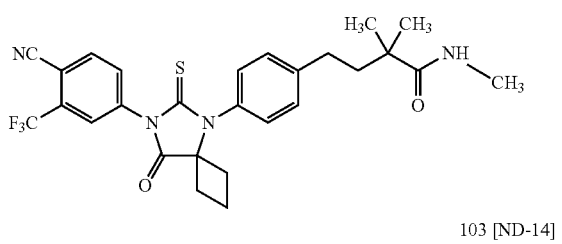
103 [ND-14]

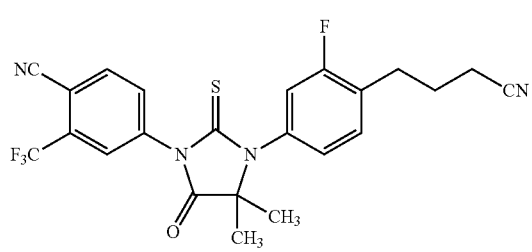

4. Hydantoin Compounds

In some embodiments the compound is a hydantoin compound. Useful hydantoin compounds and their syntheses are disclosed, for example, in US 2011/0003839.

In some embodiments a hydantoin compound is a compound of Formula II:

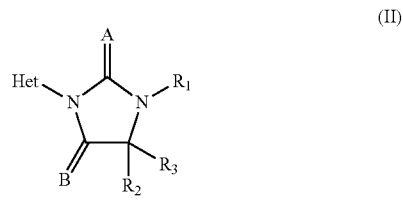
(II)

In Formula II, Het represents a heterocyclic unit of 5 or 6 atoms. A and B are independently selected from oxygen, sulfur, and N—$R_9$, with $R_9$ being selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, or $NR_{12}(CS)OR_{11}$. $R_{11}$ and $R_{12}$ are independently selected from hydrogen, alkyl, substituted alkyl, alkenyl or substituted alkenyl, alkynyl or substituted alkynyl, aryl, substituted aryl, arylalkyl, arylalkenyl, arylalkynyl, heterocyclic aromatic or non-aromatic, or substituted heterocyclic aromatic or non-aromatic. $R_1$ is selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, or $NR_{12}(CS)OR_{11}$. $R_2$ and $R_3$ are independently selected from hydrogen, aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, or substituted cycloalkyl, or, together with the carbon to which they are linked, form a cycle which can be cycloalkyl, substituted cycloalkyl, heterocyclic aromatic or non-aromatic, substituted heterocyclic aromatic or non-aromatic.

$R_2$ and $R_3$ can be connected to form a cycle which can be heterocyclic aromatic or non aromatic, substituted heterocyclic aromatic or non aromatic. $R_{11}$ and $R_{12}$ can be connected to form a cycle which can be heterocyclic aromatic or non-aromatic, substituted heterocyclic aromatic, cycloalkyl, or substituted cycloalkyl.

For example, the compound can be

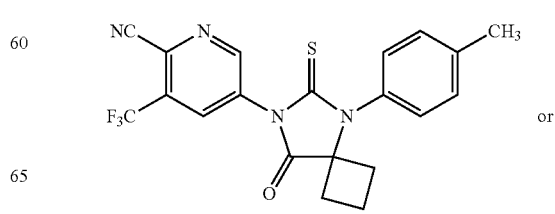
or

-continued

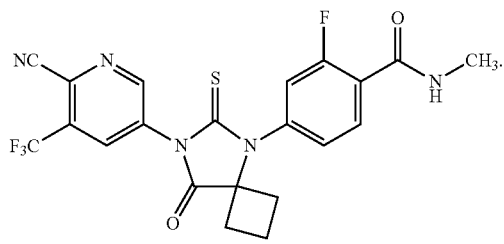

In some embodiments heterocyclic units are selected from compounds represented by the structures

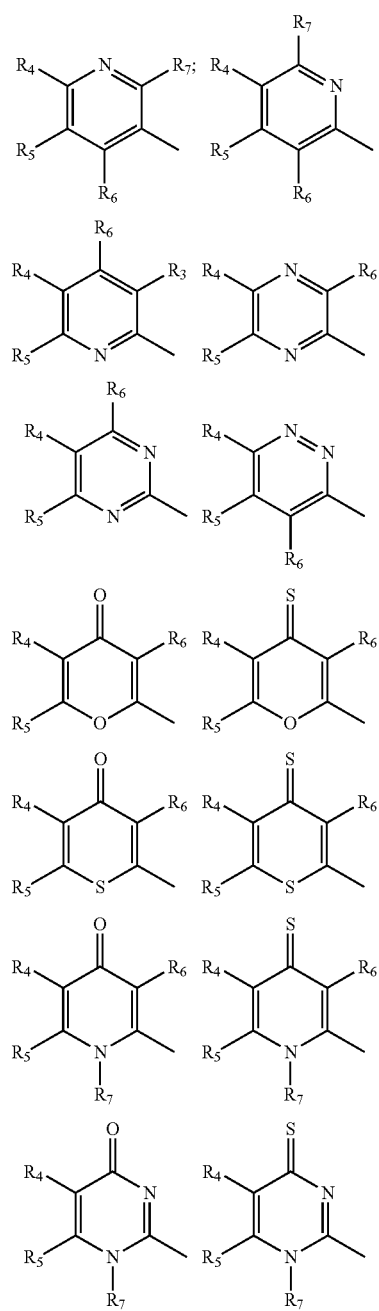

-continued

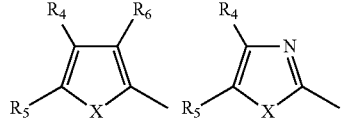

and the like. However, the hydantoins are not intended to be limited to compounds having these structures.

$R_4$, $R_5$, $R_6$, and $R_7$ are independently selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, CN, $NO_2$, $OR_{11}$, $SR_{11}$, $NR_{11}R_{12}$, $NH(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$. In some embodiments $R_4$ is CN or $NO_2$. $R_5$ is trifluoromethyl, halogenated alkyl, halogenated alkenyl, halogenated alkynyl and halogen. $R_6$ and $R_7$ are hydrogen, alkyl or halogen. $R_4$, $R_5$, $R_6$, and $R_7$ can be independently connected to form a cycle which can be aromatic, substituted aromatic, heterocyclic aromatic or non-aromatic, substituted heterocyclic aromatic or non-aromatic, cycloalkyl, substituted cycloalkyl. X is selected from sulfur (S), oxygen (O), $NR_8$ wherein N is nitrogen and is selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, $(CO)R_{11}$, $(CO)OR_{11}$, $(CS)R_{11}$, $(CS)OR_{11}$.

$R_1$ is selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$. In some embodiments $R_1$ is aryl, substituted aryl, alkyl, substituted alkyl, alkenyl, substituted alkenyl.

$R_2$ and $R_3$ are independently selected from hydrogen, aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl. $R_2$ and $R_3$ can be connected to form a cycle which can be heterocyclic aromatic or non aromatic, substituted heterocyclic aromatic or non aromatic, cycloalkyl, substituted cycloalkyl. $R_1$ and $R_2$ can be connected to form a cycle which can be heterocyclic aromatic or non aromatic, substituted heterocyclic aromatic or non aromatic.

A and B are independently selected from oxygen (O), sulfur (S) and N—$R_9$. $R_9$ is selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$.

$R_{11}$ and $R_{12}$, are independently selected from hydrogen, alkyl, substituted alkyl, alkenyl or substituted alkenyl, alkynyl or substituted alkynyl, aryl, substituted aryl, arylalkyl, arylalkenyl, arylalkynyl, heterocyclic aromatic or non-aromatic, substituted heterocyclic aromatic or non-aromatic. $R_{11}$ and $R_{12}$ can be connected to form a cycle which can be heterocyclic aromatic or non-aromatic, substituted heterocyclic aromatic, cycloalkyl, substituted cycloalkyl.

In some embodiments $R_1$ is alkyl, substituted alkyl, alkenyl, or substituted alkenyl. In some embodiments $R_1$ is selected from the group consisting of aryl and substituted aryl. In some embodiments $R_1$ is aryl substituted by at least one fluorine atom. In some embodiments $R_1$ is a 5- to 8-membered heterocyclic aromatic or non aromatic ring. In some embodiments $R_2$ and $R_3$ are independently methyl, ethyl, cyclopropyl, cyclobutyl, cyclopentyl, cyclohexyl, fluoromethyl, chloromethyl, or bromomethyl.

In some embodiments A and B are independently oxygen or sulfur.

In some embodiments Het comprises a heterocyclic unit of 6 atoms in which 1 or 2 heteroatoms independently are selected from nitrogen, oxygen, and sulfur. In some embodiments Het comprises a 0 or 1 double-bonded substituent on the heterocyclic unit selected from the group consisting of oxygen and sulfur. In some embodiments Het comprises from 3 to 4 single-bonded substituents on the heterocyclic unit selected from hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, CN, $NO_2$, $OR_{11}$, $SR_{11}$, $NR_{11}R_{12}$, $NH(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, and $NR_{12}(CS)OR_{11}$. In some embodiments a single-bonded substituent can be connected to another single-bonded substituent to form a cycle which is aromatic, substituted aromatic, heterocyclic aromatic or non-aromatic, substituted heterocyclic aromatic or non-aromatic, cycloalkyl, or substituted cycloalkyl.

In some embodiments Het is

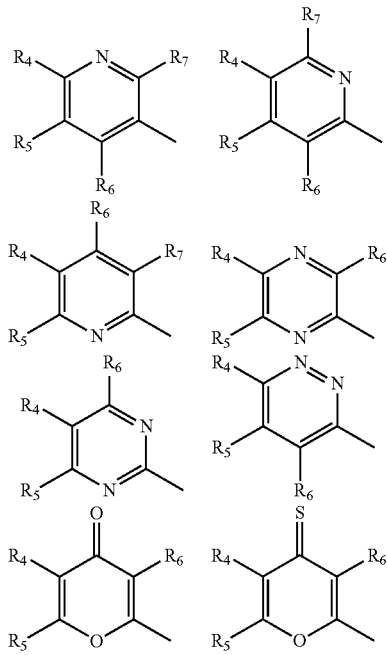

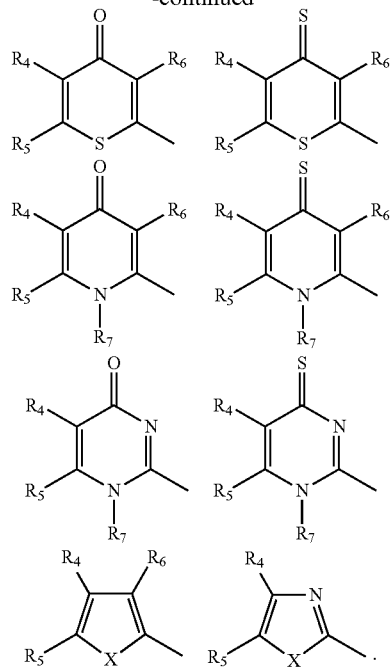

and $R_4$, $R_5$, $R_6$ and $R_7$ are independently selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, CN, $NO_2$, $OR_{11}$, $SR_{11}$, $NR_{11}R_{12}$, $NH(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$, wherein any of $R_4$, $R_5$, $R_6$ and $R_7$ can be connected to any of $R_4$, $R_5$, $R_6$ and $R_7$ to form a cycle which can be aromatic, substituted aromatic, heterocyclic aromatic or non-aromatic, substituted heterocyclic aromatic or non-aromatic, cycloalkyl, or substituted cycloalkyl.

In some embodiments $R_6$ and $R_7$ are independently selected from the group consisting of hydrogen, alkyl, and or halogen. In some embodiments $R_4$ is selected from the group consisting of CN and $NO_2$, wherein $R_5$ is selected from the group consisting of trifluoromethyl, halogenated alkyl, halogenated alkenyl, halogenated alkynyl, and halogen; in some of these embodiments $R_6$ and $R_7$ are independently selected from the group consisting of hydrogen, alkyl, and or halogen.

In some embodiments $R_4$ is CN or $NO_2$. In some embodiments $R_5$ is trifluoromethyl, halogenated alkyl, halogenated alkenyl, halogenated alkynyl, or halogen. In some embodiments $R_6$, and $R_7$ are independently hydrogen, alkyl, and or halogen.

In some embodiments $R_4$ is CN or $NO_2$ and $R_5$ is trifluoromethyl, halogenated alkyl, halogenated alkenyl, halogenated alkynyl, or halogen.

In some embodiments $R_4$ is CN or $NO_2$ and $R_6$, and $R_7$ are independently hydrogen, alkyl, and or halogen.

In some embodiments $R_4$ is CN or $NO_2$, $R_5$ is trifluoromethyl, halogenated alkyl, halogenated alkenyl, halogenated alkynyl, or halogen, and $R_6$, and $R_7$ are independently hydrogen, alkyl, and or halogen.

In some embodiments $R_5$ is trifluoromethyl, halogenated alkyl, halogenated alkenyl, halogenated alkynyl, or halogen and $R_6$, and $R_7$ are independently hydrogen, alkyl, and or halogen.

In some embodiments $R_5$ is trifluoromethyl or iodide and $R_6$ and $R_7$ are independently hydrogen or halogen.

In some embodiments Het is one of

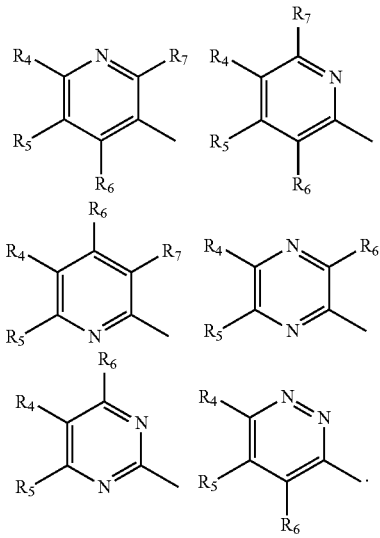

In some embodiments Het comprises a heterocyclic unit of 5 atoms, wherein the heterocyclic unit comprises 1 or 2 heteroatoms independently selected from the group consisting of sulfur, oxygen, nitrogen, and NR8, wherein $R_8$ is selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, $(CO)R_{11}$, $(CO)OR_{11}$, $(CS)R_{11}$, $(CS)OR_{11}$, wherein Het comprises from 2 to 3 single-bonded substituents on the heterocyclic unit selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, CN, $NO_2$, $OR_{11}$, $SR_{11}$, $NR_{11}R_{12}$, $NH(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$, wherein a single-bonded substituent can be connected to another single-bonded substituent to form a cycle which is aromatic, substituted aromatic, heterocyclic aromatic or non-aromatic, substituted heterocyclic aromatic or non-aromatic, cycloalkyl, or substituted cycloalkyl.

In some embodiments Het is selected from the group consisting of 5-membered rings of the compounds

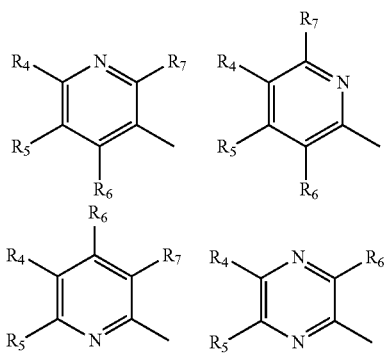

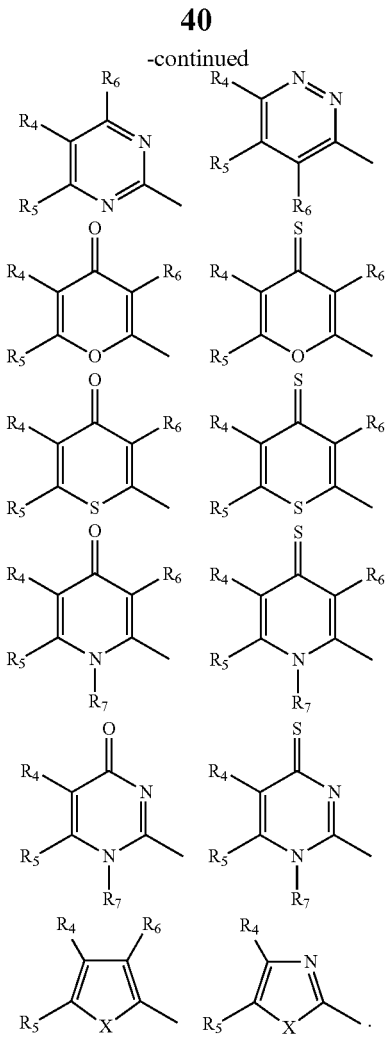

and $R_4$, $R_5$, and $R_6$, are independently selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, CN, $NO_2$, $OR_{11}$, $SR_{11}$, $NR_{11}R_{12}$, $NH(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$, wherein any of $R_4$, $R_5$, and $R_6$ can be connected to any of $R_4$, $R_5$, and $R_6$ to form a cycle which can be aromatic, substituted aromatic, heterocyclic aromatic or non-aromatic, substituted heterocyclic aromatic or non-aromatic, cycloalkyl, or substituted cycloalkyl, wherein X is selected from sulfur, oxygen, and $NR_8$, and wherein $R_8$ is selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, $(CO)R_{11}$, $(CO)OR_{11}$, $(CS)R_{11}$, and $(CS)OR_{11}$.

In some embodiments $R_4$ is selected from the group consisting of CN and $NO_2$, wherein $R_5$ is selected from the group consisting of trifluoromethyl, halogenated alkyl, halogenated alkenyl, halogenated alkynyl, and halogen, and wherein $R_6$ is selected from the group consisting of hydrogen, alkyl, and halogen.

5. Substituted Di-Arylhydantoin and Di-Arylthiohydantoin Compounds

In some embodiments the compound is a substituted di-arylhydantoin or substituted di-arylthiohydantoin compound. Useful compounds and their syntheses are disclosed, for example, in WO 2010/118354.

In some embodiments the compound is a compound of Formula III:

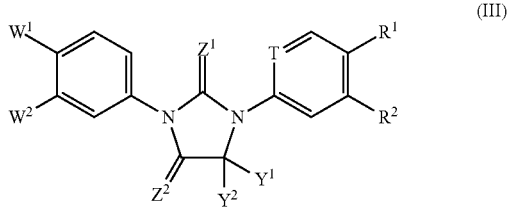

wherein:
$W^1$ is CN, $NO_2$ or $SO_2R^4$;
$W^2$ is alkyl, substituted alkyl, alkenyl, substituted alkenyl, alkynyl, substituted alkynyl or halogen;
$Z^1$ is S or O
$Z^2$ is S, O or $NR^4$;
$Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, substituted heterocyclyl or $Y^1$ and $Y^2$ are connected to form a cycle which can be heterocyclic, substituted heterocyclic, cycloalkyl, substituted cycloalkyl;
T is carbon or nitrogen and can be at any position in the ring;
$R^1$ is $—C_1-C_8$alkyl-$NR^aR^b$, $—O—C_1-C_8$alkyl-$NR^cR^d$ or $—C(O)NR^eR^f$, where:
  $R^a$ is a $C_2-C_{12}$alkyl and $R^b$ is H or a $C_1-C_{12}$alkyl or $R^a$ and $R^b$ are taken together with the N to which they are attached to form a heterocyclic ring;
  $R^c$ is a $C_1-C_{12}$alkyl and $R^e$ is H or a $C_1-C_{12}$alkyl or $R^c$ and $R^d$ are taken together with the N to which they are attached to form a heterocyclic ring;
  $R^e$ is a $C_2-C_{12}$alkyl and $R^f$ is H or a $C_1-C_{12}$alkyl, or
  $R^e$ is a $C_1-C_{12}$alkyl and $R^f$ is $C_1-C_{12}$alkyl, or
  $R^e$ and $R^f$ are taken together with the N to which they are attached to form a heterocyclic ring;
$R^2$ is hydrogen, halogen, nitro, alkyl and substituted alkyl; and
$R^4$ is independently H, alkyl, or aryl.

In some embodiments $W^1$ is CN. In some embodiments $W^2$ is alkyl, substituted alkyl, alkenyl, substituted alkenyl, alkynyl or substituted alkynyl. In some embodiments $W^2$ is substituted alkyl, substituted alkenyl or substituted alkynyl where the alkyl, alkenyl or alkynyl is substituted with a halogen. $W^2$ in some embodiments is a haloalkyl, haloalkenyl, haloalkynyl or perhaloalkyl. $W^2$ in some embodiments is a substituted alkyl. In some embodiments $W^2$ is substituted alkyl where the alkyl is substituted with a halogen. In some embodiments $W^2$ is a haloalkyl or perhaloalkyl. In some embodiments $W^2$ is a perhaloalkyl. The perhaloalkyl in some embodiments is a $C_1-C_8$ perhaloalkyl, such as trihalomethyl. In some embodiments $W^2$ is trifluoromethyl. In some embodiments $W^1$ is CN and $W^2$ is perhaloalkyl. In some embodiments $W^1$ is CN and $W^2$ is $CF_3$.

In some embodiments $Y^1$ and $Y^2$ are both a $C_1-C_8$ alkyl. In some embodiments $Y^1$ and $Y^2$ are the same $C_1-C_8$ alkyl, such as when both $Y^1$ and $Y^2$ are methyl, ethyl, propyl or butyl. In some embodiments $Y^1$ and $Y^2$ are both methyl or are taken together with the carbon to which they are attached to form a $C_4-C_5$ cycloalkyl. In some embodiments $Y^1$ and $Y^2$ are both methyl. In some embodiments at least one of $Y^1$ and $Y^2$ is alkyl where the alkyl is a cycloalkyl. In some embodiments at least one of $Y^1$ and $Y^2$ is substituted alkyl where the substituted alkyl is a substituted cycloalkyl. In some embodiments one or both of $Y^1$ and $Y^2$ are substituted alkyl, substituted alkenyl or substituted alkynyl where the alkyl, alkenyl or alkynyl is substituted with a halogen. In some embodiments at least one of $Y^1$ and $Y^2$ is a haloalkyl, haloalkenyl or haloalkynyl. In some embodiments both $Y^1$ and $Y^2$ are a haloalkyl, haloalkenyl or haloalkynyl. In some embodiments $Y^1$ and $Y^2$ are taken together with the carbon to which they are attached to form a $C_4-C_5$ cycloalkyl. In some embodiments $Y^1$ and $Y^2$ are taken together to form a cyclobutyl moiety. In some embodiments $Y^1$ and $Y^2$ are both methyl, $W^1$ is CN. In some embodiments $Y^1$ and $Y^2$ are both methyl and $W^2$ is a perhaloalkyl such as $CF_3$. In some embodiments $Y^1$ and $Y^2$ are both methyl, $W^1$ is CN and $W^2$ is a perhaloalkyl such as $CF_3$.

In some embodiments $Z^1$ and $Z^2$ are independently S or O. In some embodiments $Z^1$ is S and $Z^2$ is O. In some embodiments $Z^1$ and $Z^2$ are independently S or O and $Y^1$ and $Y^2$ are both a $C_1-C_8$ alkyl. In some embodiments $Z^1$ is S, $Z^2$ is O and $Y^1$ and $Y^2$ are the same $C_1-C_8$ alkyl. In some embodiments $Z^1$ and $Z^2$ are independently S or O and $Y^1$ and $Y^2$ are both methyl or are taken together with the carbon to which they are attached to form a $C_4-C_5$ cycloalkyl. In some embodiments $Z^1$ is S, $Z^2$ is O and the compound is further defined by one or more of the following structural features: (i) $Y^1$ and $Y^2$ are both a $C_1-C_8$ alkyl; (ii) $W^1$ is CN; (iii). $W^2$ is perhaloalkyl. In some embodiments $Z^1$ is S, $Z^2$ is O, $Y^1$ and $Y^2$ are the same $C_1-C_8$ alkyl, $W^1$ is CN and $W^2$ is $CF_3$.

In some embodiments T is C. In some embodiments T is N. In some embodiments a compound of formula (III) may be further defined by T being C. In some embodiments a compound of formula (III) may be further defined by T being N. For example, in some embodiments the compound may be further defined by T being C or by T being N.

In some embodiments $R^1$ is $—C_1-C_8$ alkyl-$NR^aR^b$ where $R^a$ is a $C_2-C_{12}$ alkyl and $R^b$ is H or a $C_1-C_{12}$ alkyl or $R^a$ and $R^b$ are taken together with the N to which they are attached to form a heterocyclic ring. In some embodiments the $—C_1-C_8$ alkyl moiety of $—C_1-C_8$ alkyl-$NR^aR^b$ is a $—(CH_2)_n$ moiety where n is an integer from 1 to 8. In some embodiments n is less than 4. In some embodiments n is 1. In some embodiments $R^a$ is a $C_2-C_{12}$ alkyl and $R^b$ is H. For example, $R^a$ in some embodiments is ethyl, propyl, butyl or pentyl and $R^b$ is H. In some embodiments $R^a$ is a $C_2-C_8$ alkyl and $R^b$ is H. In some embodiments $R^a$ is a $C_3-C_6$ alkyl and $R^b$ is H. In some embodiments $R^a$ is a $C_2-C_{12}$ alkyl and $R^b$ is a $C_1-C_{12}$ alkyl. In some embodiments $R^a$ is a $C_3-C_{12}$ cycloalkyl and $R^b$ is a $C_1-C_{12}$ alkyl (e.g., methyl). In some embodiments $R^a$ and $R^b$ are independently a $C_2-C_8$ alkyl. In some embodiments $R^a$ and $R^b$ are the same $C_2-C_{12}$ alkyl, e.g., when both $R^a$ and $R^b$ are ethyl. In some embodiments $R^a$ and $R^b$ are independently a $C_3-C_6$ alkyl. In some embodiments $R^a$ and $R^b$ are taken together with the N to which they are attached to form a heterocyclic ring. In some embodiments when $R^a$ and $R^b$ are taken together to form a heterocyclic ring, the ring is a $C_4-C_7$ heterocyclic ring. The heterocyclic ring formed by $R^a$, $R^b$ and the N to which they are attached in some embodiments contains only C and N as annular atoms. In some embodiments the heterocycle contains as annular atoms only C and the N provided when $R^a$ and $R^b$ are taken together with the N to which they are attached. In some embodiments $R^a$ and $R^b$ are taken together with the N to which they are attached to form a pyrrolidinyl or piperidinyl ring.

Where applicable, for any detailed herein wherein $R^1$ is —$C_1$-$C_8$alkyl-$NR^aR^b$, the $C_1$-$C_8$ alkyl moiety of —$C_1$-$C_8$ alkyl-$NR^aR^b$ is a —$(CH_2)_n$ moiety where n is 1. Thus, $R^1$ in some embodiments is —$CH_2NR^aR^b$ where $R^a$ and $R^b$ may be as defined herein. In some embodiments $R^1$ is:

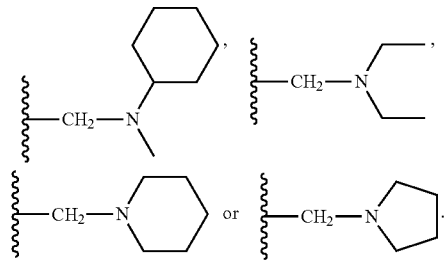

In some of these embodiments, the compound is further defined by any one or more of the following structural features: (i) $W^1$ is CN; (ii) $W^2$ is perhaloalkyl (e.g., $CF_3$); (iii) $Z^1$ is S; (iv) $Z^2$ is O; (v) $Y^1$ and $Y^2$ are both methyl and (vi) T is C.

In some embodiments $R^1$ is —O—$C_1$-$C_8$ alkyl-$NR^cR^d$ where $R^c$ is a $C_1$-$C_{12}$ alkyl and $R^d$ is H or a $C_1$-$C_{12}$ alkyl or $R^c$ and $R^d$ are taken together with the N to which they are attached to form a heterocyclic ring. In some embodiments the —$C_1$-$C_8$ alkyl moiety of —O—$C_1$-$C_8$ alkyl-$NR^cR^d$ is a —$(CH_2)_n$ moiety where n is an integer from 1 to 8. In some embodiments n is less than 4. In some embodiments n is 2. In some embodiments $R^c$ is a $C_1$-$C_{12}$alkyl and $R^d$ is H. For example, $R^c$ in some embodiments is methyl, ethyl, propyl, butyl or pentyl and $R^d$ is H. In some embodiments $R^c$ is a $C_1$-$C_8$ alkyl and $R^d$ is H. In some embodiments $R^c$ is a $C_1$-$C_4$alkyl and $R^d$ is H.

In some embodiments $R^c$ and $R^d$ are independently a $C_1$-$C_{12}$alkyl. In some of these embodiments $R^c$ and $R^d$ are the same $C_1$-$C_{12}$alkyl, e.g., when both $R^c$ and $R^d$ are methyl. In some embodiments $R^c$ and $R^d$ are independently a $C_1$-$C_8$ alkyl. In some embodiments $R^c$ and $R^d$ are independently a $C_1$-$C_4$ alkyl. In some embodiments $R^c$ and $R^d$ are taken together with the N to which they are attached to form a heterocyclic ring. In some embodiments when $R^c$ and $R^d$ are taken together to form a heterocyclic ring, the ring is a $C_4$-$C_7$ heterocyclic ring. The heterocyclic ring formed by $R^c$, $R^d$ and the N to which they are attached in some embodiments contains only C and N as annular atoms. In some embodiments the heterocycle contains as annular atoms only C and the N provided when $R^c$ and $R^d$ are taken together with the N to which they are attached. In some embodiments $R^c$ and $R^d$ are taken together with the N to which they are attached to form a pyrrolidinyl or piperidinyl ring. Where applicable, for any detailed herein wherein $R^1$ is —O—$C_1$-$C_8$ alkyl-$NR^cR^d$, the $C_1$-$C_8$ alkyl moiety of —O—$C_1$-$C_8$ alkyl-$NR^cR^d$ is a —$(CH_2)_n$ moiety where n is 2. Thus, $R^1$ in some embodiments is —$OCH_2CH_2NR^cR^d$ where $R^c$ and $R^d$ may be as defined herein. In some embodiments $R^1$ is:

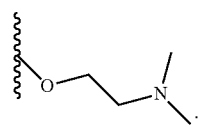 [SMILES: *OCCN(C)C]

In some of these embodiments the compound is further defined by any, one or more of the following structural features: (i) $W^1$ is CN; (ii) $W^2$ is perhaloalkyl (e.g., $CF_3$); (iii) $Z^1$ is S; (iv) $Z^2$ is O; (v) $Y^1$ and $Y^2$ are both methyl; (vi) $R^2$ is H, and (vii) T is C.

In some embodiments $R^1$ is —$C(O)NR^eR^f$ where $R^e$ and $R^f$ are as defined in provisions (i) or (ii) or (iii): (i) $R^e$ is a $C_2$-$C_{12}$alkyl and $R^f$ is H or a $C_1$-$C_{12}$alkyl; (ii) $R^e$ is a $C_1$-$C_{12}$alkyl and $R^f$ is $C_1$-$C_{12}$alkyl; or (iii) $R^e$ and $R^f$ are taken together with the N to which they are attached to form a heterocyclic ring. In some embodiments $R^1$ is —$C(O)NR^eR^f$ and $R^e$ is a $C_2$-$C_{12}$alkyl and $R^f$ is H or a $C_1$-$C_{12}$alkyl. In some embodiments $R^1$ is —$C(O)NR^eR^f$ and $R^e$ is a $C_1$-$C_{12}$alkyl and $R^f$ is $C_1$-$C_{12}$alkyl. In some embodiments $R^1$ is —$C(O)NR^eR^f$ and $R^e$ and $R^f$ are taken together with the N to which they are attached to form a heterocyclic ring. In some embodiments $R^e$ is a $C_2$-$C_{12}$ alkyl and $R^f$ is H. For example, $R^e$ in some embodiments is ethyl, propyl, butyl, pentyl or hexyl and $R^f$ is H. In some embodiments $R^e$ is a $C_3$-$C_{12}$ cycloalkyl (e.g., cyclopentyl) and $R^f$ is H. In some embodiments $R^e$ is a $C_3$-$C_{12}$ branched alkyl (e.g., tert-butyl) and $R^f$ is H. In some embodiments $R^e$ is a $C_2$-$C_8$ alkyl and $R^f$ is H. In some embodiments $R^e$ is a $C_3$-$C_6$ alkyl and $R^f$ is H. In some embodiments $R^e$ is a $C_2$-$C_{12}$ alkyl and $R^f$ is a $C_1$-$C_{12}$ alkyl (e.g., where $R^e$ is ethyl and $R^f$ is methyl). In some embodiments $R^e$ and $R^f$ are independently a $C_1$-$C_{12}$ alkyl (e.g., where both $R^e$ and $R^f$ are methyl). In some embodiments $R^e$ and $R^f$ are independently a $C_2$-$C_{12}$ alkyl. In some embodiments $R^e$ and $R^f$ are the same $C_2$-$C_{12}$alkyl, e.g., when both $R^e$ and $R^f$ are ethyl. In some embodiments $R^e$ and $R^f$ are independently a $C_2$-$C_8$ alkyl. In some embodiments $R^e$ and $R^f$ are independently a $C_3$-$C_6$ alkyl. In some embodiments at least one of $R^e$ and $R^f$ is a $C_3$-$C_6$ cycloalkyl. In some embodiments $R^e$ and $R^f$ are taken together with the N to which they are attached to form a heterocyclic ring. In some embodiments when $R^e$ and $R^f$ are taken together to form a heterocyclic ring, the ring is a $C_4$-$C_7$ heterocyclic ring. The heterocyclic ring formed by $R^e$, $R^f$ and the N to which they are attached in some embodiments contains only C and N as annular atoms. In some embodiments the heterocycle contains as annular atoms only C and the N provided when $R^e$ and $R^f$ are taken together with the N to which they are attached. In some embodiments $R^e$ and $R^f$ are taken together with the N to which they are attached to form a pyrrolidinyl or piperidinyl ring.

In some embodiments $R^1$ is:

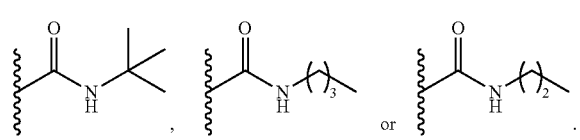

In some of these embodiments, the compound is further defined by any one or more of the following structural features: (i) $W^1$ is CN; (ii) $W^2$ is perhaloalkyl (e.g., $CF_3$); (iii) $Z^1$ is S; (iv) $Z^2$ is O; (v) $Y^1$ and $Y^2$ are both methyl and (vi) T is C.

In some embodiments $R^2$ is halo (e.g., F). In some embodiments $R^2$ is H. In some embodiments $R^2$ is halo when $R^1$ is —$C_1$-$C_8$alkyl-$NR^aR^b$ or —$C(O)NR^eR^f$. In some embodiments $R^2$ is H when $R^1$ is —O—$C_1$-$C_8$alkyl-$NR^cR^d$.

In some embodiments the compound is a compound of Formula III-A:

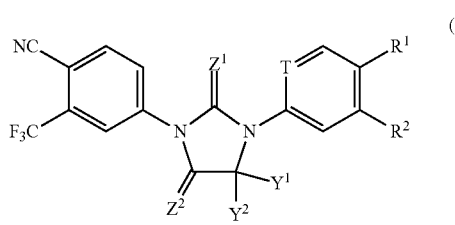

(III-A)

where $Z^1$, $Z^2$, $Y^1$, $Y^2$, T, $R^1$ and $R^2$ are as defined in formula (III) or any embodiment thereof.

In some embodiments the compound is a compound of Formula III-B:

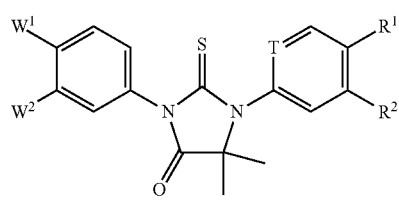

(III-B)

where $W^1$, $W^2$, T, $R^1$ and $R^2$ are as defined in formula (III) or any embodiment thereof.

In some embodiments the compound is a compound of Formula III-C:

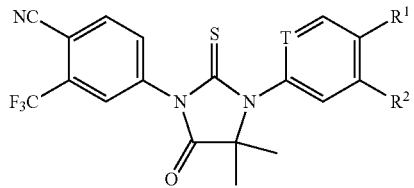

(III-C)

where T, $R^1$ and $R^2$ are as defined in formula (III) or any embodiment thereof.

In some embodiments the compound is a compound of Formula III-D:

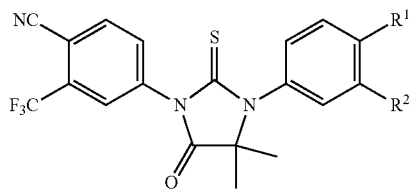

(III-D)

where $R^1$ and $R^2$ are as defined in formula (III) or any embodiment thereof.

In some embodiments the compound is a compound of Formula III-E:

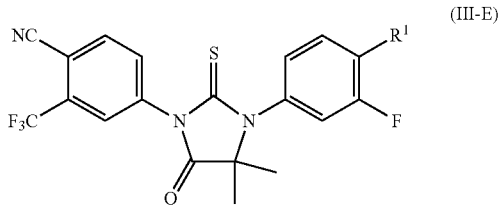

(III-E)

where $R^1$ is as defined in formula (III) or any embodiment thereof.

In some embodiments the compound is a compound of Formula III-F:

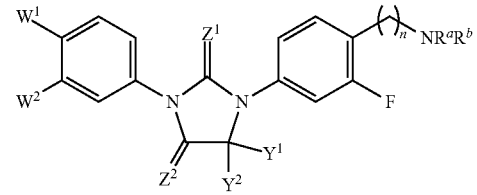

(III-F)

where n is an integer from 1 to 8 and $W^1$, $W^2$, $Z^1$, $Z^2$, $Y^2$, $Y^1$, $R^a$ and $R^b$ are as defined in formula (III) or any embodiment thereof.

In some embodiments the compound is a compound of Formula III-G:

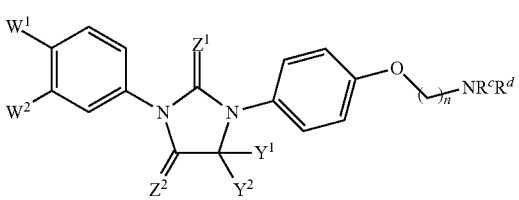

(III-G)

where n is an integer from 1 to 8 and $W^1$, $W^2$, $Z^1$, $Z^2$, $Y^1$, $R^c$ and $R^d$ are as defined in formula (III) or any embodiment thereof.

In some embodiments the compound is a compound of Formula III-H:

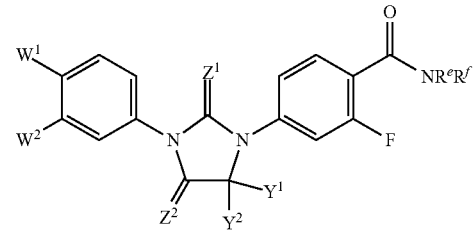

(III-H)

where $W^1$, $W^2$, $Z^1$, $Z^2$, $Y^2$, $Y^1$, $R^e$ and $R^f$ are as defined in formula (III) or any embodiment thereof.

Examples of compounds according to Formula III are depicted in Table 1. The compounds depicted may be present as salts even if salts are not depicted and it is understood that the this disclosure embraces all salts and solvates of the compounds depicted here, as well as the non-salt and non-solvate form of the compound, as is well understood by the skilled artisan. It is thus understood that pharmaceutically acceptable salts of compounds are intended.

TABLE 1

Representative Compounds of Formula III.

| Structure | Compound No. |
|---|---|
| 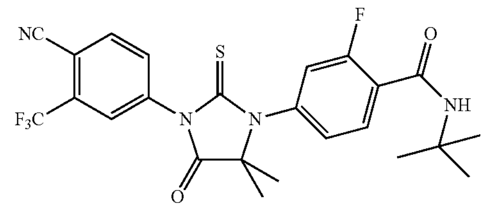 [SMILES: CC(C)(C)NC(=O)c1ccc(N2C(=S)N(c3ccc(C#N)c(C(F)(F)F)c3)C(=O)C2(C)C)cc1F] | 1 |
| 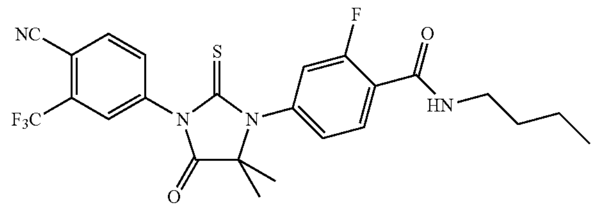 [SMILES: CCCCNC(=O)c1ccc(N2C(=S)N(c3ccc(C#N)c(C(F)(F)F)c3)C(=O)C2(C)C)cc1F] | 2 |
| 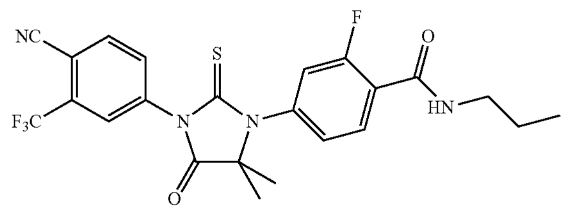 [SMILES: CCCNC(=O)c1ccc(N2C(=S)N(c3ccc(C#N)c(C(F)(F)F)c3)C(=O)C2(C)C)cc1F] | 3 |
| 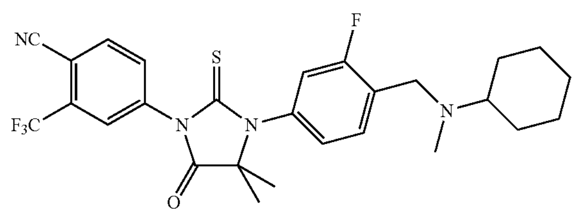 [SMILES: CN(Cc1ccc(N2C(=S)N(c3ccc(C#N)c(C(F)(F)F)c3)C(=O)C2(C)C)cc1F)C1CCCCC1] | 4 |
| 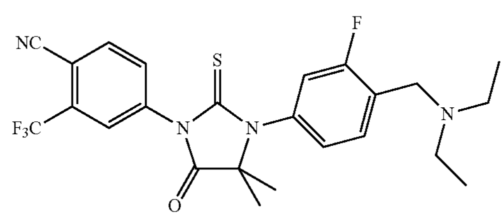 [SMILES: CCN(CC)Cc1ccc(N2C(=S)N(c3ccc(C#N)c(C(F)(F)F)c3)C(=O)C2(C)C)cc1F] | 5 |
| 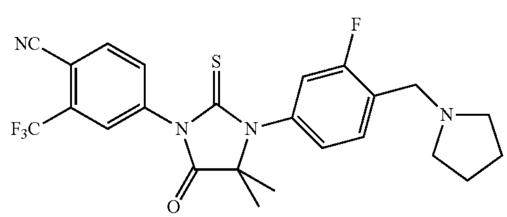 [SMILES: CC1(C)C(=O)N(c2ccc(C#N)c(C(F)(F)F)c2)C(=S)N1c1ccc(CN2CCCC2)c(F)c1] | 6 |

TABLE 1-continued

Representative Compounds of Formula III.

| Structure | Compound No. |
| --- | --- |
| ![Compound 7 structure: NC and F3C substituted phenyl attached to thioxo-imidazolidinone with dimethyl, connected to N-phenyl with F and CH2-piperidine] | 7 |
| ![Compound 8 structure: NC and F3C substituted phenyl attached to thioxo-imidazolidinone with dimethyl, connected to N-phenyl with C(O)NH-propyl] | 8 |

6. Substituted Phenylcarbamoyl Alkylamino Arene and N,N'-Bis-Arylurea Compounds

In some embodiments the compound is a substituted phenylcarbamoyl alkylamino arene or an N,N'-bis-arylurea compound. Other useful compounds and their syntheses are disclosed in WO 2011/044327. In some embodiments a compound is a compound of Formula IV:

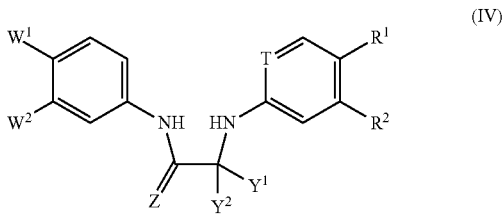

(IV)

wherein:
$W^1$ is CN, $NO_2$ or $SO_2R^4$;
$W^2$ is alkyl, substituted alkyl, alkenyl, substituted alkenyl, alkynyl, substituted alkynyl or halogen;
Z is S, O or $NR^5$;
$Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, substituted heterocyclyl or $Y^1$ and $Y^2$ are taken together with the carbon to which they are attached to form a cycle which can be heterocyclic, substituted heterocyclic, cycloalkyl, substituted cycloalkyl;
T is carbon or nitrogen and can be at any position in the ring;
$R^1$ is —$C_1$-$C_8$ alkyl-$NR^aR^b$, —O—$C_1$-$C_8$ alkyl-$NR^cR^d$ or —$C(O)NR^eR^f$,
where:
$R^a$ is a $C_1$-$C_{12}$ alkyl and $R^b$ is H or a $C_1$-$C_{12}$ alkyl or $R^a$ and $R^b$ are taken together with the N to which they are attached to form a heterocyclic ring;
$R^c$ is a $C_1$-$C_{12}$ alkyl and $R^d$ is H or a $C_1$-$C_{12}$ alkyl or $R^c$ and $R^d$ are taken together with the N to which they are attached to form a heterocyclic ring;
$R^e$ is a $C_1$-$C_{12}$ alkyl and $R^f$ is H or a $C_1$-$C_{12}$ alkyl, or $R^e$ and $R^f$ are taken together with the N to which they are attached to form a heterocyclic ring;

$R^2$ is hydrogen, halogen, nitro, alkyl or substituted alkyl;
$R^4$ is H, alkyl, substituted alkyl, aryl or substituted aryl; and
$R^5$ is H, alkyl, substituted alkyl, aryl or substituted aryl.

In some embodiments the salt is a pharmaceutically acceptable salt.

In some embodiments the compound is of the formula (IV) where $W^1$ is CN. In some embodiments $W^2$ is alkyl, substituted alkyl, alkenyl, substituted alkenyl, alkynyl or substituted alkynyl. In some embodiments $W^2$ is substituted alkyl, substituted alkenyl or substituted alkynyl where the alkyl, alkenyl or alkynyl is substituted with one or more halogens. $W^2$ in some embodiments is a haloalkyl, haloalkenyl, haloalkynyl or perhaloalkyl. $W^2$ in some embodiments is a substituted alkyl. In some embodiments $W^2$ is substituted alkyl where the alkyl is substituted with one or more halogens. In some embodiments $W^2$ is a haloalkyl or perhaloalkyl. In some embodiments $W^2$ is a perhaloalkyl. The perhaloalkyl in some embodiments is a $C_1$-$C_8$ perhaloalkyl, such as trihalomethyl. In some embodiments $W^2$ is trifluoromethyl. In a particular, $W^1$ is CN and $W^2$ is perhaloalkyl. In another particular, $W^1$ is CN and $W^2$ is $CF_3$.

In some embodiments $Y^1$ and $Y^2$ are both a $C_1$-$C_8$ alkyl. In some embodiments $Y^1$ and $Y^2$ are the same $C_1$-$C_8$ alkyl, such as when both $Y^1$ and $Y^2$ are methyl, ethyl, propyl or butyl. In some embodiments $Y^1$ and $Y^2$ are both methyl or are taken together with the carbon to which they are attached to form a $C_3$-$C_5$ cycloalkyl. In some embodiments $Y^1$ and $Y^2$ are both methyl. In some embodiments one of $Y^1$ or $Y^2$ is hydrogen and the other of $Y^1$ or $Y^2$ is $C_1$-$C_8$ alkyl. In some embodiments one of $Y^1$ or $Y^2$ is hydrogen and the other of $Y^1$ or $Y^2$ is methyl, ethyl, propyl or butyl. In some embodiments at least one of $Y^1$ and $Y^2$ is alkyl where the alkyl is a cycloalkyl. In some embodiments at least one of $Y^1$ and $Y^2$ is substituted alkyl where the substituted alkyl is a substituted cycloalkyl. In some embodiments one or both of $Y^1$ and $Y^2$ are substituted alkyl, substituted alkenyl or substituted alkynyl where the alkyl, alkenyl or alkynyl is substituted with one or more halogens. In some embodiments at least one of $Y^1$ and $Y^2$ is a haloalkyl, haloalkenyl or haloalkynyl. In some embodiments both $Y^1$ and $Y^2$ are a haloalkyl, haloalkenyl or haloalkynyl. In some embodiments $Y^1$ and $Y^2$ are taken together with the carbon to which they are attached to form a $C_3$-$C_5$ cycloalkyl. In some embodiments $Y^1$ and $Y^2$ are taken together with the carbon to which they are attached to form a cyclopropyl, cyclobutyl or cyclopentyl moiety. In some embodiments $Y^1$ and $Y^2$ are both methyl and $W^1$ is CN. In some embodiments $Y^1$ and $Y^2$ are both methyl and $W^2$ is a perhaloalkyl such as $CF_3$. In some embodiments $Y^1$ and $Y^2$ are both methyl, $W^1$ is CN and $W^2$ is a perhaloalkyl such as $CF_3$. In some embodiments $Y^1$ is isopropyl, $Y^2$ is H, $W^1$ is CN and $W^2$ is a perhaloalkyl such as $CF_3$. In a particular, $Y^1$ and $Y^2$ are taken together with the carbon to which they are attached to form a cyclopropyl, $W^1$ is CN. In another particular of formula (IV), $Y^1$ and $Y^2$ are taken together with the carbon to which they are attached to form a cyclopropyl and $W^2$ is a perhaloalkyl such as $CF_3$. In some embodiments $Y^1$ and $Y^2$ are taken together with the carbon to which they are attached to form a cyclopropyl, $W^1$ is CN and $W^2$ is a perhaloalkyl such as $CF_3$.

In some embodiments Z is substituted N (e. g., $NR^5$), S or O. In some embodiments Z is O. In a particular, Z is S or O and $Y^1$ and $Y^2$ are both a $C_1$-$C_8$ alkyl. In some embodiments Z is O and $Y^1$ and $Y^2$ are the same $C_1$-$C_8$ alkyl. In some embodiments Z is S or O and $Y^1$ and $Y^2$ are both methyl or are taken together with the carbon to which they are attached to form a $C_3$-$C_5$ cycloalkyl. In some embodiments Z is O and the compound is further defined by one or more of the following structural features: (i) $Y^1$ and $Y^2$ are both a $C_1$-$C_8$ alkyl; (ii) $W^1$ is CN; (iii) $W^2$ is perhaloalkyl. In some embodiments Z is O, $Y^1$ and $Y^2$ are the same $C_1$-$C_8$ alkyl, $W^1$ is CN and $W^2$ is $CF_3$. In one particular such embodiment Z is O, $Y^1$ and $Y^2$ are each methyl, $W^1$ is CN and $W^2$ is $CF_3$. In some embodiments the compounds of formula (IV) are provided where Z is O and the compound is further defined by one or more of the following structural features: (i) $Y^1$ and $Y^2$ are taken together with the carbon to which they are attached to form a $C_3$-$C_5$ cycloalkyl; (ii) $W^1$ is CN; (iii) $W^2$ is perhaloalkyl. In some embodiments Z is O, $Y^1$ and $Y^2$ are taken together with the carbon to which they are attached to form a $C_3$-$C_5$ cycloalkyl, $W^1$ is CN and $W^2$ is $CF_3$. In one particular embodiment Z is O, $Y^1$ and $Y^2$ are taken together with the carbon to which they are attached to form a cyclopropyl, $W^1$ is CN and $W^2$ is $CF_3$.

In some embodiments T is C. In some embodiments T is N. It is understood that where applicable, a compound may be further defined by T being C. It is understood that where applicable, a compound may be further defined by T being N. For example, the embodiments described herein may in some cases be further defined by T being C or by T being N.

Compounds of formula (IV) are provided where $R^1$ is —$C_1$-$C_8$ alkyl-$NR^aR^b$ where $R^a$ is a $C_1$-$C_{12}$ alkyl and $R^b$ is H or a $C_1$-$C_{12}$ alkyl or $R^a$ and $R^b$ are taken together with the N to which they are attached to form a heterocyclic ring. In some embodiments the —$C_1$-$C_8$ alkyl moiety of —$C_1$-$C_8$ alkyl-$NR^aR^b$ is a —$(CH_2)_n$ moiety where n is an integer from 1 to 8. In some embodiments n is less than 4. In some embodiments n is 1. In some embodiments $R^a$ is a $C_1$-$C_{12}$ alkyl and $R^b$ is H. For example, $R^a$ in some embodiments is methyl, ethyl, propyl, butyl or pentyl and $R^b$ is H. In some embodiments $R^a$ is a $C_1$-$C_8$ alkyl and $R^b$ is H. In some embodiments $R^a$ is a $C_3$-$C_6$ alkyl and $R^b$ is H. Compounds of formula (IV) are also provided where $R^a$ is a $C_1$-$C_{12}$ alkyl and $R^b$ is a $C_1$-$C_{12}$ alkyl. In some embodiments $R^a$ is a $C_3$-$C_{12}$ cycloalkyl and $R^b$ is a $C_1$-$C_{12}$ alkyl (e.g., methyl). In some embodiments $R^a$ and $R^b$ are independently a $C_1$-$C_8$ alkyl. In some embodiments $R^a$ and $R^b$ are the same $C_1$-$C_{12}$ alkyl, e.g., when both $R^a$ and $R^b$ are ethyl. In some embodiments $R^a$ and $R^b$ are independently a $C_3$-$C_6$ alkyl. In still some embodiments $R^a$ and $R^b$ are taken together with the N to which they are attached to form a heterocyclic ring. In some embodiments when $R^a$ and $R^b$ are taken together to form a heterocyclic ring, the ring is a 4- to 7-membered heterocyclic ring. The heterocyclic ring formed by $R^a$, $R^b$ and the N to which they are attached in some embodiments contains only C and N as annular atoms. In some embodiments the heterocycle contains as annular atoms only C and the N provided when $R^a$ and $R^b$ are taken together with the N to which they are attached. In a particular, $R^a$ and $R^b$ are taken together with the N to which they are attached to form a pyrrolidinyl or piperidinyl ring. Where applicable, for any detailed herein wherein $R^1$ is —$C_1$-$C_8$ alkyl-$NR^aR^b$, in some embodiments the $C_1$-$C_8$ alkyl moiety of —$C_1$-$C_8$ alkyl-$NR^aR^b$ is a —$(CH_2)_n$ moiety where n is 1. Thus, $R^1$ in some embodiments is —$CH_2NR^aR^b$ where $R^a$ and $R^b$ may be as defined herein. In some embodiments $R^1$ is:

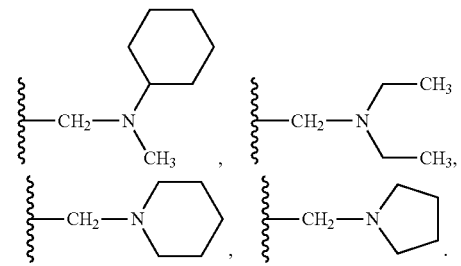

In some of these embodiments, the compound is further defined by any one or more of the following structural features: (i) $W^1$ is CN; (ii) $W^2$ is perhaloalkyl (e.g., $CF_3$); (iii) Z is O; (iv) $Y^1$ and $Y^2$ are both methyl and (v) T is C. In some embodiments the compound is further defined by any one or more of the following structural features: (i) $W^1$ is CN; (ii) $W^2$ is perhaloalkyl (e.g., $CF_3$); (iii) Z is O; (iv) $Y^1$ and $Y^2$ are both methyl, (v) $R^2$ is halogen (e.g., F) and (vi) T is C.

Compounds of formula (IV) are provided where $R^1$ is —O—$C_1$-$C_8$ alkyl-$NR^cR^d$ where $R^c$ is a $C_1$-$C_{12}$ alkyl and $R^d$ is H or a $C_1$-$C_{12}$ alkyl or $R^c$ and $R^d$ are taken together with the N to which they are attached to form a heterocyclic ring. In some embodiments the —$C_1$-$C_8$ alkyl moiety of —O—$C_1$-$C_8$ alkyl-$NR^cR^d$ is a —$(CH_2)_n$ moiety where n is an integer from 1 to 8. In some embodiments n is less than 4. In some embodiments n is 2. In some embodiments $R^c$ is a $C_1$-$C_{12}$ alkyl and $R^d$ is H. For example, $R^c$ in some embodiments is methyl, ethyl, propyl, butyl or pentyl and $R^d$ is H. In some embodiments $R^c$ is a $C_1$-$C_8$ alkyl and $R^d$ is H. In some embodiments $R^c$ is a $C_1$-$C_4$ alkyl and $R^d$ is H. Compounds of formula (IV) are also provided where $R^c$ and $R^d$ are independently a $C_1$-$C_{12}$ alkyl. In some embodiments $R^c$ and $R^d$ are the same $C_1$-$C_{12}$ alkyl, e.g., when both $R^c$ and $R^d$ are methyl. In some embodiments $R^c$ and $R^d$ are independently a $C_1$-$C_8$ alkyl. In some embodiments $R^c$ and $R^d$ are independently a $C_1$-$C_4$ alkyl. In still some embodiments $R^c$ and $R^d$ are taken together with the N to which they are attached to form a heterocyclic ring. In some embodiments when $R^c$ and $R^d$ are taken together to form a heterocyclic ring, the ring is a 4- to 7-membered heterocyclic ring. The heterocyclic ring formed by $R^c$, $R^d$ and the N to which they are attached in some embodiments contains only C and N as annular atoms. In some embodiments the heterocycle contains as annular atoms only C and the N provided when $R^c$ and $R^d$ are taken together with the N to which they are attached. In a particular, $R^c$ and $R^d$ are taken together with the N to which they are attached to form a pyrrolidinyl or piperidinyl ring. Where applicable, for any detailed herein wherein $R^1$ is —O—$C_1$-$C_8$ alkyl-$NR^cR^d$, in some embodiments the $C_1$-$C_8$ alkyl moiety of —O—$C_1$-$C_8$ alkyl-$NR^cR^d$ is a —$(CH_2)_n$— moiety where n is 2. Thus, $R^1$ in some embodiments is —$OCH_2CH_2NR^cR^d$ where $R^c$ and $R^d$ may be as defined herein.

In some embodiments $R^1$ is:

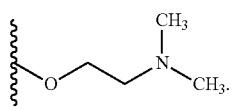

In some of these embodiments the compound is further defined by any one or more of the following structural features: (i) $W^1$ is CN; (ii) $W^2$ is perhaloalkyl (e.g., $CF_3$); (iii) Z is O; (iv) $Y^1$ and $Y^2$ are both methyl; (v) $R^2$ is H, and (vi) T is C.

In some embodiments $R^1$ is —$C(O)NR^eR^f$ where $R^e$ and $R^f$ are as defined in provisions (i) or (ii) or (iii) or (iv): (i) $R^e$ and $R^f$ are independently H or a $C_1$-$C_{12}$ alkyl; (ii) $R^e$ is a $C_1$-$C_{12}$ alkyl and $R^f$ is H or a $C_1$-$C_{12}$ alkyl; (iii) $R^e$ is a $C_1$-$C_{12}$ alkyl and $R^f$ is $C_1$-$C_{12}$ alkyl; or (iv) $R^e$ and $R^f$ are taken together with the N to which they are attached to form a heterocyclic ring. In some embodiments $R^1$ is —$C(O)NR^eR^f$ and $R^e$ and $R^f$ are independently H or a $C_1$-$C_{12}$ alkyl. In some embodiments $R^1$ is —$C(O)NR^eR^f$ and $R^e$ is a $C_1$-$C_{12}$ alkyl and $R^f$ is H or a $C_1$-$C_{12}$ alkyl. In some embodiments $R^1$ is —$C(O)NR^eR^f$ and $R^e$ is a $C_1$-$C_{12}$ alkyl and $R^f$ is $C_1$-$C_{12}$ alkyl. In some embodiments $R^1$ is —$C(O)NR^eR^f$ and $R^e$ and $R^f$ are taken together with the N to which they are attached to form a heterocyclic ring. In some embodiments $R^e$ is a $C_1$-$C_{12}$ alkyl and $R^f$ is H. For example, $R^e$ in some embodiments is methyl, ethyl, propyl, butyl, pentyl or hexyl and $R^f$ is H. In some embodiments $R^e$ is a $C_3$-$C_{12}$ cycloalkyl (e.g., cyclopentyl) and $R^f$ is H. In some embodiments $R^e$ is a $C_3$-$C_{12}$ branched alkyl (e.g., tert-butyl) and $R^f$ is H. In some embodiments $R^e$ is a $C_1$-$C_8$ alkyl and $R^f$ is H (e.g., where $R^e$ is methyl and $R^f$ is H). In some embodiments $R^e$ is a $C_3$-$C_6$ alkyl and $R^f$ is H (e.g., where $R^e$ is propyl or butyl and $R^f$ is H). In some embodiments $R^e$ is a $C_1$-$C_{12}$ alkyl and $R^f$ is a $C_1$-$C_{12}$ alkyl (e.g., where $R^e$ is ethyl and $R^f$ is methyl). In some embodiments $R^e$ and $R^f$ are independently a $C_1$-$C_{12}$ alkyl (e.g., where both $R^e$ and $R^f$ are methyl). In some embodiments $R^e$ and $R^f$ are independently a $C_1$-$C_{12}$ alkyl. In some embodiments $R^e$ and $R^f$ are the same $C_1$-$C_{12}$ alkyl, e.g., when both $R^e$ and $R^f$ are ethyl. In some embodiments $R^e$ and $R^f$ are independently a $C_1$-$C_8$ alkyl. In some embodiments $R^e$ and $R^f$ are independently a $C_3$-$C_6$ alkyl. In some embodiments at least one of $R^e$ and $R^f$ is a $C_3$-$C_6$ cycloalkyl. In still some embodiments $R^e$ and $R^f$ are taken together with the N to which they are attached to form a heterocyclic ring. In some embodiments when $R^e$ and $R^f$ are taken together to form a heterocyclic ring, the ring is a 4- to 7-membered heterocyclic ring. The heterocyclic ring formed by $R^e$, $R^f$ and the N to which they are attached in some embodiments contains only C and N as annular atoms. In some embodiments the heterocycle contains as annular atoms only C and the N provided when $R^e$ and $R^f$ are taken together with the N to which they are attached. In a particular, $R^e$ and $R^f$ are taken together with the N to which they are attached to form a pyrrolidinyl or piperidinyl ring. In some embodiments $R^1$ is:

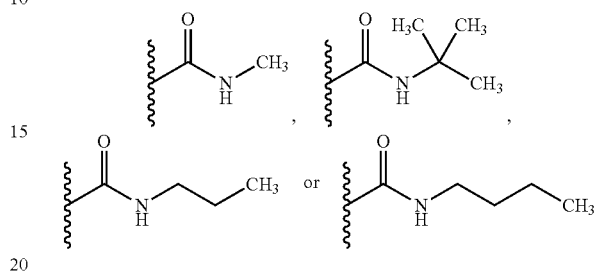

In some embodiments the compound is further defined by any one or more of the following structural features: (i) $W^1$ is CN; (ii) $W^2$ is perhaloalkyl (e.g., $CF_3$); (iii) Z is O; (iv) $Y^1$ and $Y^2$ are both methyl and (vi) T is C. In some embodiments $R^1$ is as defined above and the compound is further defined by any one or more of the following structural features: (i) $W^1$ is CN; (ii) $W^2$ is perhaloalkyl (e.g., $CF_3$); (iii) Z is O; (iv) $Y^1$ and $Y^2$ are taken together with the carbon to which they are attached to form a cyclopropyl and (vi) T is C.

In any embodiment detailed herein, $R^2$ in some embodiments is halo (e.g., F). In some embodiments $R^2$ is H. In some embodiments $R^2$ is halo when $R^1$ is —$C_1$-$C_8$ alkyl-$NR^aR^b$ or —$C(O)NR^eR^f$. In some embodiments $R^2$ is H when $R^1$ is —O—$C_1$-$C_8$ alkyl-$NR^cR^d$.

In some embodiments the compound is a compound of Formula IV-A:

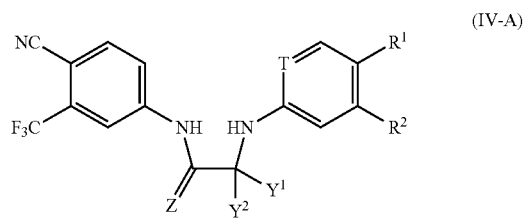

where Z, $Y^1$, $Y^2$, T, $R^1$ and $R^2$ are as defined in formula (IV) or any embodiment thereof.

In some embodiments the compound is a compound of Formula IV-B:

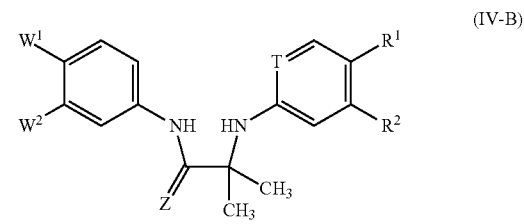

where $W^1$, $W^2$, T, $R^1$ and $R^2$ are as defined in formula (IV) or any embodiment thereof.

In some embodiments the compound is a compound of Formula IV-C:

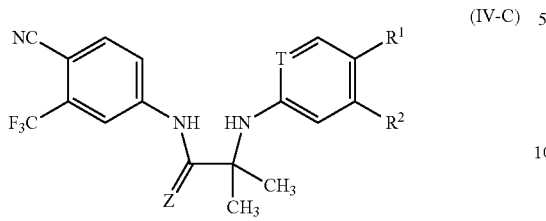

where T, R¹ and R² are as defined in formula (IV) or any embodiment thereof.

In some embodiments the compound is a compound of Formula IV-D:

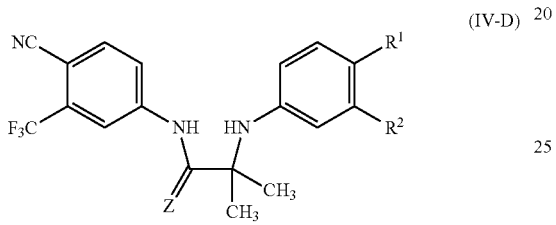

where R¹ and R² are as defined in formula (IV) or any embodiment thereof.

In some embodiments the compound is a compound of Formula IV-E:

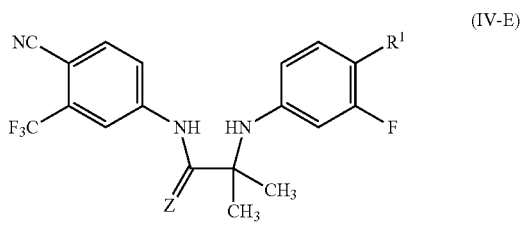

where R¹ is as defined in formula (IV) or any embodiment thereof.

In some embodiments the compound is a compound of Formula IV-F:

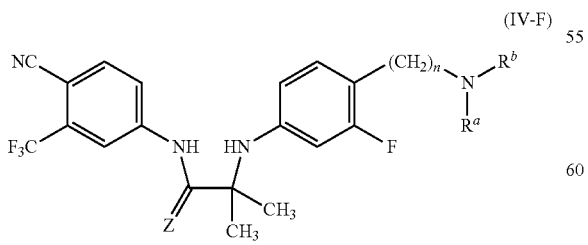

where n is an integer from 1 to 8 and $R^a$ and $R^b$ are as defined in formula (IV) or any embodiment thereof.

In some embodiments the compound is a compound of Formula IV-G:

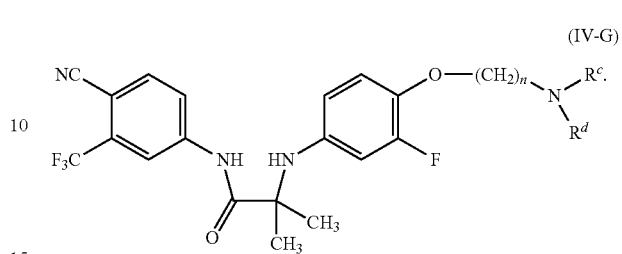

where n is an integer from 1 to 8 and $R^c$ and $R^d$ are as defined in formula (IV) or any embodiment thereof.

In some embodiments the compound is a compound of Formula IV-H:

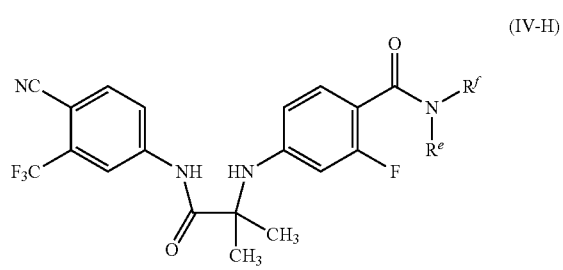

where n is an integer from 1 to 8 and $R^c$ and $R^d$ are as defined in formula (IV) or any embodiment thereof.

In some embodiments the compound is a compound of Formula IV-J:

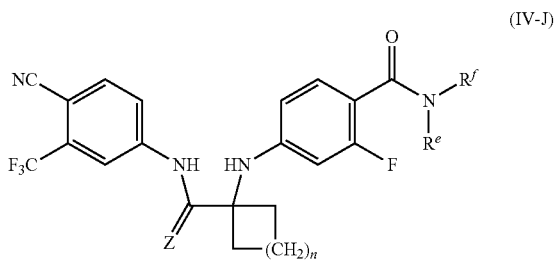

where n is 0 to 3, and $R^e$ and $R^f$ are as defined in formula (IV) or any embodiment thereof.

Examples of compounds according to Formula (IV) are depicted in Table 2. The compounds depicted may be present as salts even if salts are not depicted and it is understood that this disclosure embraces all salts and solvates of the compounds depicted here, as well as the non-salt and non-solvate form of the compound, as is well understood by the skilled artisan. It is thus understood that pharmaceutically acceptable salts of compounds are intended.

TABLE 2

Representative Compounds of Formula IV.

| Structure | Compound No. |
|---|---|
| (structure) | 1 |
| (structure) | 2 |
| (structure) | 3 |
| (structure) | 4 |
| (structure) | 5 |
| (structure) | 6 |

TABLE 2-continued

Representative Compounds of Formula IV.

| Structure | Compound No. |
|---|---|
| 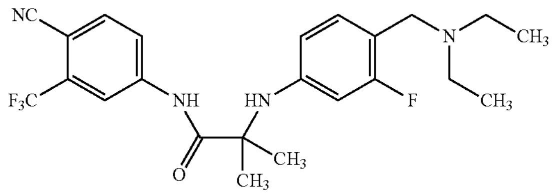 [SMILES: CCN(CC)Cc1ccc(NC(C)(C)C(=O)Nc2ccc(C#N)c(C(F)(F)F)c2)cc1F] | 7 |
| 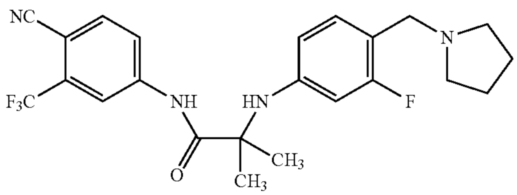 [SMILES: CC(C)(Nc1ccc(CN2CCCC2)c(F)c1)C(=O)Nc1ccc(C#N)c(C(F)(F)F)c1] | 8 |
| 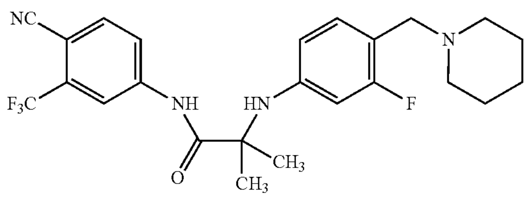 [SMILES: CC(C)(Nc1ccc(CN2CCCCC2)c(F)c1)C(=O)Nc1ccc(C#N)c(C(F)(F)F)c1] | 9 |
| 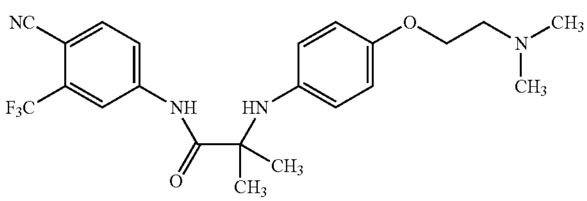 [SMILES: CN(C)CCOc1ccc(NC(C)(C)C(=O)Nc2ccc(C#N)c(C(F)(F)F)c2)cc1] | 10 |

In some embodiments the compound is a compound of Formula V:

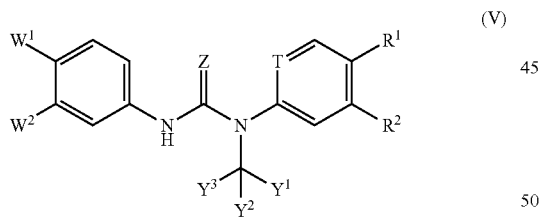

wherein:
$W^1$ is CN, $NO_2$ or $SO_2R^4$;
$W^2$ is hydrogen, alkyl, substituted alkyl, alkenyl, substituted alkenyl, alkynyl, substituted alkynyl or halogen;
Z is S, O or $NR^5$;
$Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, substituted heterocyclyl or $Y^1$ and $Y^2$ are taken together with the carbon to which they are attached to form a cycle which can be heterocyclic, substituted heterocyclic, cycloalkyl, substituted cycloalkyl;
$Y^3$ is carboxyl, formyl, alkyl carbonyl, substituted alkyl carbonyl, alkenyl carbonyl, substituted alkenyl carbonyl, alkynyl carbonyl, substituted alkynyl carbonyl, aryl carbonyl, substituted aryl carbonyl, heteroaryl carbonyl, substituted heteroaryl carbonyl, arylalkyl carbonyl, arylalkenyl carbonyl, arylalkynyl carbonyl, heteroaralkyl carbonyl, heterocyclyl carbonyl, substituted heterocyclyl carbonyl, cyano, aminocarbonyl, N-alkyl aminocarbonyl, N,N-dialkyl am inocarbonyl, N-substituted alkyl aminocarbonyl, N,N-bis-substituted alkyl aminocarbonyl, alkoxy carbonyl, substituted alkoxy carbonyl, halocarbonyl, hydroxymethyl, alkylhydroxymethyl, substituted alkoxymethyl, thiocarbonyl, thioformyl, alkyl thiocarbonyl, substituted alkyl thiocarbonyl, alkenyl thiocarbonyl, substituted alkenyl thiocarbonyl, alkynyl thiocarbonyl, substituted alkynyl thiocarbonyl, aryl thiocarbonyl, substituted aryl thiocarbonyl, heteroaryl thiocarbonyl, substituted heteroaryl thiocarbonyl, arylalkyl thiocarbonyl, arylalkenyl thiocarbonyl, arylalkynyl thiocarbonyl, heteroaralkyl thiocarbonyl, heterocyclyl thiocarbonyl, substituted heterocyclyl thiocarbonyl, thiocarbamyl, N-alkyl thiocarbamyl, N,N-dialkyl thiocarbamyl, N-substituted alkyl thiocarbamyl, N,N-bis-substituted alkyl thiocarbamyl, alkoxy thiocarbonyl, substituted alkoxy thiocarbonyl, halothiocarbonyl, mercaptomethyl, substituted alkylthiomethyl;

heteroaryl carbonyl, substituted heteroaryl carbonyl, arylalkyl carbonyl, arylalkenyl carbonyl, arylalkynyl carbonyl, heteroaralkyl carbonyl, heterocyclyl carbonyl, substituted heterocyclyl carbonyl, cyano, aminocarbonyl, N-alkyl aminocarbonyl, N,N-dialkyl aminocarbonyl, N-substituted alkyl aminocarbonyl, N,N-bis-substituted alkyl aminocarbonyl, alkoxy carbonyl, substituted alkoxy carbonyl, halocarbonyl, hydroxymethyl, alkoxymethyl, substituted alkoxymethyl;

T is carbon or nitrogen and can be at any position in the ring;

$R^1$ is hydrogen, —$C_1$-$C_8$ alkyl-$NR^aR^b$, —O—$C_1$-$C_8$ alkyl-$NR^cR^d$, —C(O)$NR^eR^f$ or —$NR^gR^h$, where:

$R^a$ is a $C_1$-$C_{12}$ alkyl and $R^b$ is H or a $C_1$-$C_{12}$ alkyl or $R^a$ and $R^b$ are taken together with the N to which they are attached to form a heterocyclic ring;

$R^c$ is a $C_1$-$C_{12}$ alkyl and $R^d$ is H or a $C_1$-$C_{12}$ alkyl or $R^c$ and $R^d$ are taken together with the N to which they are attached to form a heterocyclic ring;

$R^e$ is H or a $C_1$-$C_{12}$ alkyl and $R^f$ is H or a $C_1$-$C_{12}$ alkyl, or $R^e$ and $R^f$ are taken together with the N to which they are attached to form a heterocyclic ring;

$R^g$ is H or a $C_1$-$C_{12}$ alkyl and $R^h$ is H or a $C_1$-$C_{12}$ alkyl, or $R^g$ and $R^h$ are taken together with the N to which they are attached to form a heterocyclic ring;

$R^2$ is hydrogen, halogen, nitro, alkyl or substituted alkyl;

$R^4$ is H, alkyl, substituted alkyl, aryl or substituted aryl;

$R^5$ is alkyl, substituted alkyl, aryl or substituted aryl.

In some embodiments the compound is of the formula (V) where T is nitrogen when $R^4$ and $R^5$ are both hydrogen.

In some embodiments the compound is of the formula (V) where $W^1$ is CN. In some embodiments $W^2$ is hydrogen, alkyl, substituted alkyl, alkenyl, substituted alkenyl, alkynyl or substituted alkynyl. In some embodiments $W^2$ is substituted alkyl, substituted alkenyl or substituted alkynyl where the alkyl, alkenyl or alkynyl is substituted with one or more halogens. $W^2$ in some embodiments is a haloalkyl, haloalkenyl, haloalkynyl or perhaloalkyl. $W^2$ in some embodiments is a substituted alkyl. In some embodiments $W^2$ is substituted alkyl where the alkyl is substituted with one or more halogens. In some embodiments $W^2$ is a haloalkyl or perhaloalkyl. In some embodiments $W^2$ is a perhaloalkyl. The perhaloalkyl in some embodiments is a $C_1$-$C_8$ perhaloalkyl, such as trihalomethyl. In some embodiments $W^2$ is trifluoromethyl. In a particular, $W^1$ is CN and $W^2$ is perhaloalkyl. In another particular, $W^1$ is CN and $W^2$ is $CF_3$. In some embodiments $W^2$ is hydrogen. In a particular, $W^1$ is CN and $W^2$ is hydrogen.

In some embodiments $Y^1$ and $Y^2$ are both a $C_1$-$C_8$ alkyl. In some embodiments $Y^1$ and $Y^2$ are the same $C_1$-$C_8$ alkyl, such as when both $Y^1$ and $Y^2$ are methyl, ethyl, propyl or butyl. In some embodiments $Y^1$ and $Y^2$ are both methyl or are taken together with the carbon to which they are attached to form a $C_3$-$C_5$ cycloalkyl. In some embodiments the compounds of formula (V) are provided where $Y^1$ and $Y^2$ are both methyl. In some embodiments the compounds of formula (V) are provided where one of $Y^1$ or $Y^2$ is hydrogen and the other of $Y^1$ or $Y^2$ is $C_1$-$C_8$ alkyl. In some embodiments one of $Y^1$ or $Y^2$ is hydrogen and the other of $Y^1$ or $Y^2$ is methyl, ethyl, propyl or butyl. In some embodiments the compounds of formula (V) are provided where at least one of $Y^1$ and $Y^2$ is alkyl where the alkyl is a cycloalkyl. In some embodiments the compounds of formula (V) are provided where at least one of $Y^1$ and $Y^2$ is substituted alkyl where the substituted alkyl is a substituted cycloalkyl. In some embodiments the compounds of formula (V) are provided where one or both of $Y^1$ and $Y^2$ are substituted alkyl, substituted alkenyl or substituted alkynyl where the alkyl, alkenyl or alkynyl is substituted with one or more halogens. In some embodiments at least one of $Y^1$ and $Y^2$ is a haloalkyl, haloalkenyl or haloalkynyl. In another such embodiment both $Y^1$ and $Y^2$ are a haloalkyl, haloalkenyl or haloalkynyl. In some embodiments the compounds of formula (V) are provided where $Y^1$ and $Y^2$ are taken together with the carbon to which they are attached to form a $C_3$-$C_5$ cycloalkyl. In some embodiments $Y^1$ and $Y^2$ are taken together with the carbon to which they are attached to form a cyclopropyl, cyclobutyl or cyclopentyl moiety. In a particular, $Y^1$ and $Y^2$ are both methyl, $W^1$ is CN. In another particular, $Y^1$ and $Y^2$ are both methyl and $W^2$ is a perhaloalkyl such as $CF_3$. In some embodiments $Y^1$ and $Y^2$ are both methyl, $W^1$ is CN and V is a perhaloalkyl such as $CF_3$. In some embodiments $Y^1$ is isopropyl, $Y^2$ is H, $W^1$ is CN and $W^2$ is a perhaloalkyl such as $CF_3$. In a particular, $Y^1$ and $Y^2$ are taken together with the carbon to which they are attached to form a cyclopropyl, $W^1$ is CN. In another particular of formula (V), $Y^1$ and $Y^2$ are taken together with the carbon to which they are attached to form a cyclopropyl and $W^2$ is a perhaloalkyl such as $CF_3$. In some embodiments $Y^1$ and $Y^2$ are taken together with the carbon to which they are attached to form a cyclopropyl, $W^1$ is CN and $W^2$ is a perhaloalkyl such as $CF_3$.

In a, $Y^3$ is carboxyl, carbonyl or derivative thereof, such as carboxyl, formyl, alkyl carbonyl, substituted alkyl carbonyl, alkenyl carbonyl, substituted alkenyl carbonyl, alkynyl carbonyl, substituted alkynyl carbonyl, aryl carbonyl, substituted aryl carbonyl, heteroaryl carbonyl, substituted heteroaryl carbonyl, arylalkyl carbonyl, arylalkenyl carbonyl, arylalkynyl carbonyl, heteroaralkyl carbonyl, heterocyclyl carbonyl, substituted heterocyclyl carbonyl, cyano, carbamyl, N-alkyl carbamyl, N,N-dialkyl carbamyl, N-substituted alkyl carbamyl, N,N-bis-substituted alkyl carbamyl, alkoxy carbonyl, substituted alkoxy carbonyl, halocarbonyl, hydroxymethyl, alkylhydroxymethyl or substituted alkoxymethyl. In a, $Y^3$ is thiocarboxyl, thioformyl, alkyl thiocarbonyl, substituted alkyl thiocarbonyl, alkenyl thiocarbonyl, substituted alkenyl thiocarbonyl, alkynyl thiocarbonyl, substituted alkynyl thiocarbonyl, aryl thiocarbonyl, substituted aryl thiocarbonyl, heteroaryl thiocarbonyl, substituted heteroaryl thiocarbonyl, arylalkyl thiocarbonyl, arylalkenyl thiocarbonyl, arylalkynyl thiocarbonyl, heteroaralkyl thiocarbonyl, heterocyclyl thiocarbonyl, substituted heterocyclyl thiocarbonyl, thiocarbamyl, N-alkyl thiocarbamyl, N,N-dialkyl thiocarbamyl, N-substituted alkyl thiocarbamyl, N,N-bis-substituted alkyl thiocarbamyl, alkoxy thiocarbonyl, substituted alkoxy thiocarbonyl, halothiocarbonyl, mercaptomethyl, substituted alkylthiomethyl.

In a particular, $Y^3$ is thiocarboxyl or carboxyl. In a particular, $Y^3$ is carboxyl.

In a particular, $Y^3$ is aminocarbonyl, N-alkyl aminocarbonyl, N,N-dialkyl aminocarbonyl. In a particular, $Y^3$ is aminocarbonyl.

In another particular, $Y^3$ is formyl, alkyl carbonyl or alkoxy carbonyl. In a particular, $Y^3$ is alkoxycarbonyl.

In a, $Y^3$ is hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, substituted heterocyclyl, In some embodiments the compounds of formula (V) are provided where Z is substituted N (e.g., $NR^5$), S or O. In some embodiments Z is O. In some embodiments Z is S. In a particular, Z is S or O and $Y^1$ and $Y^2$ are both a $C_1$-$C_8$ alkyl. In some embodiments Z is S or O and $Y^1$ and $Y^2$ are the same $C_1$-$C_8$ alkyl. In some embodiments Z is S or O and $Y^1$ and $Y^2$ are both methyl or are taken together with the carbon to which they are attached to form a $C_3$-$C_5$ cycloalkyl.

In some embodiments the compounds of formula (V) are provided where Z is S and the compound is further defined by one or more of the following structural features: (i) $Y^1$ and $Y^2$ are both a $C_1$-$C_8$ alkyl; (ii) $W^1$ is CN; (iii) $W^2$ is perhaloalkyl. In some embodiments Z is S, $Y^1$ and $Y^2$ are the same $C_1$-$C_8$ alkyl, $W^1$ is CN and $W^2$ is $CF_3$. In one particular such embodiment Z is S, $Y^1$ and $Y^2$ are each methyl, $W^1$ is CN and $W^2$ is $CF_3$. In one particular such embodiment Z is S, $Y^1$ and $Y^2$ are each methyl, $Y^3$ is carboxyl, $W^1$ is CN and $W^2$ is $CF_3$. In some embodiments the compounds of formula (V) are provided where Z is S and the compound is further defined by one or more of the following structural features: (i) $Y^1$ and $Y^2$ are taken together with the carbon to which they are attached to form a $C_3$-$C_5$ cycloalkyl; (ii) $W^1$ is CN; (iii) $W^2$ is perhaloalkyl, (iv) $Y^3$ is carboxyl. In some embodiments Z is S, $Y^1$ and $Y^2$ are taken together with the carbon to which they are attached to form a $C_3$-$C_5$ cycloalkyl, $W^1$ is CN and $W^2$ is $CF_3$. In one particular embodiment Z is O, $Y^1$ and $Y^2$ are taken together with the carbon to which they are attached to form a cyclopropyl, $Y^3$ is carboxyl, $W^1$ is CN and $W^2$ is $CF_3$.

In some embodiments the compounds of formula (V) are provided where Z is S and the compound is further defined by one or more of the following structural features: (i) $Y^1$ and $Y^2$ are both a $C_1$-$C_8$ alkyl; (ii) $W^1$ is CN; (iii) $W^2$ is perhaloalkyl; (iv) $Y^3$ is selected from the group consisting of thiocarboxyl, aminocarbonyl, N-alkyl aminocarbonyl, N,N-dialkyl aminocarbonyl, formyl, alkyl carbonyl or alkoxycarbonyl. In one particular such embodiment $Y^3$ is alkoxycarbonyl or aminocarbonyl. In one particular such embodiment Z is S, $Y^1$ and $Y^2$ are each methyl, $Y^3$ is alkoxycarbonyl or aminocarbonyl, $W^1$ is CN and $W^2$ is $CF_3$. In some embodiments the compounds of formula (V) are provided where Z is S and the compound is further defined by one or more of the following structural features: (i) $Y^1$ and $Y^2$ are taken together with the carbon to which they are attached to form a $C_3$-$C_5$ cycloalkyl; (ii) $W^1$ is CN; (iii) $W^2$ is perhaloalkyl, (iv) $Y^3$ is alkoxycarbonyl or aminocarbonyl. In some embodiments Z is S, $Y^1$ and $Y^2$ are taken together with the carbon to which they are attached to form a $C_3$-$C_5$ cycloalkyl, $W^1$ is CN and $W^2$ is $CF_3$. In one particular embodiment Z is O, $Y^1$ and $Y^2$ are taken together with the carbon to which they are attached to form a cyclopropyl, $Y^3$ is alkoxycarbonyl or aminocarbonyl, $W^1$ is CN and $W^2$ is $CF_3$.

In some embodiments T is C. In some embodiments T is N. It is understood that where applicable, any embodiment may in some embodiments be further defined by T being C. It is understood that where applicable, any embodiment may in some embodiments be further defined by T being N. For example, the embodiments described herein may in some embodiments be further defined by T being C. Additionally, it is understood that the embodiments described herein may in some embodiments be further defined by T being N.

Compounds of formula (V) are provided where $R^1$ is —$C_1$-$C_8$ alkyl-$NR^aR^b$ where $R^a$ is a $C_1$-$C_{12}$ alkyl and $R^b$ is H or a $C_1$-$C_{12}$ alkyl or $R^a$ and $R^b$ are taken together with the N to which they are attached to form a heterocyclic ring. In some embodiments the —$C_1$-$C_8$ alkyl moiety of —$C_1$-$C_8$ alkyl-$NR^aR^b$ is a —$(CH_2)_n$ moiety where n is an integer from 1 to 8. In some embodiments n is less than 4. In some embodiments n is 1. In some embodiments $R^a$ is a $C_1$-$C_{12}$ alkyl and $R^b$ is H. For example, $R^a$ in some embodiments is methyl, ethyl, propyl, butyl or pentyl and $R^b$ is H. In some embodiments $R^a$ is a $C_1$-$C_8$ alkyl and $R^b$ is H. In some embodiments $R^a$ is a $C_3$-$C_6$ alkyl and $R^b$ is H. Compounds of formula (V) are also provided where $R^a$ is a $C_1$-$C_{12}$ alkyl and $R^b$ is a $C_1$-$C_{12}$ alkyl. In some embodiments $R^a$ is a $C_3$-$C_{12}$ cycloalkyl and $R^b$ is a $C_1$-$C_{12}$ alkyl (e.g., methyl). In some embodiments $R^a$ and $R^b$ are independently a $C_1$-$C_8$ alkyl. In some embodiments $R^a$ and $R^b$ are the same $C_1$-$C_{12}$ alkyl, e.g., when both $R^a$ and $R^b$ are ethyl. In some embodiments $R^a$ and $R^b$ are independently a $C_3$-$C_6$ alkyl. In still some embodiments $R^a$ and $R^b$ are taken together with the N to which they are attached to form a heterocyclic ring. In some embodiments when $R^a$ and $R^b$ are taken together to form a heterocyclic ring, the ring is a 4- to 7-membered heterocyclic ring. The heterocyclic ring formed by $R^a$, $R^b$ and the N to which they are attached in some embodiments contains only C and N as annular atoms. In some embodiments the heterocycle contains as annular atoms only C and the N provided when $R^a$ and $R^b$ are taken together with the N to which they are attached. In a particular, $R^a$ and $R^b$ are taken together with the N to which they are attached to form a pyrrolidinyl or piperidinyl ring. Where applicable, for any detailed herein wherein $R^1$ is —$C_1$-$C_8$ alkyl-$NR^aR^b$, in some embodiments the $C_1$-$C_8$ alkyl moiety of —$C_1$-$C_8$ alkyl-$NR^aR^b$ is a —$(CH_2)_n$ moiety where n is 1. Thus, $R^1$ in some embodiments is —$CH_2NR^aR^b$ where $R^a$ and $R^b$ may be as defined herein. In some embodiments $R^1$ is:

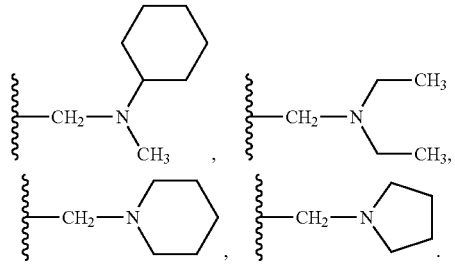

In some of these embodiments the compound is further defined by any one or more of the following structural features: (i) $W^1$ is CN; (ii) $W^2$ is perhaloalkyl (e.g., $CF_3$); (iii) Z is S; (iv) $Y^1$ and $Y^2$ are both methyl and (v) T is C. In some embodiments $R^1$ is as defined above and the compound is further defined by any one or more of the following structural features: (i) $W^1$ is CN; (ii) $W^2$ is perhaloalkyl (e.g., $CF_3$); (iii) Z is S; (iv) $Y^1$ and $Y^2$ are both methyl, (v) $R^2$ is halogen (e.g., F) and (vi) T is C.

In some embodiments $R^1$ is —O—$C_1$-$C_8$ alkyl-$NR^cR^d$ where $R^c$ is a $C_1$-$C_{12}$ alkyl and $R^d$ is H or a $C_1$-$C_{12}$ alkyl or $R^c$ and $R^d$ are taken together with the N to which they are attached to form a heterocyclic ring. In some embodiments the —$C_1$-$C_8$ alkyl moiety of —O—$C_1$-$C_8$ alkyl-$NR^cR^d$ is a —$(CH_2)_n$ moiety where n is an integer from 1 to 8. In some embodiments n is less than 4. In some embodiments n is 2. In some embodiments $R^c$ is a $C_1$-$C_{12}$ alkyl and $R^d$ is H. For example, $R^c$ in some embodiments is methyl, ethyl, propyl, butyl or pentyl and $R^d$ is H. In some embodiments $R^c$ is a $C_1$-$C_8$ alkyl and $R^d$ is H. In some embodiments $R^c$ is a $C_1$-$C_4$ alkyl and $R^d$ is H. Compounds of formula (V) are also provided where $R^c$ and $R^d$ are independently a $C_1$-$C_{12}$ alkyl. In some embodiments $R^c$ and $R^d$ are the same $C_1$-$C_{12}$ alkyl, e.g., when both $R^c$ and $R^d$ are methyl. In some embodiments $R^c$ and $R^d$ are independently a $C_1$-$C_8$ alkyl. In some embodiments $R^c$ and $R^d$ are independently a $C_1$-$C_4$ alkyl. In still some embodiments $R^c$ and $R^d$ are taken together with the N to which they are attached to form a heterocyclic ring. In some embodiments when $R^c$ and $R^d$ are taken together to form a heterocyclic ring, the ring is a 4- to 7-membered heterocyclic ring. The heterocyclic ring formed by $R^c$, $R^d$ and the N to which they are attached in some embodiments contains only C and N as annular atoms. In some embodiments the heterocycle contains as annular atoms only C and the N provided when $R^c$ and $R^d$ are taken together with the N to which they are attached. In a particular, $R^c$ and $R^d$ are taken together with the N to which they are attached to form a pyrrolidinyl or piperidinyl ring. Where applicable, for any detailed herein wherein $R^1$ is —O—$C_1$-$C_8$ alkyl-$NR^cR^d$, in some embodiments the $C_1$-$C_8$ alkyl moiety of —O—$C_1$-$C_8$ alkyl-$NR^cR^d$ is a —$(CH_2)_n$— moiety where n is 2. Thus, $R^1$ in some embodiments is —$OCH_2CH_2NR^cR^d$ where $R^c$ and $R^d$ may be as defined herein. In some embodiments $R^1$ is:

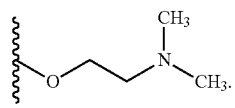 [SMILES: *OCCN(C)C]

In some of these embodiments the compound is further defined by any one or more of the following structural features: (i) $W^1$ is CN; (ii) $W^2$ is perhaloalkyl (e.g., $CF_3$); (iii) Z is S; (iv) $Y^1$ and $Y^2$ are both methyl; (v) $R^2$ is H, and (vi) T is C.

In some embodiments $R^1$ is —$C(O)NR^eR^f$ where $R^e$ and $R^f$ are as defined in provisions (i) or (ii) or (iii) or (iv): (i) $R^e$ and $R^f$ are independently H or a $C_1$-$C_{12}$ alkyl; (ii) $R^e$ is a $C_1$-$C_{12}$ alkyl and $R^f$ is H or a $C_1$-$C_{12}$ alkyl; (iii) $R^e$ is a $C_1$-$C_{12}$ alkyl and $R^f$ is $C_1$-$C_{12}$ alkyl; or (iv) $R^e$ and $R^f$ are taken together with the N to which they are attached to form a heterocyclic ring. In some embodiments the compound is of the formula (V) where $R^1$ is —$C(O)NR^eR^f$ and $R^e$ and $R^f$ are independently H or a $C_1$-$C_{12}$ alkyl. In some embodiments the compound is of the formula (V) where $R^1$ is —$C(O)NR^eR^f$ and $R^e$ is a $C_1$-$C_{12}$ alkyl and $R^f$ is H or a $C_1$-$C_{12}$ alkyl. In some embodiments the compound is of the formula (V) where $R^1$ is —$C(O)NR^eR^f$ and $R^e$ is a $C_1$-$C_{12}$ alkyl and $R^f$ is $C_1$-$C_{12}$ alkyl. In some embodiments the compound is of the formula (V) where $R^1$ is —$C(O)NR^eR^f$ and $R^e$ and $R^f$ are taken together with the N to which they are attached to form a heterocyclic ring. In some embodiments $R^e$ is a $C_1$-$C_{12}$ alkyl and $R^f$ is H. For example, $R^e$ in some embodiments is methyl, ethyl, propyl, butyl, pentyl or hexyl and $R^f$ is H. In another particular embodiment $R^e$ is a $C_3$-$C_{12}$ cycloalkyl (e.g., cyclopentyl) and $R^f$ is H. In some embodiments $R^e$ is a $C_3$-$C_{12}$ branched alkyl (e.g., tert-butyl) and $R^f$ is H. In some embodiments $R^e$ is a $C_1$-$C_8$ alkyl and $R^f$ is H (e.g., where $R^e$ is methyl and $R^f$ is H). In some embodiments $R^e$ is a $C_3$-$C_6$ alkyl and $R^f$ is H (e.g., where $R^e$ is propyl or butyl and $R^f$ is H). In another particular embodiment $R^e$ is a $C_1$-$C_{12}$ alkyl and $R^f$ is a $C_1$-$C_{12}$ alkyl (e.g., where $R^e$ is ethyl and $R^f$ is methyl). Compounds of formula (V) are also provided where $R^e$ and $R^f$ are independently a $C_1$-$C_{12}$ alkyl (e.g., where both $R^e$ and $R^f$ are methyl). In some embodiments the compounds of formula (V) are provided where $R^e$ and $R^f$ are independently a $C_1$-$C_{12}$ alkyl. In some embodiments $R^e$ and $R^f$ are the same $C_1$-$C_{12}$ alkyl, e.g., when both $R^e$ and $R^f$ are ethyl. In some embodiments $R^e$ and $R^f$ are independently a $C_1$-$C_8$ alkyl. In some embodiments $R^e$ and $R^f$ are independently a $C_3$-$C_6$ alkyl. In some embodiments at least one of $R^e$ and $R^f$ is a $C_3$-$C_6$ cycloalkyl. In still some embodiments $R^e$ and $R^f$ are taken together with the N to which they are attached to form a heterocyclic ring. In some embodiments when $R^e$ and $R^f$ are taken together to form a heterocyclic ring, the ring is a 4- to 7-membered heterocyclic ring. The heterocyclic ring formed by $R^e$, $R^f$ and the N to which they are attached in some embodiments contains only C and N as annular atoms. In some embodiments the heterocycle contains as annular atoms only C and the N provided when $R^e$ and $R^f$ are taken together with the N to which they are attached. In a particular, $R^e$ and $R^f$ are taken together with the N to which they are attached to form a pyrrolidinyl or piperidinyl ring. In some embodiments $R^1$ is:

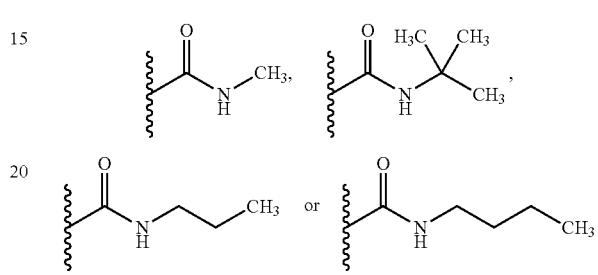

In some of these embodiments the compound is further defined by any one or more of the following structural features: (i) $W^1$ is CN; (ii) $W^2$ is perhaloalkyl (e.g., $CF_3$) or hydrogen; (iii) Z is S; (iv) $Y^1$ and $Y^2$ are both methyl and (vi) T is C. In some embodiments $R^1$ is as defined above and the compound is further defined by any one or more of the following structural features: (i) $W^1$ is CN; (ii) $W^2$ is perhaloalkyl (e.g., $CF_3$) or hydrogen; (iii) Z is S; (iv) $Y^1$ and $Y^2$ are taken together with the carbon to which they are attached to form a cyclopropyl and (vi) T is C.

In any embodiment detailed herein, $R^2$ in some embodiments is halo (e.g., F). In some embodiments $R^2$ is H. In some embodiments $R^2$ is halo when $R^1$ is —$C_1$-$C_8$ alkyl-$NR^aR^b$ or —$C(O)NR^eR^f$. In some embodiments $R^2$ is H when $R^1$ is —O—$C_1$-$C_8$ alkyl-$NR^cR^d$.

In any embodiment detailed herein, $Y^3$ is thiocarboxyl, carboxyl, aminocarbonyl, N-alkyl aminocarbonyl, N,N-dialkyl aminocarbonyl, formyl, alkyl carbonyl or alkoxy carbonyl. In a particular, $Y^3$ is carboxyl. In another particular, $Y^3$ is alkoxycarbonyl. In another particular, $Y^3$ is aminocarbonyl.

In some embodiments the compound is a compound of Formula V-A:

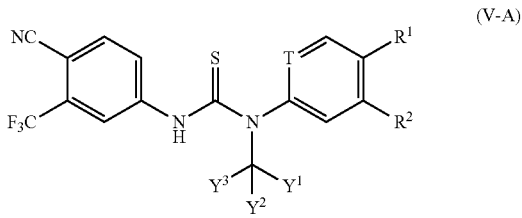

where $Y^1$, $Y^2$, $Y^3$, T, $R^1$ and $R^2$ are as defined in formula (V) or any embodiment thereof.

In some embodiments the compound is a compound of Formula V-B:

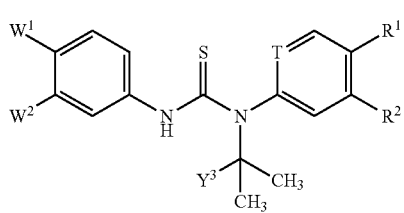

(V-B)

where $W^1$, $W^2$, $Y^3$, T, $R^1$ and $R^2$ are as defined in formula (V) or any embodiment thereof.

In some embodiments the compound is a compound of Formula V-C:

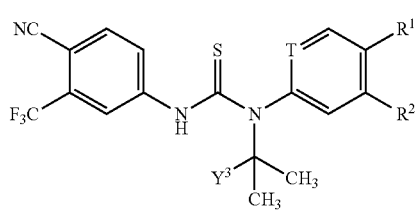

(V-C)

where $Y^3$, T, $R^1$ and $R^2$ are as defined in formula (V) or any embodiment thereof.

In some embodiments the compound is a compound of Formula V-D:

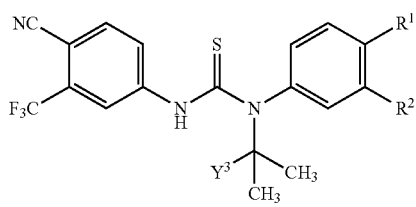

(V-D)

where $Y^3$, $R^1$ and $R^2$ are as defined in formula (V) or any embodiment thereof.

In some embodiments the compound is a compound of Formula V-E:

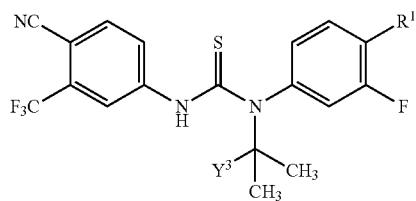

(V-E)

where $Y^3$ and $R^1$ is as defined in formula (V) or any embodiment thereof.

In some embodiments the compound is a compound of Formula V-F:

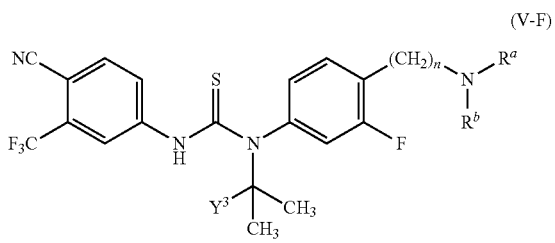

(V-F)

where n is an integer from 1 to 8 and $Y^3$, $R^a$ and $R^b$ are as defined in formula (V) or any embodiment thereof.

In some embodiments the compound is a compound of Formula V-G:

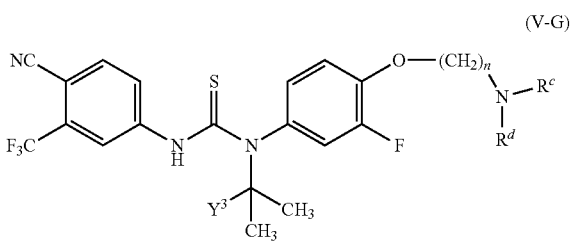

(V-G)

where n is an integer from 1 to 8 and $Y^3$, $R^c$ and $R^d$ are as defined in formula (V) or any embodiment thereof.

In some embodiments the compound is a compound of Formula V-H:

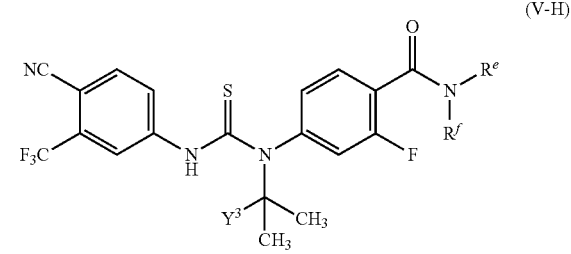

(V-H)

where $Y^3$, $R^e$ and $R^f$ are as defined in formula (V) or any embodiment thereof.

In some embodiments the compound is a compound of Formula V-J:

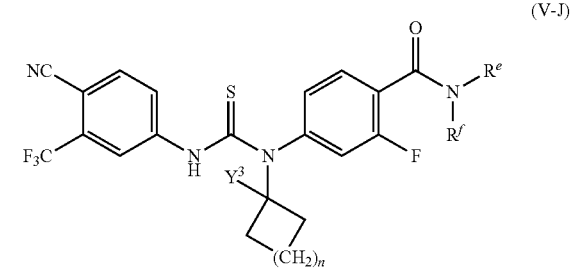

(V-J)

where n is 0 to 3, and $Y^3$, $R^e$ and $R^f$ are as defined in formula (V) or any embodiment thereof.

In some embodiments the compound is a compound of Formula V-K:

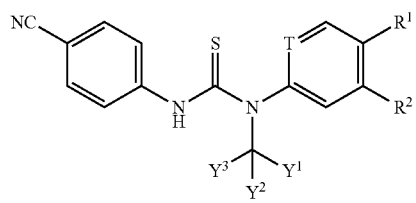

(V-K)

where $Y^1$, $Y^2$, $Y^3$, $R^1$ and $R^2$ are as defined in formula (V) or any embodiment thereof.

In some embodiments the compound is a compound of Formula V-L:

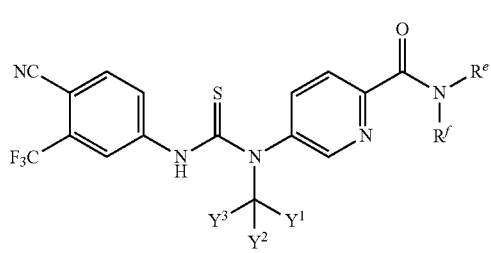

(V-L)

where n is 0 to 3, and $Y^1$, $Y^2$, $Y^3$, $R^e$ and $R^f$ are as defined in formula (V) or any embodiment thereof.

In some embodiments the compound is a compound of Formula V-M:

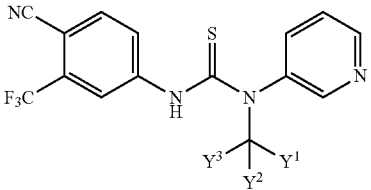

(V-M)

where $Y^1$, $Y^2$ and $Y^3$ are as defined in formula (V) or any embodiment thereof.

In a variation of any one of formula (V-A), (V-B), (V-C), (V-D), (V-E), (V-F), (V-G), (V-H), (V-J), (V-K), (V-L) to (V-M) detailed herein, in particular embodiments $Y^3$ is thiocarboxyl, carboxyl, aminocarbonyl, N-alkyl aminocarbonyl, N,N-dialkyl aminocarbonyl, formyl, alkyl carbonyl or alkoxy carbonyl. In a particular variation of any one of formula (V-A), (V-B), (V-C), (V-D), (V-E), (V-F), (V-G), (V-H), (V-J), (V-K), (V-L) to (V-M) detailed herein, $Y^3$ is carboxyl. In another particular variation of any one of formula (V-A), (V-B), (V-C), (V-D), (V-E), (V-F), (V-G), (V-H), (V-J), (V-K), (V-L) to (V-M) detailed herein, $Y^3$ is alkoxy carbonyl. In another particular variation of any one of formula (V-A), (V-B), (V-C), (V-D), (V-E), (V-F), (V-G), (V-H), (V-J), (V-K), (V-L) to (V-M) detailed herein, $Y^3$ is aminocarbonyl.

Examples of compounds according to Formula (V) are depicted in Table 3. The compounds depicted may be present as salts even if salts are not depicted and it is understood that this disclosure embraces all salts and solvates of the compounds depicted here, as well as the non-salt and non-solvate form of the compound, as is well understood by the skilled artisan. It is thus understood that pharmaceutically acceptable salts of compounds are intended.

TABLE 3

| Representative Compounds of Formula V. | |
|---|---|
| Structure | Compound No. |
| 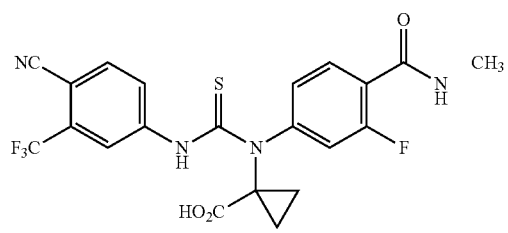 | 11 |
| | 12 |

TABLE 3-continued

Representative Compounds of Formula V.

| Structure | Compound No. |
| --- | --- |
| 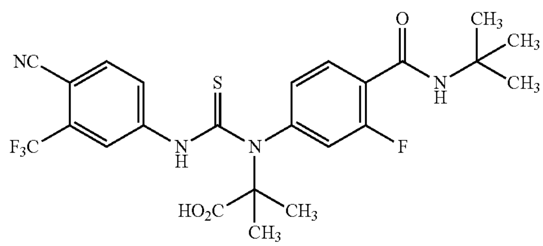 [SMILES: CC(C)(C)NC(=O)c1ccc(N(C(=S)Nc2ccc(C#N)c(C(F)(F)F)c2)C(C)(C)C(=O)O)cc1F] | 13 |
| 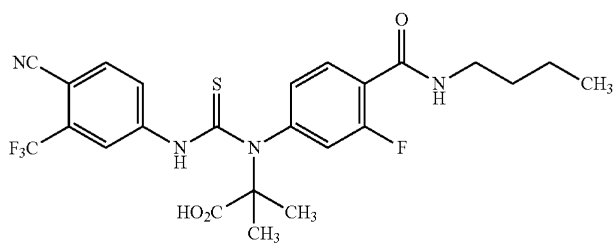 [SMILES: CCCCNC(=O)c1ccc(N(C(=S)Nc2ccc(C#N)c(C(F)(F)F)c2)C(C)(C)C(=O)O)cc1F] | 14 |
| 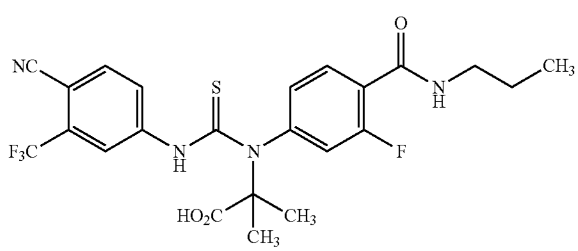 [SMILES: CCCNC(=O)c1ccc(N(C(=S)Nc2ccc(C#N)c(C(F)(F)F)c2)C(C)(C)C(=O)O)cc1F] | 15 |
| 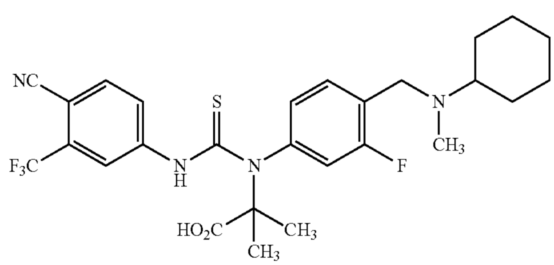 [SMILES: CN(Cc1ccc(N(C(=S)Nc2ccc(C#N)c(C(F)(F)F)c2)C(C)(C)C(=O)O)cc1F)C1CCCCC1] | 16 |
| 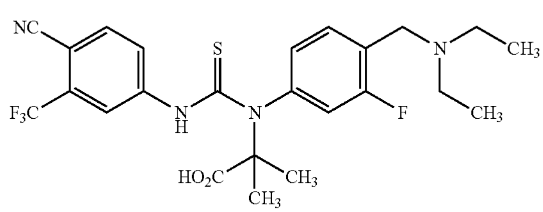 [SMILES: CCN(CC)Cc1ccc(N(C(=S)Nc2ccc(C#N)c(C(F)(F)F)c2)C(C)(C)C(=O)O)cc1F] | 17 |
| 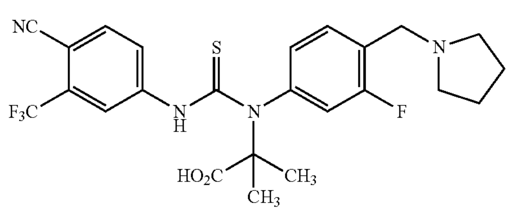 [SMILES: CC(C)(C(=O)O)N(C(=S)Nc1ccc(C#N)c(C(F)(F)F)c1)c1ccc(CN2CCCC2)c(F)c1] | 18 |

TABLE 3-continued

Representative Compounds of Formula V.

| Structure | Compound No. |
| --- | --- |
| (structure) | 19 |
| (structure) | 20 |
| (structure) | 21 |
| (structure) | 22 |
| (structure) | 23 |
| (structure) | 24 |

TABLE 3-continued

Representative Compounds of Formula V.

| Structure | Compound No. |
|---|---|
| (structure) | 25 |
| (structure) | 26 |
| (structure) | 27 |

7. Metabolites

In some embodiments the compound is a metabolite of a diarylthiohydantoin compound, for example as disclosed in WO 2010/099238.

In some embodiments the compound is a compound of Formula VI:

(VI)

wherein:
X is S or O, and
when X is S, then $R^1$ is OH or $NH_2$; and
when X is O then $R^1$ is OH, $NH_2$ or NHMe,
or a pharmaceutically acceptable salt or solvate thereof.

In some embodiments a compound of Formula VI is:

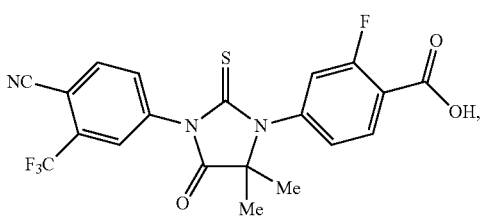

(MI)

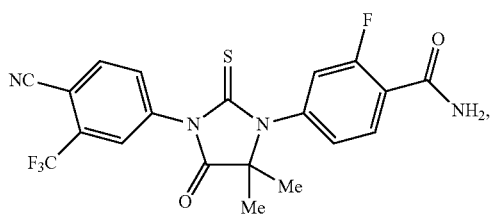

(MII)

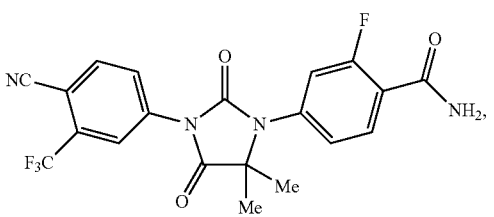

(MIII)

-continued

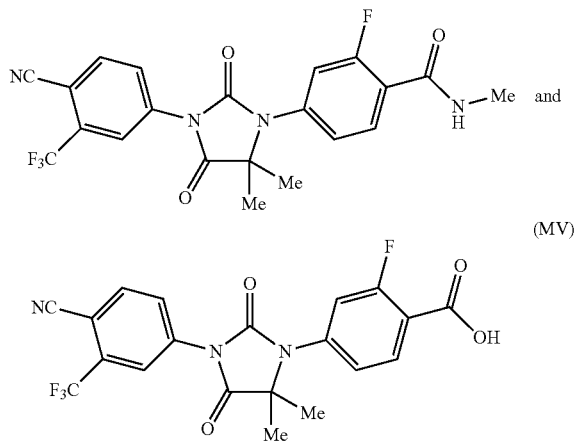

8. Salts

Salts of compounds described above can be used in the disclosed methods. If a compound has, for example, at least one basic center, it can form an acid addition salt. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4) alkyl or arylsulfonic acids which are unsubstituted or substituted, for example by halogen, for example methyl- or p-toluenesulfonic acid. Corresponding acid addition salts can also be formed having, if desired, an additionally present basic center. Compounds having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts can furthermore be formed. Salts which are unsuitable for pharmaceutical uses but which can be employed, for example, for the isolation or purification of free compounds or their pharmaceutically acceptable salts, are also included. In some embodiments salts of compounds which contain a basic group include monohydrochloride, hydrogensulfate, methanesulfonate, phosphate or nitrate. In some embodiments salts of compounds which contain an acid group include sodium, potassium and magnesium salts and pharmaceutically acceptable organic amines.

In some embodiments the salts are pharmaceutically acceptable (e.g., non-toxic, physiologically acceptable) salts. Pharmaceutically acceptable salts retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Therapeutic Methods

In addition to the breast cancer indications discussed below and the therapeutic indications disclosed in U.S. Pat. No. 7,709,517; US 2011/0003839; WO 2010/118354; WO 2011/044327; and WO 2010/099238, compounds of Formulae (I), (II), (III), (IV), (V), and (VI) can be used to treat androgen receptor related diseases or conditions such as benign prostate hyperplasia, hair loss, and acne. These and related compounds may also be useful as modulators of other nuclear receptors, such as glucocorticoid receptor, estrogen receptor, and peroxisome proliferator-activated receptor, and as therapeutic agents for diseases in which nuclear receptors play a role, such as breast cancer, ovarian cancer, diabetes, cardiac diseases, and metabolism related diseases.

"Treating" or "treatment" as used herein is an approach for obtaining a beneficial or desired result, including, but not limited to, relief from a symptom, lessening of a symptom, and preventing a worsening of a symptom associated with the disease being treated. Treatment also includes, but is not limited to, any one or more of enhancing survival time, enhancing progression-free survival time, and reducing tumor size.

1. Breast Cancers

Compounds can be used to treat various forms of breast cancer, whether or not the breast cancers express androgen receptors or estrogen receptors. Breast cancers that can be treated include, but are not limited to, basal-like breast cancer, BRCA1-related breast cancer, medullary breast cancer, metaplastic breast cancer, special histologic type of breast cancer, triple negative breast cancer, and breast cancer resistant to endocrine therapy.

In some embodiment, patients to be treated are postmenopausal. In other embodiments patients to be treated are pre-menopausal. In other embodiments patients to be treated are peri-menopausal. In some embodiments patients to be treated are men.

In some embodiments breast cancers are ER+ (i.e., 1% or more of the cells tested express ER detectable by immunocytochemistry). In some embodiments, breast cancers contain cells that demonstrate estradiol-mediated growth. In some embodiments patients to be treated have no detectable circulating levels of estradiol. In some embodiments patients to be treated have circulating levels of estradiol greater than 10 pmol/L. In some embodiments patients to be treated have circulating levels of estradiol less than 10 pmol/L. In some embodiments estradiol levels are measured by a double-antibody procedure as described in Cummings et al., *JAMA* 287, 216-20, 2002.

i. Triple Negative Breast Cancer

In some of embodiments the breast cancer is a triple negative breast cancer including, but not limited to, subtypes of triple negative breast cancer such as of basal-like type 1 (BL1), basal-like type 2 (BL2), immunomodulatory (IM), mesenchymal (M), mesenchymal stem-like (MSL), and luminal androgen receptor (LAR) subtypes. "Triple negative breast cancer" as used herein is characterized by lack of estrogen receptor (ER), progesterone receptor (PR), and lack of overexpression or amplification of Her2neu. A tumor is negative for expression of ER or PR if fewer than 1% of the cells tested are positive for ER or PR, as measured by immunohistochemistry, and if the Her2 gene is not expressed (for example, amplification is not detected by FISH). Triple negative breast cancer is clinically characterized as more aggressive and less responsive to standard treatment and is associated with poorer overall patient prognosis. It is diagnosed more frequently in younger women and in women with BRCA1 mutations.

In some embodiments a triple negative breast cancer is AR+; i.e., it contains cells that express detectable androgen receptors as detected by immunohistochemistry, ligand binding, or other methods known in the art. In other embodiments a triple negative breast cancer is AR−.

ii. ER+ Breast Cancer Resistant to Endocrine Therapy

Approximately 75% of breast cancers express the estrogen receptor (ER) and are candidates for endocrine therapy. The selective ER modulator tamoxifen is the most commonly prescribed endocrine therapy; however, approximately 30 percent of tumors that retain estrogen (ER) do not respond to estrogen/ER directed therapies such as tamoxifen or aromatase inhibitors (AI) and nearly all patients with metastatic disease develop resistance. In such patients, a compound can provide a therapeutic intervention.

In some embodiments the breast cancer is ER+, i.e., it contains detectable levels of estrogen receptor, measured as described above, but is resistant to endocrine therapy. "Endocrine therapy" as used herein includes administration of one or more aromatase inhibitors (e.g., anastrozole, exemestane, letrozole) and/or administration of one or more estrogen receptor modulators (e.g., tamoxifen, raloxifen, fulvestrant). "Resistant to endocrine therapy" as used herein means that the tumors (primary or metastases) do not respond to one or more of the above treatments by shrinking, but rather remains the same size or increases in size, or that recur in response to such treatment at any time in the patient's livespan.

In some embodiments the breast cancer is ER+/AR+. In some embodiments the breast cancer is ER+/AR−. In some embodiments the breast cancer contains cells that are progesterone receptor positive (PR+) as detected by immunohistochemistry or ligand binding assays or any other method of detection. In some embodiments the breast cancer contains no detectable cells with progesterone receptors; e.g., the breast cancer is progesterone receptor negative (PR−). In some embodiments a breast cancer contains cells that are Her2 positive (Her2+) as detected by observable Her2 gene amplification after in situ hybridization. In some embodiments a breast cancer contains no detectable cells with amplification or expression or overexpression of Her2; e.g., the breast cancer is Her2 negative (Her2−). The progesterone receptors and Her2 can be present on the same or different populations of cells, which may be the same or different as the populations of cells expressing ER and/or AR.

In some embodiments a breast cancer is identified as AR+, ER+, and Her2+. In some embodiments a breast cancer is identified as AR+, ER+, and PR+. In some embodiments a breast cancer is identified as AR+, ER+, Her2+, and PR+. In some embodiments a breast cancer is identified as AR−, ER+, and Her2+. In some embodiments a breast cancer is identified as AR−, ER+, and PR+. In some embodiments a breast cancer is identified as AR−, ER+, Her2+, and PR+. In some embodiments, a breast cancer is identified as AR+, ER−, HER2+, PR−.

2. Pharmaceutical Compositions

Compounds can be formulated in any type of pharmaceutical composition known in the art, including, but not limited to, tablets, troches, pills, capsules, syrups, elixirs, injectable solutions, and the like.

A pharmaceutical composition typically includes a pharmaceutically or pharmacologically acceptable excipient or carrier. As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. In some embodiments pharmaceutically acceptable carriers or excipients have met the required standards of toxicological and manufacturing testing and/or are included on the Inactive Ingredient Guide prepared by the U.S. Food and Drug administration.

The term "excipient" as used herein means an inert or inactive substance that may be used in the production of a drug or pharmaceutical, such as a tablet containing a compound as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, a diarylhydantoin compound can be incorporated into sustained-release preparations and devices. For example, a compound can be incorporated into time release capsules, time release tablets, and time release pills.

Pharmaceutical dosage forms suitable for injection or infusion can include sterile aqueous solutions or dispersions or sterile powders comprising a compound which are adapted for the extemporaneous preparation of sterile injectable or infusible solutions or dispersions, optionally encapsulated in liposomes. The ultimate dosage form typically is sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, isotonic agents are included, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating a compound in the required amount in the appropriate solvent with various of the other ingredients enumerated above, as required, followed by filter sterilization. In the case of sterile powders for the preparation of sterile injectable solutions, methods of preparation include vacuum drying and freeze drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

In some embodiments the pharmaceutical composition is a unit dosage form. As used herein, "unit dosage form" is a physically discrete unit containing a predetermined quantity of active.

3. Dosages

As used herein, the term "effective amount" intends such amount of a compound which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

Useful dosages of compounds can be determined by comparing their in vitro activity and/or in vivo activity in animal models. Methods for the extrapolation of effective dosages in mice, and other animals, to humans are known to the art; for example, see U.S. Pat. No. 4,938,949. For example, the concentration of a compound in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of a compound required for use in treatment will vary not only with the particular salt selected but also with the route of administration, the nature of the condition being treated and the age and condition of the patient and will be ultimately at the discretion of the attendant physician or clinician.

Effective dosages and routes of administration of compounds are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model can also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment can involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose can be about 1 mg/kg, 10 mg/kg, or 50 mg/kg of body weight per day.

A compound is conveniently administered in unit dosage form; for example, containing 0.05 to 10000 mg, 0.5 to 10000 mg, 5 to 1000 mg, or about 100 mg of active ingredient per unit dosage form.

A compound can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels can be from about 1 to 100 micromolar or from about 10 to about 25 micromolar. This can be achieved, for example, by the intravenous injection of a 0.05 to 5% solution of a diarylhydantoin or hydantoin compound, optionally in saline, or orally administered as a bolus containing about 1-100 mg of a diarylhydantoin or hydantoin compound. Desirable blood levels can be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of a compound per kg of body weight.

A compound can conveniently be presented in a single dose or as divided doses administered at appropriate intervals, for example, as two, three, four or more sub-doses per day. The sub-dose itself can be further divided, e.g., into a number of discrete loosely spaced administrations; such as multiple inhalations from an insufflator.

4. Methods of Administration

A compound can be administered using pharmaceutical compositions comprising a therapeutically effective amount of the compound and a pharmaceutically acceptable carrier or diluent, in a variety of forms adapted to the chosen route of administration, for example, orally, nasally, intraperitoneally, or parenterally, by intravenous, intramuscular, topical or subcutaneous routes, or by injection into tissue.

A compound can be systemically administered, e.g., orally, in combination with a pharmaceutically acceptable vehicle such as an inert diluent or an assimilable edible carrier; or by inhalation or insufflation. It can be enclosed in hard or soft shell gelatin capsule, can be compressed into a tablet, or can be incorporated directly with the food of a patient's diet. For oral therapeutic administration, a compound can be combined with one or more excipients and used in the form of an ingestible tablet, a buccal tablet, troche, capsule, elixir, suspension, syrup, wafer, and the like. A compound can be combined with a fine inert powdered carrier and inhaled by the subject or insufflated. In some embodiments such compositions and preparations contain at least 0.1% diarylhydantoin or hydantoin compound. The percentage of the compositions and preparations can, of course, be varied and can conveniently be between about 2% to about 60% of the weight of a given unit dosage form. The amount of diarylhydantoin or hydantoin compound in such therapeutically useful compositions is such that an effective dosage level will be obtained.

A compound can also be administered intravenously or intraperitoneally by infusion or injection. Solutions of a compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

5. Combination Therapies

In some embodiments combinations of one or more compounds are used. A "combination" compounds includes one or more compounds administered substantially simultaneously, whether or not in the same pharmaceutical composition, or sequentially. compounds can, but need not be, chemically similar (e.g., two diarylhydantoin compounds; a diarylhydantoin compound and a diarylthiohydantoin, etc.).

In some embodiments one or more compounds is combined other therapies, such as internal or external radiation, surgery, and chemotherapies, including:

1. anthracyclines, such as doxorubicin (e.g., ADRIAMYCIN®, DOXIL®), including liposomal doxorubicin, epirubicin (e.g., ELLENCE®), and daunorubicin (e.g., CERUBIDINE®, DAUNOXOME®);
2. taxanes, such as docetaxel (e.g., TAXOTERE®), paclitaxel (e.g., TAXOL®, ABRAXANE®, and protein-bound paclitaxel (e.g., ABRAXANE®);
3. estrogen receptormodulators, such as tamoxifen (e.g., NOLVADEX®, SOLTAMOX®, ISTUBAL®, VALODEX®);
4. cyclophosphamide (e.g., CYTOXAN®);
5. capecitabine (e.g., XELODA®)
6. 5-fluorouracil or 5 FU (e.g., ADRUCIL®);
7. vinorelbine (e.g., NAVELBINE®);
8. gemcitabine (e.g., GEMZAR®);
9. trastuzumab (e.g., HERCEPTIN®);
10. carboplatin (e.g., PARAPLATIN®);
11. eribulin (e.g., HALAVEN®);
12. ixabepilone (e.g., IXEMPRA®);
13. methotrexate (e.g., AMETHOPTERIN®, MEXATE®, FOLEX®);
14. mutamycin (e.g., MITOMYCIN®);
15. mitoxantrone (e.g., NOVANTRONE®);
16. thiotepa (e.g., THIOPLEX®);
17. vincristine (e.g., ONCOVIN®, VINCASAR PES®, VINCREX®);

18. aromatase inhibitors such as anastrozole (e.g., ARIMIDEX), exemestane (AROMASIN), and letrozole (FEMARA);
19. raloxifene (e.g., EVISTA®);
20. toremifene (e.g., FARESTON®);
21. fulvestrant (e.g., FASLODEX®);
22. lapatinib (e.g., TYKERB®); and
23. metformin.

One or more compounds also can be used in conjunction with combinations of chemical therapies, such as:
1. doxorubicin and docetaxel (e.g., "AT," ADRIAMYCIN® and TAXOTERE®);
2. doxorubicin and cyclophosphamide, with or without paclitaxel or docetaxel (e.g. "AC±T," ADRIAMYCIN® and CYTOXAN®, with or without TAXOL® or TAXOTERE®);
3. cyclophosphamide, methotrexate, and fluorouracil (e.g., "CMF," CYTOXAN®, methotrexate, and fluorouracil);
4. cyclophosphamide, epirubicin, and fluorouracil (e.g., "CEF," CYTOXAN®, ELLENCE®, and fluorouracil);
5. fluorouracil, doxorubicin, and cyclophosphamide (e.g., "FAC," fluorouracil, ADRIAMYCIN®, and CYTOXAN® or "CAF," CYTOXAN®, ADRIAMYCIN®, and fluorouracil);
6. docetaxel, doxorubicin, and cyclopho9sphamide (e.g., "TAC," TAXOTERE®, ADRIAMYCIN®, and CYTOXAN®); and
7. gemcitabine, epirubicin, and paclitaxel (e.g., "GET," GEMZAR®, ELLENCE®, and TAXOL®).

Other therapeutic agents which can be combined with compounds disclosed herein include:
1. PI3K/mTOR inhibitors, such as everolimus (e.g., AFINITOR®); temsirolimus (e.g., TORISEL®); rapamycin (sirolimus; e.g., RAPAMMUNE®); and radaforolimus;
2. EGFR inhibitors, such as trastuzumab; trastuzumab entansine (TDM1); pertuzumab (e.g., PERJECTA™); gefinitib (e.g., IRESSA®), neratinib (HK1-272); afatinib; erlotinib (e.g., TARCERA®);
3. angiogenesis inhibitors, such as bevacizumab (e.g., AVASTIN®); ramucirumab; sunitinib (e.g., SUTENT®); pazopanib (e.g., VOTRIENT®); sorafenib (e.g., NEXAVAR®); vandetanib (e.g., CAPRELSA®); and cediranib (e.g., RECENTIN®);
4. cytotoxics, such as vinflunine (e.g., JAVLOR®); trabectedin (e.g., YONDELIS®); and NKTR-102 (PEG-IRINOTECAN®);
5. vaccines, such as NeuVax™ (E75 peptide derived from HER2 combined with the immune adjuvant granulocyte macrophage colony stimulating factor (GM-CSF);
6. Bcr-Abl kinase inhibitors, such as imatinib (e.g., GLEEVEC®); and dasatinib (e.g., SPRYCEL®);
7. bone targeting agents, such as denosumab (e.g., PROLIA®, XGEVA®); and zoledronic acid (e.g., ZOMETA®, RECLAST®);
8. GnRH analogs, such as goserelin (e.g., Zoladex®); leuprolide (e.g., LUPRON®); degarelix (e.g., FIRMAGON®); nafarelin (e.g., SYNAREL®);
9. anthracyclines, such as idarubicin (e.g., IDAMYCIN®); inparib; gefinitib (e.g., IRESSA®); cetuximab (e.g., ERBITUX®); irinotecan (ERBITUX®); megestrol acetate (e.g., MEGACE®);
10. PARP inhibitors, such as olaparib; veliparib; MK4827;
11. Akt inhibitors, such as hexadecylphosphocholine (e.g., MILTEFOSINE®); and
12. Her3 inhibitors, such as U3-1287.

Nothing in this specification should be considered as limiting the scope of this disclosure. All examples presented are representative and non-limiting. The above-described embodiments can be modified or varied, as appreciated by those skilled in the art in light of the above teachings. It is therefore to be understood that, within the scope of the claims and their equivalents, the embodiments disclosed herein can be practiced otherwise than as specifically described.

Example 1

RD162' Blocks DHT-Mediated Proliferation in MCF7 Cells

MCF7 cells are commonly used luminal breast cancer cells that express high levels of ER and some AR. MCF7 cells were plated in phenol red-free medium containing charcoal stripped serum. The next day, cells were treated with vehicle alone (ethanol, EtOH), 10 nM dihydrotestosterone (DHT), 10 µM RD162' (RD162'), or a combination of DHT+RD162'. An in vitro proliferation assay using the tetrazolium salt MTT was performed at various time points. The values were normalized to an untreated plate read 24 hours after plating to account for differences in cell density. The results are shown in FIG. 1. These experiments demonstrated that RD162' blocks DHT-mediated growth of MCF7 cells.

Example 2

RD162' Blocks DHT-Mediated Growth in BCK4 Cells

Figure 2:
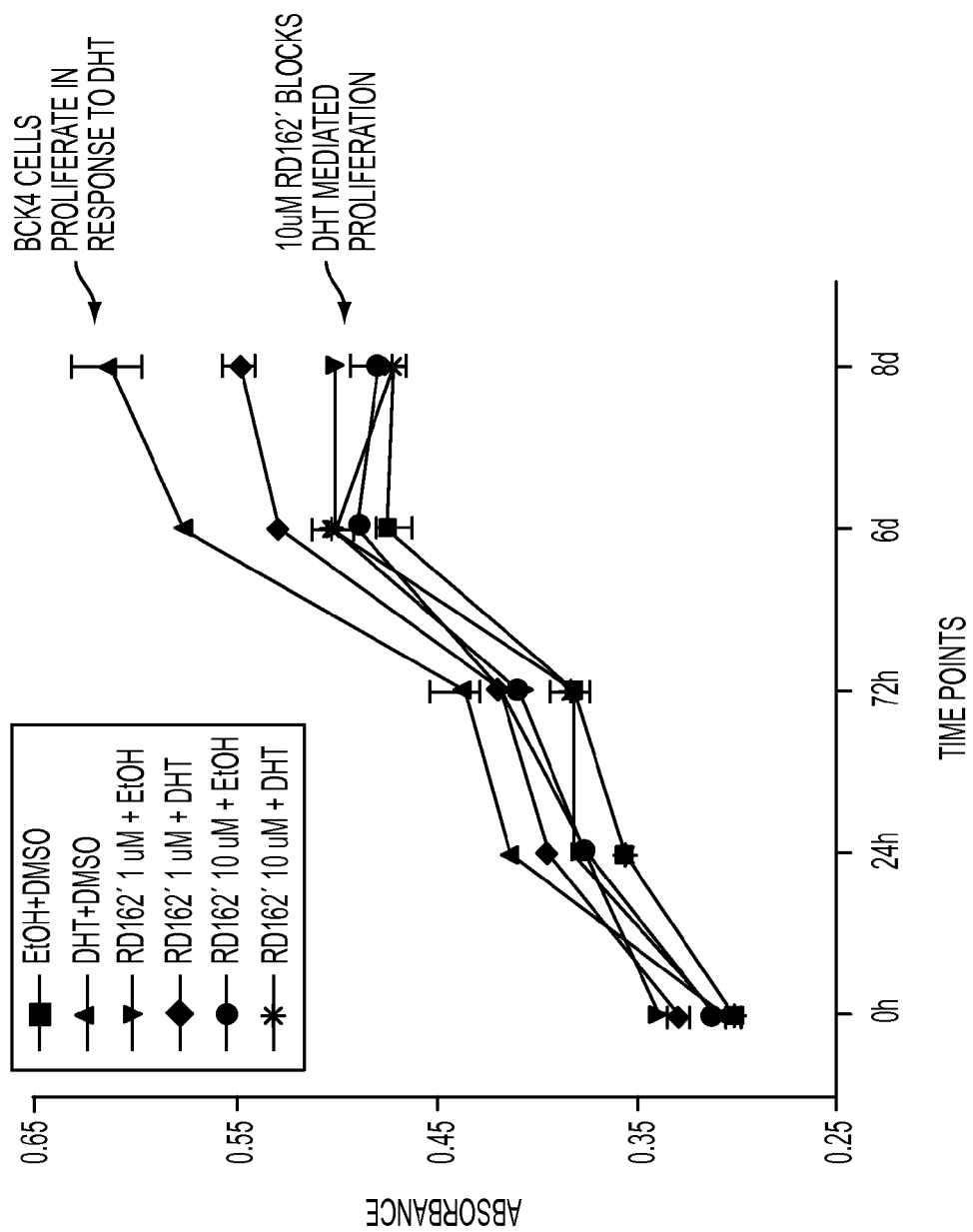
FIG. 2. Graph demonstrating that RD162' blocks DHT-mediated growth in BCK4 cells.

BCK4 cells are breast cancer cells that express more AR than ER and respond better to androgens than to estrogens. Proliferation of BCK4 cells was assayed as described above in the presence of DHT and in the presence of RD162' and DHT. The results are shown in FIG. 2. These experiments demonstrated that RD162' blocks DHT-mediated growth of BCK4 cells.

Example 3

RD162' Blocks Estradiol-Mediated Growth in MCF7 Cells

Figure 3B:
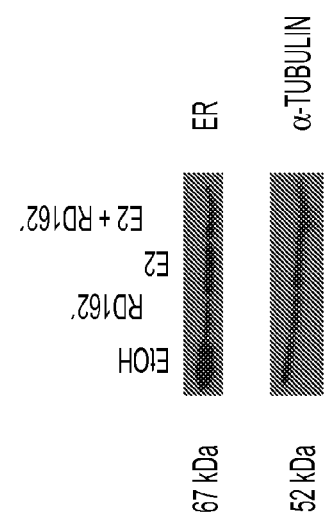
FIGS. 3A-B.
Figure 3A:
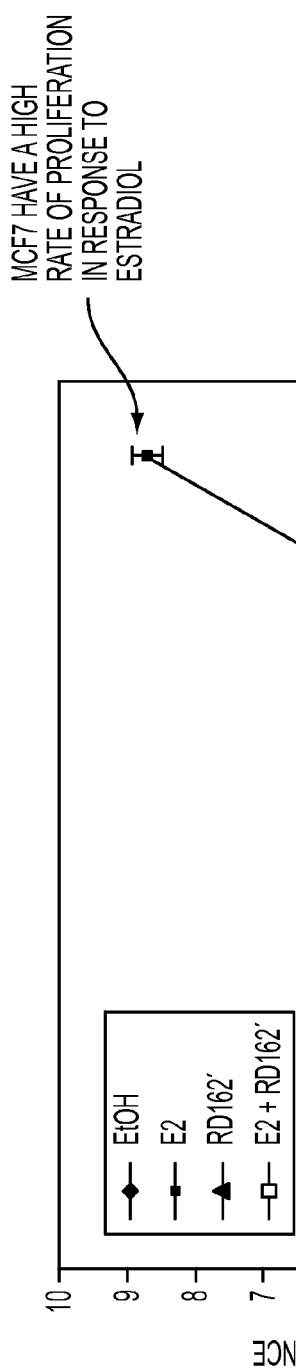

MCF7 cells were plated in phenol red-free medium containing charcoal stripped serum. The next day, cells were treated with vehicle alone (EtOH), 10 nM estradiol (E2), 10 µM RD162', or a combination of E2 and RD162'. An MTT assay was performed at various time points. The values were normalized to an untreated plate read 24 hours after plating to account for differences in cell density. The results are shown in FIG. 3. This experiment demonstrates that RD162' blocks estradiol-mediated growth of MCF7 cells.

Example 4

RD162' Blocks E2-Mediated Upregulation of SDF-1 and Progesterone Receptor Gene Expression Expression of SDF-1, a gene involved in estrogen mediated proliferation, and the progesterone receptor gene (a known estrogen regulated gene and marker of ERα activity, were assayed in the presence or absence of estradiol (E2).

Figure 4:
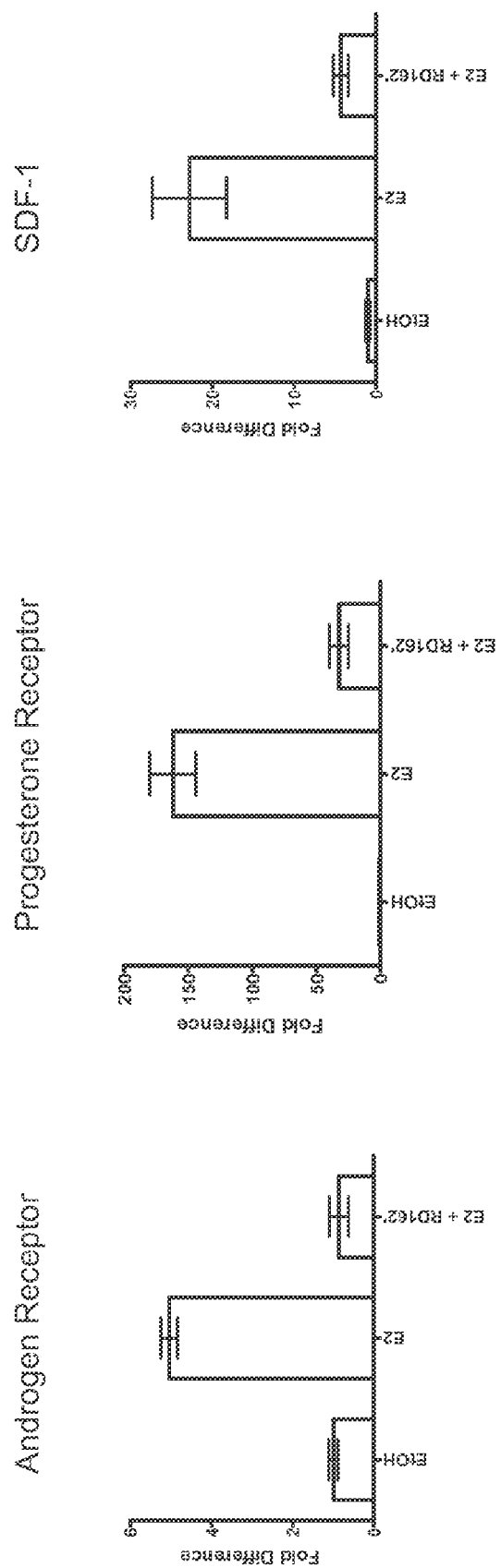
FIG. 4. Graph demonstrating that RD162' blocks E2-mediated upregulation of SDF-1, a gene involved in E2-driven proliferation, progesterone receptor, and androgen receptor.

RD162' blocks E2-mediated upregulation of these E2/ER regulated genes, indicating that RD162' modulates ERα activity, as shown in FIG. 4.

Example 5

Figure 5B:
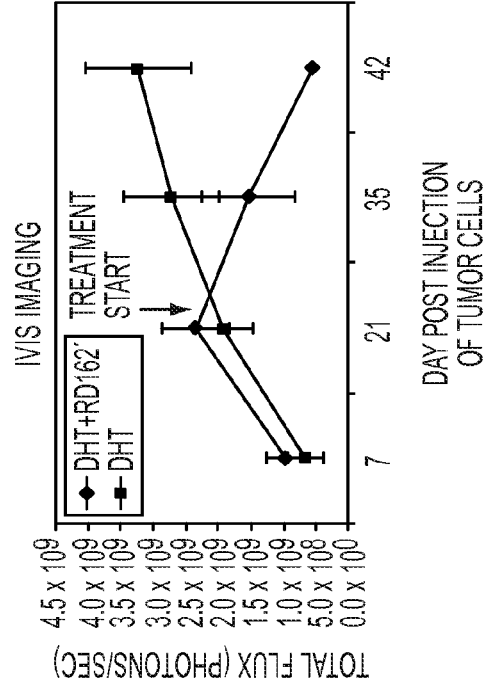
FIGS. 5A-D. Graphs demonstrating that RD162' inhibits DHT-mediated tumor growth in vivo as described in Example 5.
Figure 5D:
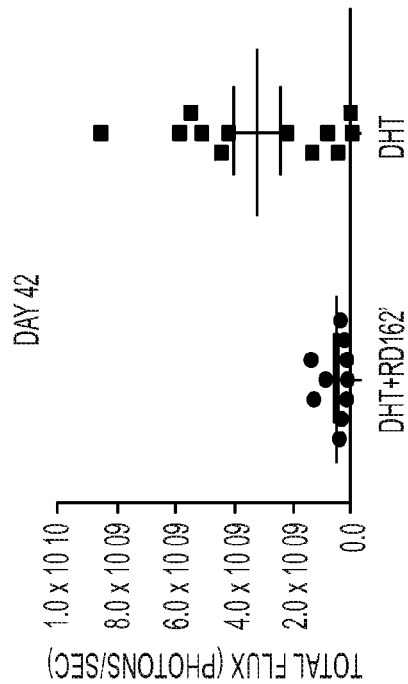
Figure 5A:
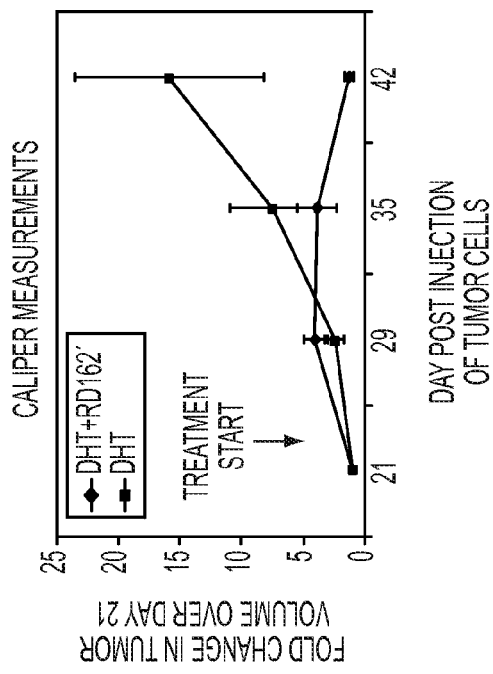
Figure 5C:
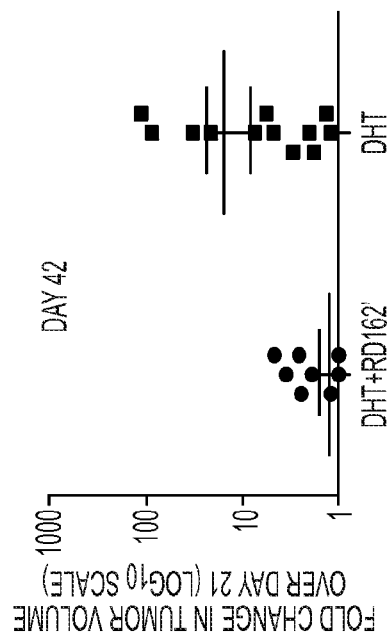

In Vivo Studies Demonstrating that RD162' Inhibits DHT-Mediated Growth in MCF7 Cells Grown in the Mammary Glands of nod-scid Mice MCF7 cells ($1\times10^6$ cells) engineered to express luciferase were mixed with 100 μl of matrigel and injected into the mammary fat pad of 6-8 week old ovariectomized nod/scid mice. Two tumors were implanted per mouse, one on each side. The mice had a DHT pellet implanted subcutaneously at the time of injection of tumor cells. Tumor burden was measured by either caliper or whole body in vivo luminescent (IVIS) imaging. At day 22, mice were matched based on tumor burden measured by IVIS imaging and separated into two groups. One group received a control chow and the other received chow containing 50 mg/kg RD162'. The results are shown in FIGS. 5A-D. FIGS. 5A-B depict tumor growth over time. FIGS. 5C-D show individual tumor size at the end of the study.

Example 6

RD162' Blocks Proliferation of Triple Negative Breast Cancer Cells

A Western blot of four luminal (ER+, PR+) and four triple negative (ER−, PR−, Her2−) breast cancer cell lines for androgen receptor, estrogen receptor and tubulin (as a loading control) was prepared (FIG. 6A). Three of the triple negative cell lines have robust AR expression.

MDA468 and BT20 cells were plated in phenol red-free medium containing charcoal stripped serum. The next day, cells were treated with vehicle alone (EtOH), 10 nM dihydrotestosterone (DHT), 10 μM RD162', or a combination of DHT and RD162'. An MTT assay was performed at various time points. The values were normalized to an untreated plate read 24 hours after plating to account for differences in cell density. The results are shown in FIGS. 6B-C. This experiment demonstrates that RD162' blocks growth of triple negative breast cancer cells.

Example 7

Figure 7A:
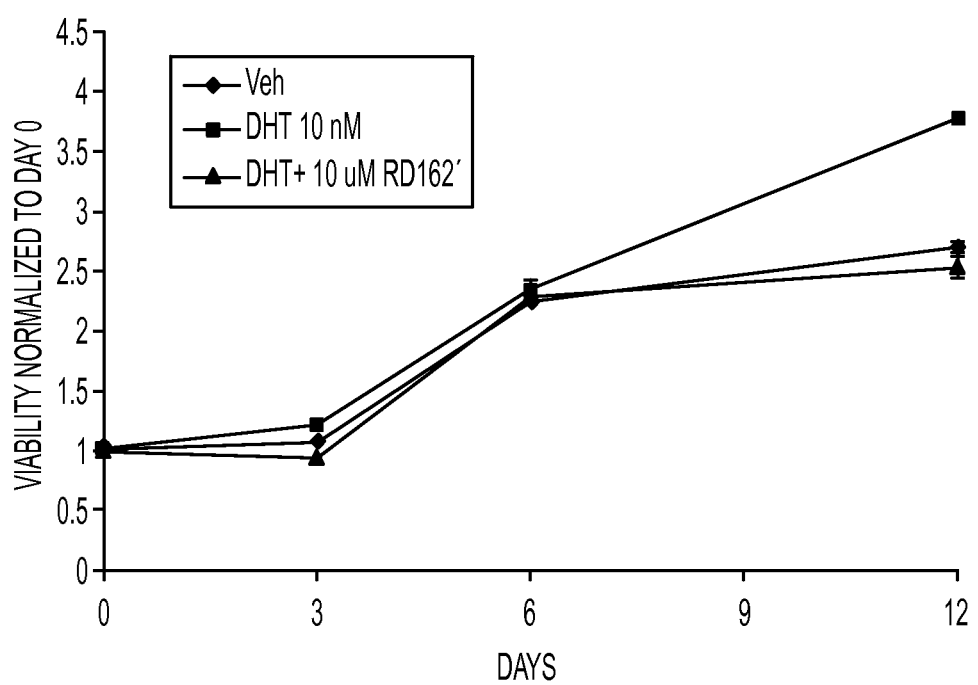

RD162' Inhibits DHT-Induced Proliferation in Apocrine Breast Cancer Cells (AR+, ER−, HER2+, PR−) and Inhibits the In Vivo Growth of these Cells in a Xenograft Model in Mammary Glands of NOD SCID Mice The effect of RD162' on DHT-induced proliferation of apocrine breast cancer cells was assessed in MDA-MB-453 cells, which are AR+, ER−, HER2+, and PR−, using a colorimetric in vitro proliferation assay using the tetrazolium salt MTS ("MTS assay") and a luciferase assay. The results of the MTS assay are shown in FIG. 7A. These results indicate that 10 μM RD162' inhibits proliferation induced by 10 nM DHT.

Figure 7B:
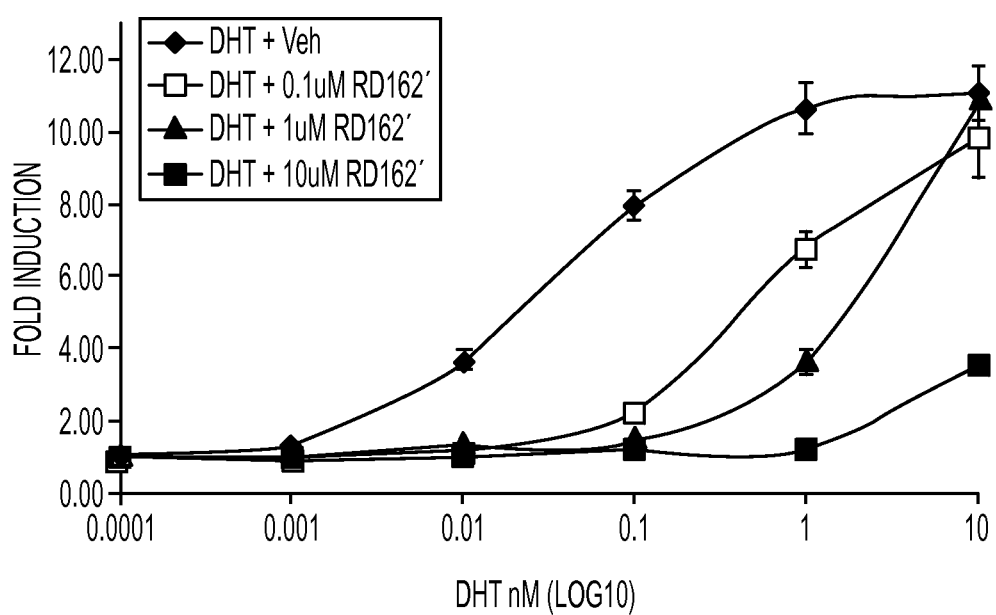

A luciferase assay carried out with MDA-kb2 cells, which were derived from MDA-MB-453 cells but contain an androgen-dependent luciferase reporter, demonstrated that RD162' inhibits proliferation induced by DHT in a dose dependent manner. The results are shown in FIG. 7B. Error bars reflect the SEM of independent experiments and * indicates P<0.05,  indicates P<0.01, * indicates P<0.001 (ANOVA with Bonferroni's multiple comparison test correction).

Immunocytochemical assays were carried out in MDA-kb2 cells using an antibody to AR. Cells were treated for 3 hours with vehicle (Vh), 1 nM DHT, 10 μM RD162', or 10 μM RD162' and DHT. The graph shown in FIG. 7C displays the ratio of nuclear to total AR for all cells measured. The results demonstrate that RD162' inhibits nuclear translocation of AR induced by DHT.

In vivo growth of apocrine breast cancer cells was investigated in a xenograft model in mammary glands of NOD SCID mice. MDA-MB-453 cells ($6\times10^6$) were injected into the 4$^{th}$ inguinal mammary fat pad of NOD-SCID-IL2Rgc−/− female mice. A 60-day release DHT pellet was implanted subcutaneously into 3 groups of mice at the time of cell injection. Tumor size was measured using calipers and once the tumors reached 100 mm$^3$, the mice began receiving 10 mg/kg/d RD162', 25 mg/kg/d RD162' or vehicle by oral gavage.

Figure 7D:
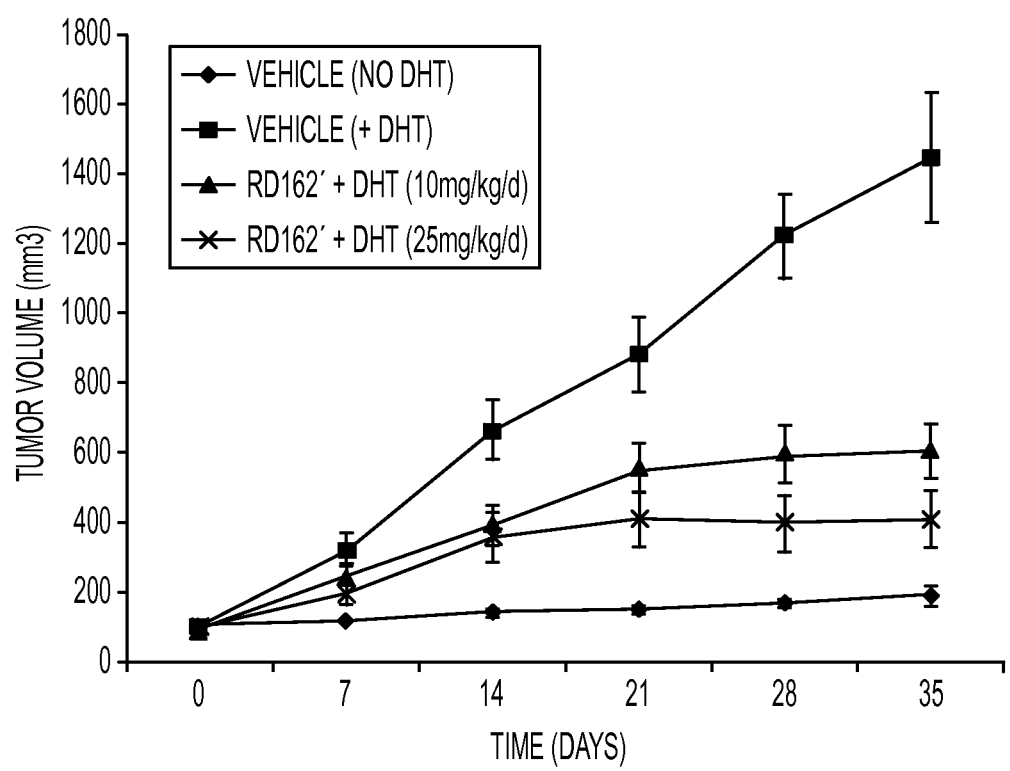
Figure 7E:
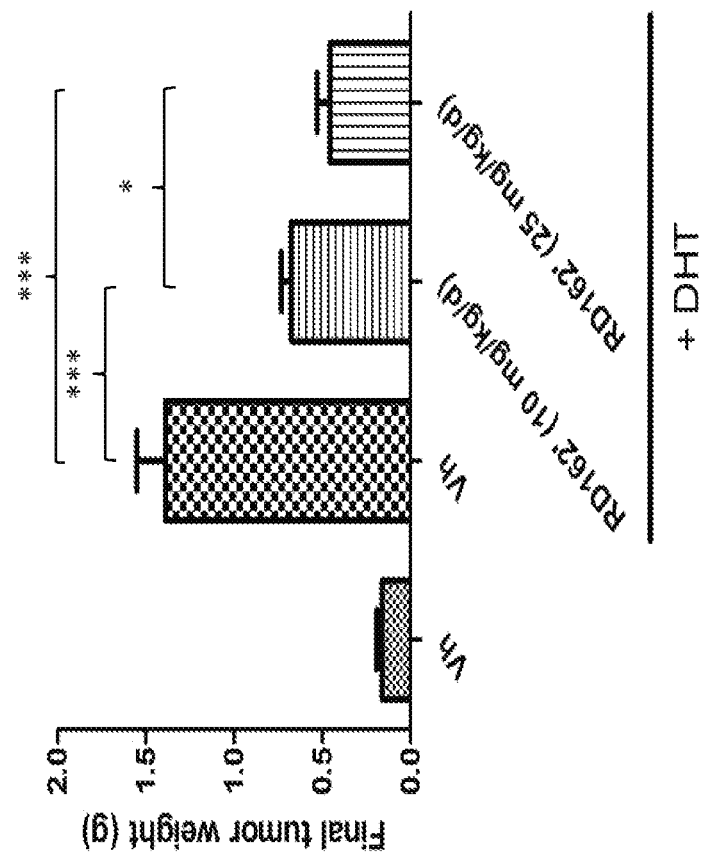

The results are shown in FIG. 7D and FIG. 7E. The results demonstrate that RD162' at either dose inhibited tumor growth induced by DHT (FIG. 7D). Tumors were weighed at necropsy and both doses of RD162' significantly inhibited DHT induced tumor growth (FIG. 7E). Error bars reflect the SEM and * indicates P<0.05, *** indicates P<0.001 (Mann Whitney).

Example 8

RD162' Inhibits the Growth of Triple Negative Breast Cancer Cells

Figure 8:
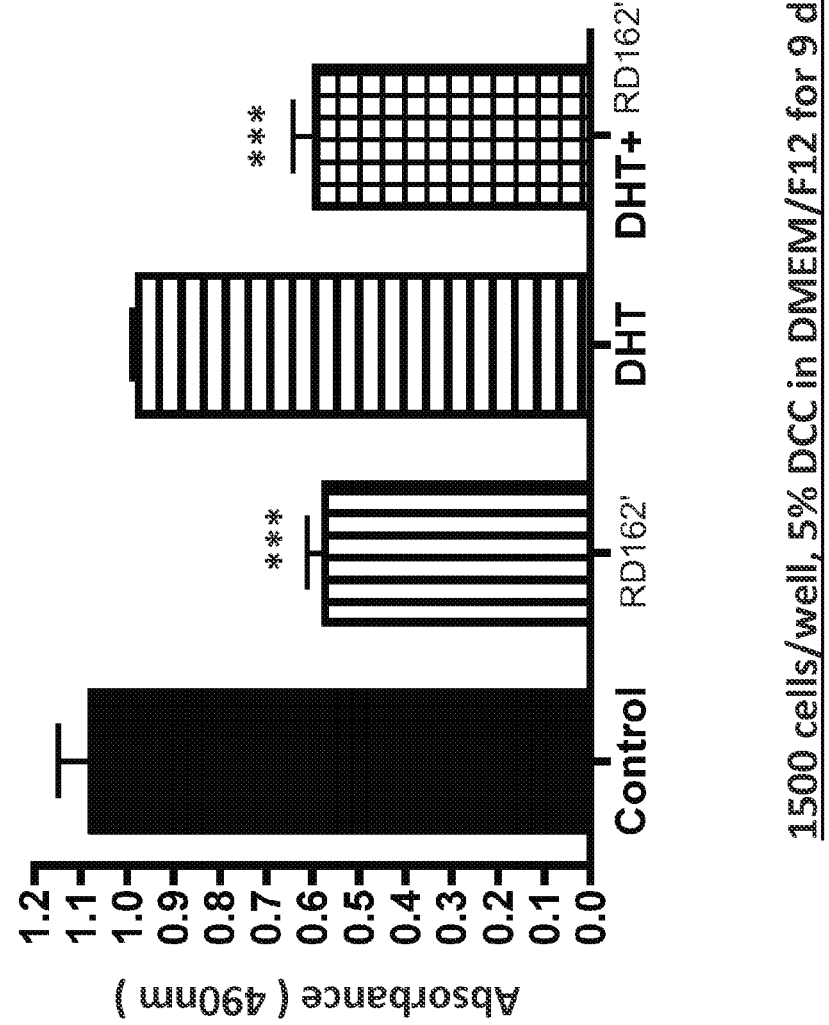
FIG. 8. Graph demonstrating that RD162' inhibits the growth of triple negative breast cancer cells.

Hs578T, a TNBC cell line, was plated in phenol red free DMEM/F12 containing 5% DCC for 2 days before treated with vehicle control, RD162' (10 μM), DHT (10 nM), and RD162'+DHT for 9 days. Viable cells were assayed by MTS assay. The results are shown in FIG. 8. Averages of the triplicate data points are shown with standard deviation. ***p<0.001 (two-tail t-test). Note that DHT treatment does not increase the growth of Hs578T cells.

Example 9

Figure 9:
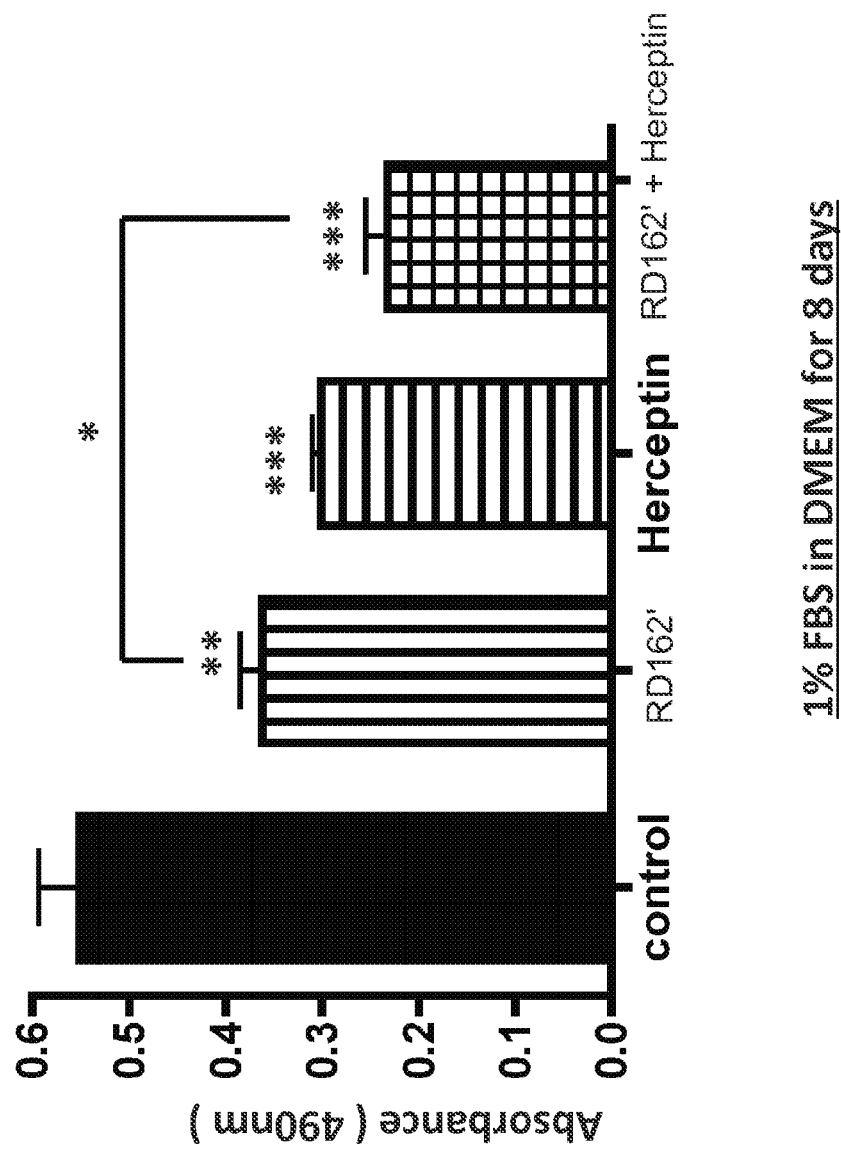
FIG. 9. Graph demonstrating that RD162' with HERCEPTIN® inhibits the growth of Her2+ breast cancer cells FIG. 10A. Graph showing weekly measurement of tumor volume.

RD162' Together with Herceptin Inhibits the Growth of Her2+ Breast Cancer Cells SKBR3, a Her2+ breast cancer cell line, was grown in DMEM+1% FBS in the presence of vehicle control, 10 μM RD162', 20 μg/ml of Herceptin, and RD162'+Herceptin respectively for 8 days before analyzed for viable cells with MTS assay. The results are shown in FIG. 9. Averages of the triplicate data points are shown with standard deviation. *p<0.05 and ***p<0.001 (two-tail t-test).

Example 10

RD162' Inhibits Androgen Stimulated Growth of MDA-MB-453 Tumors

MDA-MB-453 cells were injected orthotopically in the mammary gland of female NOD-SCID-IL2Rgc−/− mice. Three groups had a DHT pellet implanted SQ and one group had no pellet (Vehicle). Once the tumors reached 100 mm$^3$, the mice were given either RD162' (10 mg/kg) or vehicle (Vehicle and DHT groups) by daily oral gavage. When the tumors reached 400 mm³, another group was given a higher dose of RD162' (25 mg/kg,) by oral gavage. The results are shown in FIGS. 10A-D.

Figure 10A:
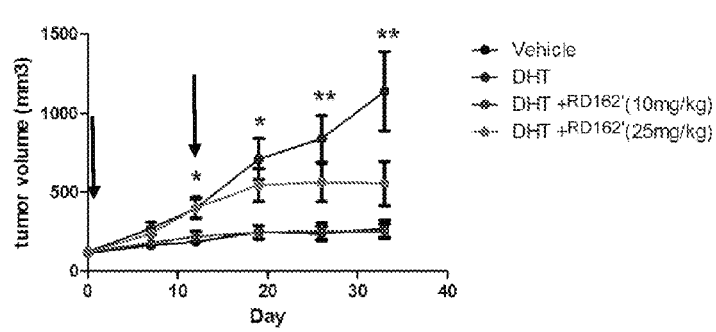
FIG. 10B. Graph showing weight of tumors at the end of the experiment described in Example 10.
FIG. 10C. Representative tumor sections stained for cleaved caspase 3.
FIG. 10D. Images of nuclear AR staining.
Figure 10B:
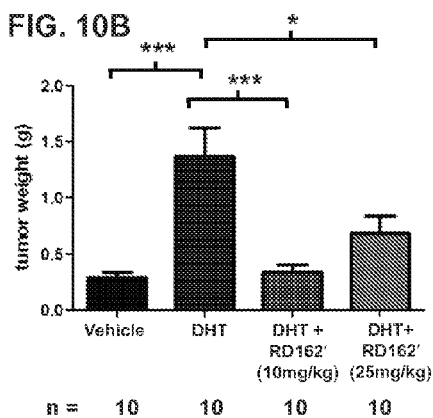
Figure 10C:
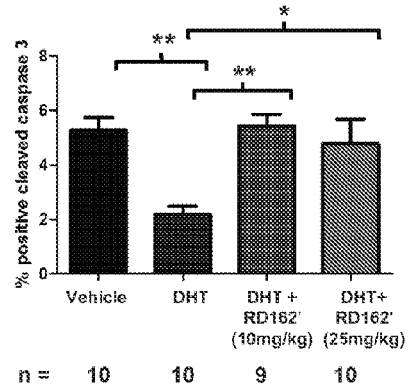
Figure 10C:
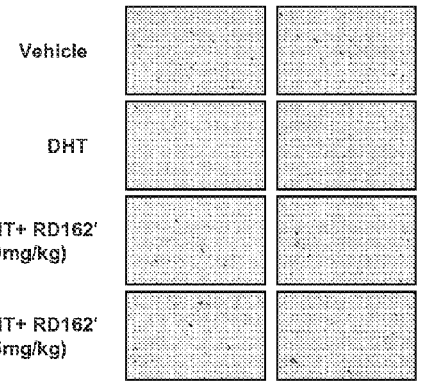
Figure 10D:
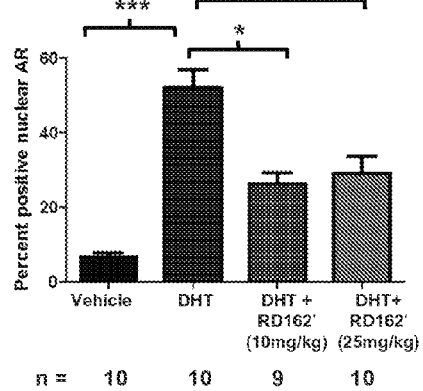
Figure 10D:
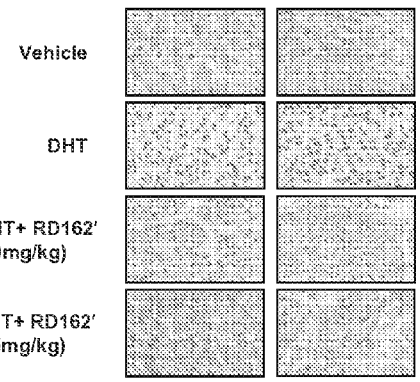

Tumor volume was measured weekly by caliper. Error bars represent SEM. * indicates P<0.05, ** indicates P<0.01 for DHT vs DHT+RD162' (10 mg/kg), Wilcoxon rank sum (FIG. 10A). There were no significant differences at any time point for DHT vs DHT+RD162' (25 mg/kg). Tumors were excised and weighed at the end of the experiment (FIG. 10B). Tumor sections stained for cleaved caspase 3 were quantified and representative images shown below (200× magnification). For tumor weights and cleaved caspase 3 staining, * indicates P<0.05,  indicates P<0.01, * indicates P<0.001, ANOVA with Bonferroni's multiple comparison test correction (FIG. 10C). Nuclear AR staining was quantified and representative images (400× magnification) are shown below. * indicates P<0.05, *** indicates P<0.001, Kruskal-Wallis with Dunn's multiple comparison test correction (FIG. 10D).

Example 11

Figure 11A:
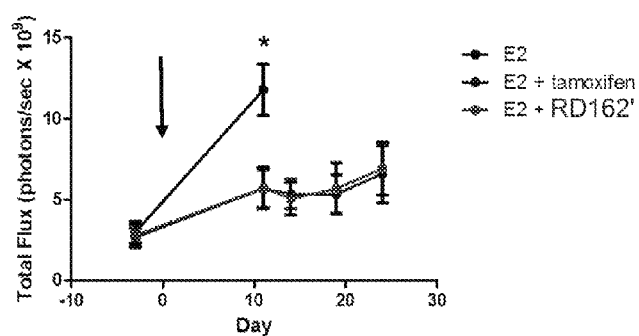
FIG. 11A. Graph showing mean total flux of all mice in each of the treatment groups.
Figure 11B:
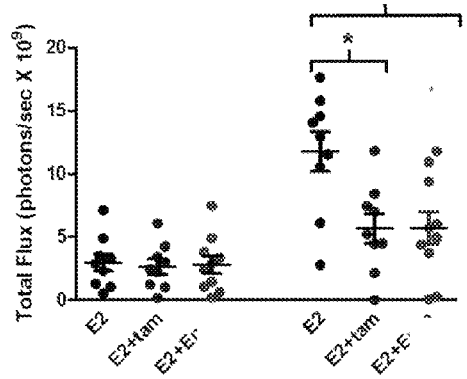
FIG. 11B. Graph showing the total luminescent flux is shown for all individual mice at the day of matching (Day −3) and at the final imaging day (Day 11).
Figure 11C:
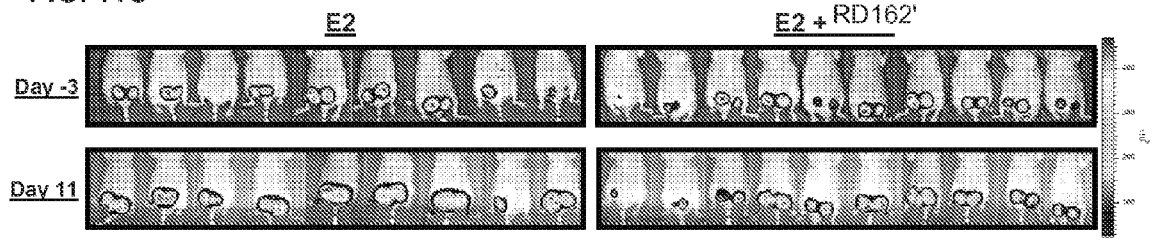
FIG. 11C. Images of luminescent signal in the two treatment groups at the day of matching (day −2) and the final day of imaging (day 11).
Figure 11D:
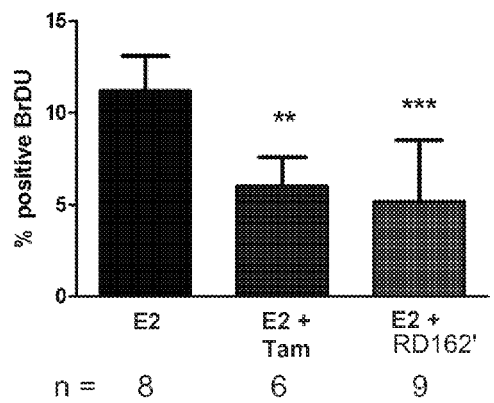
FIG. 11D. Representative images of BrdU staining (left, 400× magnification) and quantification (right).

RD162' is as Effective as Tamoxifen at Inhibiting Estrogen Stimulated Tumor Growth MCF7-TGL cells stably expressing luciferase were implanted orthotopically in the mammary gland of ovariectomized female nude mice. All mice had an E2 pellet implanted SQ and were either given control chow (E2), control chow plus a tamoxifen pellet implanted SQ (E2+ tam) or chow containing 50 mg/kg RD162' (E2+RD162'). The beginning of treatment is indicated by an arrow. Tumor burden was measured by whole body luminescence. The results are shown in FIGS. 11A-D. Mean total flux of all mice in each of the treatment groups is shown. Mice were matched on day –3 and treatment began on day 0. * indicates P<0.05, ANOVA with Bonferroni's multiple comparison test correction (FIG. 11A). The total luminescent flux is shown for all individual mice at the day of matching (Day –3) and at the final imaging day (Day 11). * indicates P<0.05, ANOVA with Bonferroni's multiple comparison test correction (FIG. 11B). Images of luminescent signal in the two treatment groups at the day of matching (day –2) and the final day of imaging (day 11) is shown (FIG. 11C). Mice were injected with BrdU two hours prior to sacrifice. Immunohistochemistry for BrdU was performed on tumor sections and quantified using image J. Representative images of BrdU staining (left, 400× magnification) and quantification (right) shown are shown.  indicates P<0.01 for E2 vs E2+Tamoxifen, * indicates P<0.001 for E2 vs E2+RD162', ANOVA with Bonferroni's multiple comparison test correction (FIG. 11D).

The invention claimed is:

1. A method of treating triple negative breast cancer, comprising administering to a patient in need thereof a therapeutically effective amount of a compound or a pharmaceutically acceptable salt of the compound, wherein the compound is selected from the group consisting of

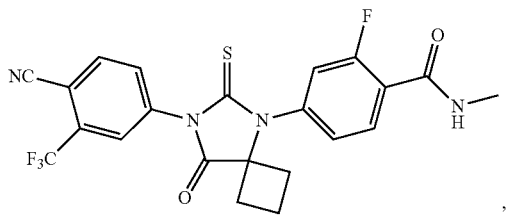

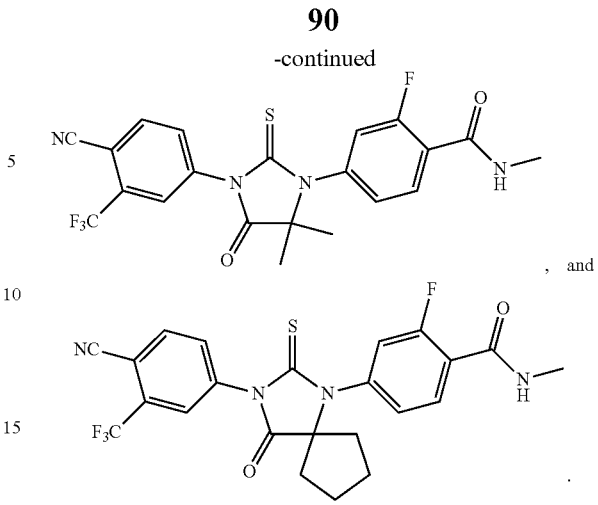

2. The method of claim 1, wherein the compound is enzalutamide:

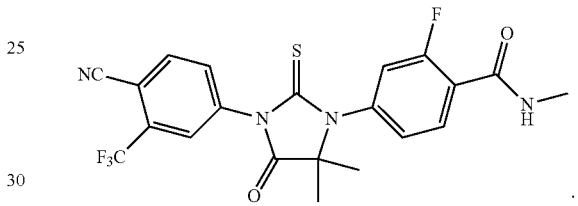

3. The method of claim 1, wherein the triple negative breast cancer is a subtype selected from the group consisting of basal-like type 1 (BL1), basal-like type 2 (BL2), immunomodulatory (IM), mesenchymal (M), mesenchymal stem-like (MSL), and luminal androgen receptor (LAR) subtypes.

4. The method of claim 1, wherein cells of the triple negative breast cancer comprise a BRCA1 mutation.

5. The method of claim 1, wherein the triple negative breast cancer comprises cells that do not express detectable androgen receptor.

6. The method of claim 1, wherein the triple negative breast cancer comprises cells that express an androgen receptor.

7. The method of claim 1, further comprising administering to the patient a second therapeutic treatment.

8. The method of claim 3, wherein the triple negative breast cancer is the BL1 subtype.

9. The method of claim 3, wherein the triple negative breast cancer is the BL2 subtype.

10. The method of claim 3, wherein the triple negative breast cancer is the IM subtype.

11. The method of claim 3, wherein the triple negative breast cancer is the M subtype.

12. The method of claim 3, wherein the triple negative breast cancer is the MSL subtype.

13. The method of claim 3, wherein the triple negative breast cancer is the LAR subtype.

14. The method of claim 4, wherein the compound is enzalutamide.

15. The method of claim 5, wherein the compound is enzalutamide.

16. The method of claim 6, wherein the compound is enzalutamide.

17. The method of claim 7, wherein the compound is enzalutamide.

18. The method of claim 8, wherein the compound is enzalutamide.

19. The method of claim 9, wherein the compound is enzalutamide.

20. The method of claim 10, wherein the compound is enzalutamide.

21. The method of claim 11, wherein the compound is enzalutamide.

22. The method of claim 12, wherein the compound is enzalutamide.

23. The method of claim 13, wherein the compound is enzalutamide.

\* \* \* \* \*